US007772375B2

(12) United States Patent
Greferath et al.

(10) Patent No.: US 7,772,375 B2
(45) Date of Patent: Aug. 10, 2010

(54) MONOCLONAL ANTIBODIES THAT RECOGNIZE EPITOPES OF AMYLOID-BETA

(75) Inventors: Ruth Greferath, Kehl (DE); David Hickman, La Tour de Trême (CH); Andreas Muhs, Pully (CH); Andrea Pfeifer, St.-Légier (CH); Claude Nicolau, Newton, MA (US)

(73) Assignee: AC Immune S.A., Lausanne (CH)

( * ) Notice: Subject to any disclaimer, the term of this patent is extended or adjusted under 35 U.S.C. 154(b) by 614 days.

(21) Appl. No.: 11/637,213

(22) Filed: Dec. 11, 2006

(65) Prior Publication Data

US 2007/0166311 A1 Jul. 19, 2007
US 2010/0098707 A2 Apr. 22, 2010

(30) Foreign Application Priority Data

Dec. 12, 2005 (EP) .................... 05027092
Jul. 14, 2006 (EP) .................... 06014729
Oct. 2, 2006 (EP) .................... 06020766

(51) Int. Cl.
C07K 16/18 (2006.01)
C12N 5/12 (2006.01)
A61K 39/395 (2006.01)
A61K 31/00 (2006.01)

(52) U.S. Cl. .............. 530/388.85; 424/141.1; 424/139.1; 435/331; 514/1

(58) Field of Classification Search ............... None
See application file for complete search history.

(56) References Cited

U.S. PATENT DOCUMENTS

| | | | |
|---|---|---|---|
| 4,666,829 A | 5/1987 | Glenner et al. |
| 5,218,100 A | 6/1993 | Muller-Hill et al. |
| 5,231,000 A | 7/1993 | Majocha et al. |
| 5,231,170 A | 7/1993 | Averback |
| 5,234,814 A | 8/1993 | Card et al. |
| 5,262,332 A | 11/1993 | Selkoe |
| 5,441,870 A | 8/1995 | Seubert et al. |
| 5,538,845 A | 7/1996 | Knops et al. |
| 5,567,720 A | 10/1996 | Averback |
| 5,593,846 A | 1/1997 | Schenk et al. |
| 5,605,811 A | 2/1997 | Seubert et al. |
| 5,665,355 A | 9/1997 | Primi |
| 5,679,531 A | 10/1997 | Konig |
| 5,693,753 A | 12/1997 | Konig |
| 5,705,401 A | 1/1998 | Masters et al. |
| 5,721,130 A | 2/1998 | Seubert et al. |
| 5,750,349 A | 5/1998 | Suzuki et al. |
| 5,766,846 A | 6/1998 | Schlossmacher et al. |
| 5,786,180 A | 7/1998 | Konig |
| 5,955,285 A | 9/1999 | Averback |
| 5,955,317 A | 9/1999 | Suzuki et al. |
| 6,018,024 A | 1/2000 | Seubert et al. |
| 6,114,133 A | 9/2000 | Seubert et al. |
| 6,218,506 B1 | 4/2001 | Krafft et al. |
| 6,284,221 B1 | 9/2001 | Schenk et al. |
| 6,287,793 B1 | 9/2001 | Schenk et al. |
| 6,294,171 B2 | 9/2001 | McMichael |
| 6,309,892 B1 | 10/2001 | Averback |
| 6,387,674 B1 | 5/2002 | Trasciatti et al. |
| 6,582,945 B1 | 6/2003 | Raso |
| 6,610,493 B1 | 8/2003 | Citron et al. |
| 6,664,442 B2 | 12/2003 | McConlogue et al. |
| 6,743,427 B1 | 6/2004 | Schenk |
| 6,750,324 B1 | 6/2004 | Schenk |
| 6,761,888 B1 | 7/2004 | Schenk |
| 6,787,138 B1 | 9/2004 | Schenk |
| 6,787,139 B1 | 9/2004 | Schenk |
| 6,787,140 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,815,175 B2 | 11/2004 | Weksler |

(Continued)

FOREIGN PATENT DOCUMENTS

CN 1396183 2/2003

(Continued)

OTHER PUBLICATIONS

Paul WE, Ed. Fundamental Immunology, Third Edition, 1993, Raven Press, New York, pp. 292-295.*

(Continued)

*Primary Examiner*—Jeffrey Stucker
*Assistant Examiner*—Kimberly A. Ballard
(74) *Attorney, Agent, or Firm*—Jones Day

(57) ABSTRACT

The present invention is related to methods and compositions for the therapeutic and diagnostic use in the treatment of diseases and disorders which are caused by or associated with amyloid or amyloid-like proteins including amyloidosis, a group of disorders and abnormalities associated with amyloid protein such as Alzheimer's disease. The present invention provides novel methods and compositions comprising highly specific and highly effective antibodies having the ability to specifically recognize and bind to specific epitopes from a range of β-amyloid proteins. The antibodies enabled by the teaching of the present invention are particularly useful for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD).

15 Claims, 4 Drawing Sheets

U.S. PATENT DOCUMENTS

Figure 3A:
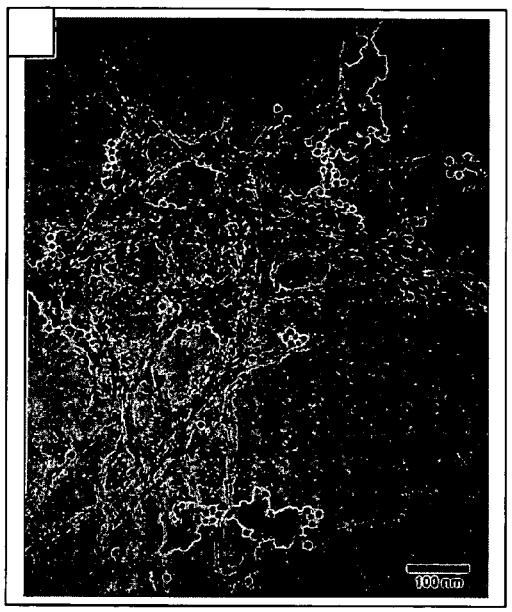

| | | | |
|---|---|---|---|
| 6,849,416 B2 | 2/2005 | Wiltfang et al. |
| 6,866,849 B2 | 3/2005 | Schenk |
| 6,866,850 B2 | 3/2005 | Schenk |
| 6,872,554 B2 | 3/2005 | Raso |
| 6,875,434 B1 | 4/2005 | Schenk |
| 6,905,686 B1 | 6/2005 | Schenk |
| 6,913,745 B1 | 7/2005 | Schenk |
| 6,972,127 B2 | 12/2005 | Schenk |
| 7,014,855 B2 | 3/2006 | Schenk |
| 7,022,500 B1 | 4/2006 | Queen et al. |
| 7,060,270 B2 | 6/2006 | Nicolau et al. |
| 7,067,133 B2 | 6/2006 | Nicolau |
| 7,179,892 B2 | 2/2007 | Basi et al. |
| 7,189,819 B2 | 3/2007 | Basi et al. |
| 7,195,761 B2 | 3/2007 | Holtzman et al. |
| 7,256,273 B2 | 8/2007 | Basi et al. |
| 7,318,923 B2 | 1/2008 | Tsurushita et al. |
| 7,320,790 B2 | 1/2008 | Hinton et al. |
| 7,335,491 B2 | 2/2008 | Drapeau et al. |
| 7,339,035 B2 | 3/2008 | Yanagisawa et al. |
| 7,371,365 B2 | 5/2008 | Poduslo et al. |
| 7,413,884 B2 | 8/2008 | Raso |
| 7,427,342 B2 | 9/2008 | Barber |
| 2001/0029293 A1 | 10/2001 | Gallatin et al. |
| 2002/0009445 A1 | 1/2002 | Du et al. |
| 2002/0086847 A1 | 7/2002 | Chain |
| 2002/0094335 A1 | 7/2002 | Chalifour et al. |
| 2002/0182660 A1 | 12/2002 | Fong |
| 2002/0197258 A1 | 12/2002 | Ghanbari et al. |
| 2003/0068316 A1 | 4/2003 | Klein et al. |
| 2003/0108551 A1 | 6/2003 | Nicolau et al. |
| 2003/0147882 A1 | 8/2003 | Solomon et al. |
| 2003/0190689 A1 | 10/2003 | Crosby et al. |
| 2003/0232758 A1 | 12/2003 | St. George-Hyslop et al. |
| 2004/0043418 A1 | 3/2004 | Holtzman et al. |
| 2004/0058414 A1 | 3/2004 | Queen et al. |
| 2004/0142872 A1 | 7/2004 | Poduslo et al. |
| 2004/0146512 A1 | 7/2004 | Rosenthal et al. |
| 2004/0175394 A1* | 9/2004 | Schenk ............... 424/185.1 |
| 2004/0191264 A1 | 9/2004 | Nielsen et al. |
| 2004/0192898 A1 | 9/2004 | Jia et al. |
| 2004/0213800 A1 | 10/2004 | Seubert et al. |
| 2004/0223912 A1 | 11/2004 | Montalto et al. |
| 2004/0241164 A1 | 12/2004 | Bales et al. |
| 2004/0242845 A1 | 12/2004 | Nicolau et al. |
| 2004/0248197 A1 | 12/2004 | Holtzman et al. |
| 2004/0265919 A1 | 12/2004 | Vanderstichele et al. |
| 2005/0031651 A1* | 2/2005 | Gervais et al. ............... 424/400 |
| 2005/0118651 A1 | 6/2005 | Basi et al. |
| 2005/0124016 A1 | 6/2005 | LaDu et al. |
| 2005/0129691 A1 | 6/2005 | Gerlai |
| 2005/0129695 A1 | 6/2005 | Mercken et al. |
| 2005/0147613 A1 | 7/2005 | Raso |
| 2005/0169925 A1 | 8/2005 | Bardroff et al. |
| 2005/0175626 A1 | 8/2005 | Delacourte et al. |
| 2006/0008458 A1 | 1/2006 | Solomon |
| 2006/0057646 A1 | 3/2006 | Wiltfang et al. |
| 2006/0057701 A1 | 3/2006 | Rosenthal et al. |
| 2006/0073149 A1 | 4/2006 | Bales et al. |
| 2006/0110388 A1 | 5/2006 | Davies et al. |
| 2006/0111301 A1 | 5/2006 | Mattner |
| 2006/0127954 A1 | 6/2006 | Mercken et al. |
| 2006/0160161 A1 | 7/2006 | Pavliakova et al. |
| 2006/0165682 A1 | 7/2006 | Basi et al. |
| 2006/0193850 A1 | 8/2006 | Warne et al. |
| 2006/0198851 A1 | 9/2006 | Basi et al. |
| 2006/0228349 A1 | 10/2006 | Acton et al. |
| 2006/0246075 A1 | 11/2006 | Mercken et al. |
| 2006/0280733 A1 | 12/2006 | Kayed et al. |
| 2006/0292152 A1 | 12/2006 | Rosenthal et al. |
| 2007/0010435 A1 | 1/2007 | Frangione et al. |
| 2007/0015218 A1 | 1/2007 | Cao et al. |
| 2007/0031416 A1 | 2/2007 | Shoji et al. |
| 2007/0072307 A1 | 3/2007 | Godavarti et al. |
| 2007/0098721 A1 | 5/2007 | Hillen et al. |
| 2007/0110750 A1 | 5/2007 | Glabe et al. |
| 2007/0128191 A1 | 6/2007 | Barrio |
| 2007/0190046 A1 | 8/2007 | DeMaattos et al. |
| 2007/0213512 A1 | 9/2007 | Krafft et al. |
| 2007/0218499 A1 | 9/2007 | Lambert et al. |
| 2008/0025988 A1 | 1/2008 | Yamaguchi et al. |
| 2008/0107601 A1 | 5/2008 | Lauwereys et al. |
| 2008/0131422 A1 | 6/2008 | Sugimura et al. |
| 2008/0199879 A1 | 8/2008 | Takayama et al. |
| 2008/0292639 A1 | 11/2008 | Shen et al. |
| 2009/0023159 A1 | 1/2009 | Mendez |
| 2009/0035295 A1 | 2/2009 | Hillen et al. |
| 2009/0035307 A1 | 2/2009 | Barghorn et al. |
| 2009/0074775 A1 | 3/2009 | Holtzman et al. |
| 2009/0155246 A1 | 6/2009 | Gellerfors et al. |
| 2009/0156471 A1 | 6/2009 | Gazit et al. |
| 2009/0162362 A1 | 6/2009 | Sarasa |
| 2009/0162878 A1 | 6/2009 | Kim et al. |
| 2009/0175847 A1 | 7/2009 | Barghorn et al. |
| 2009/0191190 A1 | 7/2009 | Barghorn et al. |
| 2009/0214515 A1 | 8/2009 | Holzman et al. |
| 2009/0232801 A1 | 9/2009 | Hillen et al. |
| 2009/0238831 A1 | 9/2009 | Hillen et al. |

FOREIGN PATENT DOCUMENTS

| | | | |
|---|---|---|---|
| EP | 0613007 | | 8/1994 |
| EP | 0623675 | | 11/1994 |
| EP | 0304013 | | 6/1996 |
| EP | 0783104 | | 7/1997 |
| EP | 1130032 | | 9/2001 |
| EP | 1420032 | | 5/2004 |
| EP | 1741783 | A1 | 1/2007 |
| EP | 1861422 | | 12/2007 |
| EP | 1954718 | | 8/2008 |
| EP | 1963363 | | 9/2008 |
| EP | 1976877 | | 10/2008 |
| JP | 07238096 | | 9/1995 |
| JP | 2005 185281 | | 7/2005 |
| JP | 2007077103 | | 3/2007 |
| WO | WO 89/07657 | | 8/1989 |
| WO | WO 92/11018 | | 7/1992 |
| WO | WO 95/11994 | | 5/1995 |
| WO | WO 96/28187 | | 9/1996 |
| WO | WO 96/40731 | A | 12/1996 |
| WO | WO 97/10505 | | 3/1997 |
| WO | WO 97/18476 | | 5/1997 |
| WO | WO 99/05175 | | 2/1999 |
| WO | WO 99/27944 | | 6/1999 |
| WO | WO 99/40909 | | 8/1999 |
| WO | WO 99/59571 | | 11/1999 |
| WO | WO 00/72880 | A2 | 12/2000 |
| WO | WO 01/16364 | | 3/2001 |
| WO | WO 01/18169 | | 3/2001 |
| WO | WO 01/18169 | A | 3/2001 |
| WO | WO 01/62801 | A2 | 8/2001 |
| WO | WO 01/85093 | | 11/2001 |
| WO | WO 02/46237 | | 6/2002 |
| WO | WO 02/096937 | A2 | 12/2002 |
| WO | WO 03/014162 | | 2/2003 |
| WO | WO 03/016466 | | 2/2003 |
| WO | WO 03/070760 | A2 | 8/2003 |
| WO | WO 2004/029093 | | 4/2004 |
| WO | WO 2004/050707 | A2 * | 6/2004 |
| WO | WO 2004/058258 | A1 | 7/2004 |
| WO | WO 2004/065569 | | 8/2004 |
| WO | WO 2004/067561 | | 8/2004 |
| WO | WO 2004/071408 | A | 8/2004 |
| WO | WO 2005/005638 | | 1/2005 |

| | | |
|---|---|---|
| WO | WO 2005/018424 | 3/2005 |
| WO | WO 2005/053604 | 6/2005 |
| WO | WO 2005/081872 | 9/2005 |
| WO | WO 2005/105998 A | 11/2005 |
| WO | WO 2005/120571 | 12/2005 |
| WO | WO 2006/016644 | 2/2006 |
| WO | WO 2006/036291 | 4/2006 |
| WO | WO 2006/039327 | 4/2006 |
| WO | WO 2006/055178 A2 | 5/2006 |
| WO | WO 2006/066049 | 6/2006 |
| WO | WO 2006/066171 | 6/2006 |
| WO | WO 2006/066171 A1 | 6/2006 |
| WO | WO 2006/083533 | 8/2006 |
| WO | WO 2006/094724 | 9/2006 |
| WO | WO 2006/103116 | 10/2006 |
| WO | WO 2006/121656 | 11/2006 |
| WO | WO 2007/011639 | 1/2007 |
| WO | WO 2007/017686 | 2/2007 |
| WO | WO 2007/022416 | 2/2007 |
| WO | WO 2007/042261 | 4/2007 |
| WO | WO 2007/050359 | 5/2007 |
| WO | WO 2007/062088 | 5/2007 |
| WO | WO 2007/062852 | 6/2007 |
| WO | WO 2007/064917 | 6/2007 |
| WO | WO 2007/064919 | 6/2007 |
| WO | WO 2007/064972 | 6/2007 |
| WO | WO 2007/064972 A2 * | 6/2007 |
| WO | WO 2007/068412 | 6/2007 |
| WO | WO 2007/068412 A2 | 6/2007 |
| WO | WO 2007/068429 | 6/2007 |
| WO | WO 2007/106617 | 9/2007 |
| WO | WO 2007/108756 | 9/2007 |
| WO | WO 2007/113172 | 10/2007 |
| WO | WO 2007/123345 | 11/2007 |
| WO | WO 2008/002893 | 1/2008 |
| WO | WO 2008/011348 | 1/2008 |
| WO | WO 2008/011348 A2 | 1/2008 |
| WO | WO 2008/012101 | 1/2008 |
| WO | WO 2008/030251 | 3/2008 |
| WO | WO 2008/045962 | 4/2008 |
| WO | WO 2008/060364 | 5/2008 |
| WO | WO 2008/060364 A2 | 5/2008 |
| WO | WO 2008/061795 | 5/2008 |
| WO | WO 2008/067464 | 6/2008 |
| WO | WO 2008/070229 | 6/2008 |
| WO | WO 2008/071394 | 6/2008 |
| WO | WO 2008/104385 | 9/2008 |
| WO | WO 2008/104386 | 9/2008 |
| WO | WO 2008/110885 | 9/2008 |
| WO | WO 2008/143708 | 11/2008 |
| WO | WO 2008/150946 | 12/2008 |
| WO | WO 2008/150949 | 12/2008 |
| WO | WO 2008/156621 | 12/2008 |
| WO | WO 2008/156622 | 12/2008 |
| WO | WO 2009/048537 | 4/2009 |
| WO | WO 2009/048538 | 4/2009 |
| WO | WO 2009/048539 | 4/2009 |

OTHER PUBLICATIONS

Padlan EA et al. Structure of an antibody-antigen complex: Crystal structure of the HyHEL-10 Fab-lysozyme complex. Proc Natl Acad Sci USA, 1989; 86:5938-5942.*
Rudikoff S et al. Single amino acid substitution altering antigen-binding specificity. Proc Natl Acad Sci USA, 1982; 79(6):1979-1983.*
Anderson et al., "Characterization of β amyloid assemblies in drusen: the deposits associated with aging and age-related macular degeneration", *Experimental Eye Research*, vol. 78, (2004), pp. 243-256.
Bard et al., "Peripherally administered antibodies against amyloid bipeptide enter the central nervous system and reduce pathology in a mouse model of Alzheimer disease", *Nature Med.*, vol. 6, (2000), pp. 916-919.
Barghorn et al., "Globular amyloid beta-peptide oligomer—a homogenous and stable neuropathological protein in Alzheimer's disease", *Jour. Neurochem.*, vol. 95, (2005), pp. 834-847.
Database EMBL [Online], "Mouse immunoglobulin rearranged kappa-chain V-region V105 gene from , C.AL20-TEPC-105 myeloma, exons 1 and 2.", (Jul. 16, 1988), Database accession No. M12183.
Database Geneseq [Online], "L chain subunit of Fas specific antibody coding sequence.", (Apr. 15, 1998), Database accession No. AAT88870.
Database EMBL [Online], "Mus musculus F5.20G3 low-affinity anti-phosphorylcholine IgG antibody mRNA, partial cds.", (Feb. 8, 1999), Database accession No. AF044238.
Database Geneseq [Online], "Mouse DNA encoding antibody 3D8 heavy chain variable region.", (Apr. 22, 2003), Database accession No. ABX16569.
Demattos etal., "Peripheral anti-Aβ antibody alters CNS and plasma Aβ clearance and decreases brain Aβ burden in a mouse model of Alzheimer's disease", PNAS, vol. 98, (2001), pp. 8850-8855.
Klein, WL., "Abeta toxicity in Alzheimer's disease: globular oligomers (ADDLs) as new vaccine and drug. targets", *Neurochem. Int.*, vol. 41 No. 5, (2002), pp. 345-352.
Levine, H. III, "4, 4'-dianilino-1, 1'-binaphthyl-5'-disulfonate (bis-ANS) Reports on Non-β-Sheet Conformers of Alzheimer's Peptide β (1-40)", *Arch. Biochem. Biophys.*, vol. 404, (2002), pp. 106-115.
Liu et al., "Single chain variable fragments against beta-amyloid (Abeta) can inhibit Abeta aggregation and prevent Abeta-induced neurotoxicity", *Biochemistry*, vol. 43, (May, 2004), pp. 6959-6967.
Nicolau et al., "A liposome-based therapeutic vaccine against β-amyloid plaques on the pancreas of transgenic NORBA mice", *PNAS*, vol. 99 No. 4, (2002), pp. 2332-2337.
Rzepecki etal., "Prevention of Alzheimer's Disease-associated Aβ Aggregation by Rationally Designed. Nonpeptide β-Sheet Ligands", J. Biol. Chem., vol. 279 Issue 46, (2004), pp. 47497-47505.
Schenk et al., "Immunization with amyloid-β attenuates Alzheimer-disease-like pathology in the PDAPP mouse", *Nature*, vol. 400, (Jul., 1999), pp. 173-177.
Solomon et al., "Monoclonal antibodies inhibit in vitro fibrillar aggregation of the Alzheimer beta-amyloid peptide", *PNAS*, vol. 93, (Jan., 1996), pp. 452-455.
International Search Report for International Application No. PCT/EP2006/011862; mailed Jun. 12, 2007; (6 pgs.).
Bard et al., "Epitope and isotype specificities of antibodies to B-amyloid peptide for protection against Alzheimer's disease-like neuropathology," *PNAS*, Feb. 18, 2003, vol. 100, No. 4; pp. 2023-2028.
Database Geneseq [Online] Jan. 18, 1999, "Anti-human Fas monoclonal antibody CH11 light chain cDNA." retrieved from EBI accession No. GSN:AAV66736 Database accession No. AAV66736.
U.S. Appl. No. 12/138,372, filed Jun. 12, 2008, Pfeifer et al.
U.S. Appl. No. 11/777,777, filed Jul. 13, 2007, Pfeifer et al.
Acha-Orbea et al., 1993, "Anti-T-cell receptor V beta antibodies in autoimmunity", Immunol Ser; 59:193-202.
Celli et al., 1998, "Origin and pathogenesis of antiphospholipid antibodies", Braz J Med Biol Res; 31(6):723-732.
David et al., 1991, "A significant reduction in the incidence of collagen induced arthritis in mice treated with anti-TCRV-beta antibodies", J Cell Biochem; p. 179.
De Giorgi et al., 1993, "Induction of foetal lethality in AKR offspring after repeated inoculations into AKR females of anti-TCR/V beta 6 monoclonal antibody", Res Immunol; 144(4):245-255.
De Giorgi et al., 1993, "Murine hybridomas secreting monoclonal antibodies reacting with MIsa antigens", Exp Clin Immunogenet; I0(4):219-223.
Dorronsoro et al., 2003, "Peripheral and dual binding site inhibitors of acetylcholinesterase as neurodegenerative disease-modifying agents", Expert Opin Ther Pat; 13(11):1725-1732.
Frenkel et al., 2000, "Modulation of Alzheimer's beta-amyloid neurotoxicity by site-directed single-chain antibody", J Neuroimmunol; 106(1-2):23-31.
Fukuchi et al., 2006, "Amelioration of amyloid load by anti-Abeta single-chain antibody in Alzheimer mouse model", Biochem Biophys Res Commun; 344(1):79-86.

Kim et al., 2004, "Development of conformation-specific antibodies for neutralization of beta-amyloid oligomers", Neurobiol Aging; 25(1):S145, P1-175 Abstract.

Kisilevsky et al., 1995, "Arresting amyloidosis in vivo using small-molecule anionic sulphonates or sulphates: Implications for Alzheimer's disease", Nat Med; 1(2):143-148.

Kisilevsky, 1996, "Anti-amyloid drugs potential in the treatment of diseases associated with aging", Drugs Aging; 8(2):75-83.

Lambert et al., 2007, "Monoclonal antibodies that target pathological assemblies of Abeta", J Neurochem; 100(1): 23-35.

Lee et al., 2002, "Molecular cloning of agonistic and antagonistic monoclonal antibodies against human 4-IBB", Eur J Immunogenet; 29(5):449-452.

Lund et al., 1995, "Oligosaccaride-protein interactions in IgG can modulate recognition by Fc-gamma receptors", FASEB J; 9(1):115-119.

Moretto et al., 2007, "Conformation-sensitive antibodies against Alzheimer amyloid-beta by immunization with a thioredoxin-constrained B-cell epitope peptide", J Biol Chem; 282(15):11436-11445.

Mclaurin et al., 2002, "Therapeutically effective antibodies against amyloid-beta peptide target amyloid-beta residues 4-10 and inhibit cytotoxicity and fibrillogenesis", Nat Med; 8(11):1263-1269.

Schenk et al., 1999, "Immunization with amyloid-beta attenuates Alzheimer-disease-like pathology in the PDAPP mouse", Nature; 400:173-177.

Van Gool et al., 1994, "Concentrations of amyloid-beta protein in cerebrospinal fluid increase with age in patients free from neurodegenerative disease", Neurosci Let; 172(1-2):122-124.

Database Geneseq [Online], 2005, "Humanized monoclonal antibody Hu4785-2 heavy chain", retrieved from EBI accession No. GSP:ADX39139 Database accession No. ADX39139.

Database Geneseq [Online], 2005, "Mouse monoclonal antibody 4785 heavy chain SEQ ID 38", retrieved from EBI accession No. GSP:ADX39137 Database accession No. ADX39137.

Database Geneseq [Online], 2005, "Humanized monoclonal antibody Hu4785-2 VH region", retrieved from EBI accession No. GSP:ADX39143 Database accession No. ADX39143.

Database Geneseq [Online], 2005, "Mouse monoclonal antibody 4785 heavy chain SEQ ID I", retrieved from EBI accession No. GSP:ADX39100 Database accession No. ADX39100.

Database Geneseq [Online], 2005, "Humanized monoclonal antibody Hu4785-2 partial protein", retrieved from EBI accession no. GSP:ADX39104 Database accession No. ADX39104.

Database Ncbi Protein [Online] dated Aug. 30, 1993, accession No. AAA38584.

Database Ncbi Protein [Online] dated Mar. 23, 2002, accession No. AAL92941.

Database NCBI Protein [Online] dated Apr. 11, 1996, accession No. AAA96779.

Database NCBI Protein [Online] dated Mar. 23, 2002, accession no. AAA92933.

Barghorn et al., 2005, "Globular amyloid beta-peptide 1-42 oligomer—a homogeneous and stable neuropatholgical protein in Alzheimer's disease", J Neurochem; 95(3I):834-847.

Campbell et al., 1984, "General properties and applications of monoclonal antibodies", Elsevier Science Publishers B.V., pp. 1-32.

Fujimuro et al., 1994, "Production and characterization of monoclonal antibodies specific to multi-ubiquitin chains of polyubiquitinated proteins", FEBS; 349:173-180.

Fujimuro et al., 2005, "Production of antipolyubiquitin monoclonal antibodies and their use for characterization and isolation of polyubiquitinated proteins", Meth Enzymol; 399:75-86.

Hicke, 2001, "Protein regulation by monoubiquitin", Nat Rev; 2:196-201.

Nemes et al., 2004, "Cross-linking of ubiquitin, HSP27, parkin, and α-synuclein by γ-glutamyl-ε-lysine bonds in Alzheimer's neurofibrillary tangles", FASEB J; 18:1135-37.

Solomon et al., 1997, "Disaggregation of Alzheimer β-amyloid by site-directed mAb", Proc Natl Acad Sci USA; 94:4109-4112.

Tenno et al., 1994, "Structural basis for distinct roles of Lys63- and Lys48-linked polyubiquitin chains", Genes to Cells; 9:865-875.

U.S. Appl. No. 11/777,777, filed Jul. 13, 2007, Pfeifer.
U.S. Appl. No. 12/138,372, filed Jun. 12, 2008, Pfeifer.
U.S. Appl. No. 12/213,006, filed Jun. 12, 2008, Pfeifer.
U.S. Appl. No. 12/213,007, filed Jun. 12, 2008, Pfeifer.
U.S. Appl. No. 12/460,747, filed Jul. 23, 2009, Pfeifer.

Ding et al., 2007, "Targeting age-related macular degeneration with Alzheimer's disease based immunotherapies: anti-amyloid-beta antibody attenuates pathologies in an age-related macular degeneration mouse model", Vision Research, Pergamon Press, Oxford, GB; 48(3):339-345.

Guo et al., 2007, "Targeting amyloid-beta in glaucoma treatment", Proc Natl Acad Sci USA; 104(33):13444-13449.

Langdon et al., 2000, "Germline sequences of VH7183 gene family members in C57BL/6 mice demonstrate natural selection of particular sequences during recent evolution", Immunogen; 51:241-245.

Schable et al., 1999, "Characteristics of the immunoglobulin V kappa genes, pseudogenes, relics and orphons in the mouse genome", Eur J Immunol; 29:2082-2086.

Weaver-Feldhaus et al., 2004, "Yeast mating for combinatorial Fab library generation and surface display", FEBS Letters; 564(2):24-34.

Office Action of U.S. Appl. No. 11/777,777, dated Aug. 10, 2009.

Mckinnon et al., 2002, "Caspase activation and amyloid precursor protein cleavage in rat ocular hypertension," Investigative Ophthalmology & Visual Science 43(4):1077-1087.

International Search Report for PCT/EP2006/011862.
Written Opinion for PCT/EP2006/011862.
International Preliminary Report on Patentability PCT/EP2006/011862.
International Search Report for PCT/US2008/007318.
Written Opinion for PCT/US2008/007318.
International Preliminary Report on Patentability PCT/US2008/007318.
International Search Report for PCT/US2008/11492.
Written Opinion for PCT/US2008/11492.
International Search Report for PCT/US2007/021134.
Written Opinion for PCT/US2007/021134.
International Preliminary Report on Patentability PCT/US2007/021134.
International Search Report for PCT/US2007/073504.
Written Opinion for PCT/US2007/073504.
International Preliminary Report on Patentability PCT/US2007/073504.
International Search Report for PCT/US2008/11491.
Written Opinion for PCT/US2008/11491.
International Search Report for PCT/US2008/007317.
Written Opinion for PCT/US2008/007317.
International Preliminary Report on Patentability PCT/US2008/007317.
International Search Report for PCT/US2008/11493.
Written Opinion for PCT/US2008/11493.

* cited by examiner

Aβ 1-15 (ACI-24)

H₂N-Lys-Lys-Asp(OtBu)-Ala-Glu(OtBu)-Phe-Arg(Pbf)-His(Trt)-Asp(OtBu)-Ser(tBu)-Gly-Tyr(tBu)-Glu(OtBu)-Val-His(Trt)-His(Trt)-Gln(Trt)- Lys-Lys-OH

Aβ 1-16 (ACI-01)

Ac-Lys-Asp(OtBu)-Ala-Glu(OtBu)-Phe-Arg(Pbf)-His(Trt)-Asp(OtBu)-Ser(tBu)-Gly-Tyr(tBu)-Glu(OtBu)-Val-His(Trt)-His(Trt)-Gln(Trt)-Lys(Boc)-Lys-Gly-OH

Aβ 1-16(Δ14) (ACI-02)

Ac-Lys-Asp(OtBu)-Ala-Glu(OtBu)-Phe-Arg(Pbf)-His(Trt)-Asp(OtBu)-Ser(tBu)-Gly-Tyr(tBu)-Glu(OtBu)-Val-His(Trt)-Gln(Trt)-Lys(Boc)-Lys-Gly-OH

Aβ 22-35 (ACI-11)

Ac-Lys-Glu(OtBu)-Asp(OtBu)-Val-Gly-Ser(tBu)-Asn(Trt)-Lys(Boc)-Gly-Ala-Ile-Ile-Gly-Leu-Met-Lys-Gly-OH

Aβ 29-40 (ACI-12)

Ac-Lys-Gly-Ala-Ile-Ile-Gly-Leu-Met-Val-Gly-Gly-Val-Val-Lys-Gly-OH

FIG 1

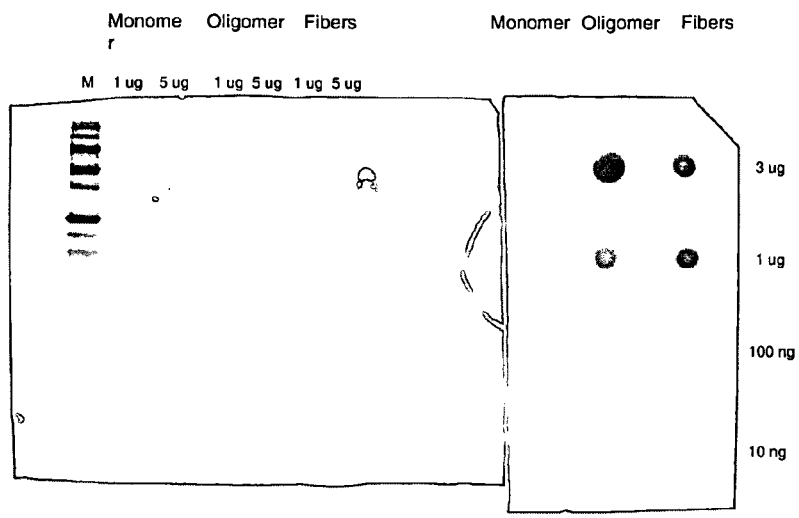
Fig 2a
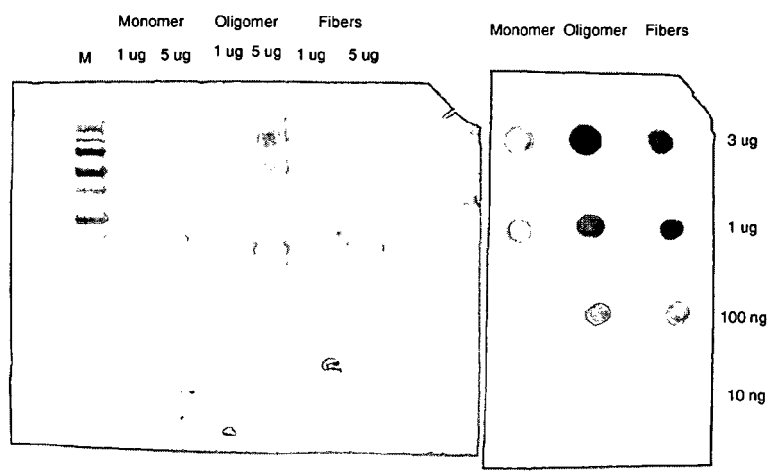
Fig 2b
FIG. 2

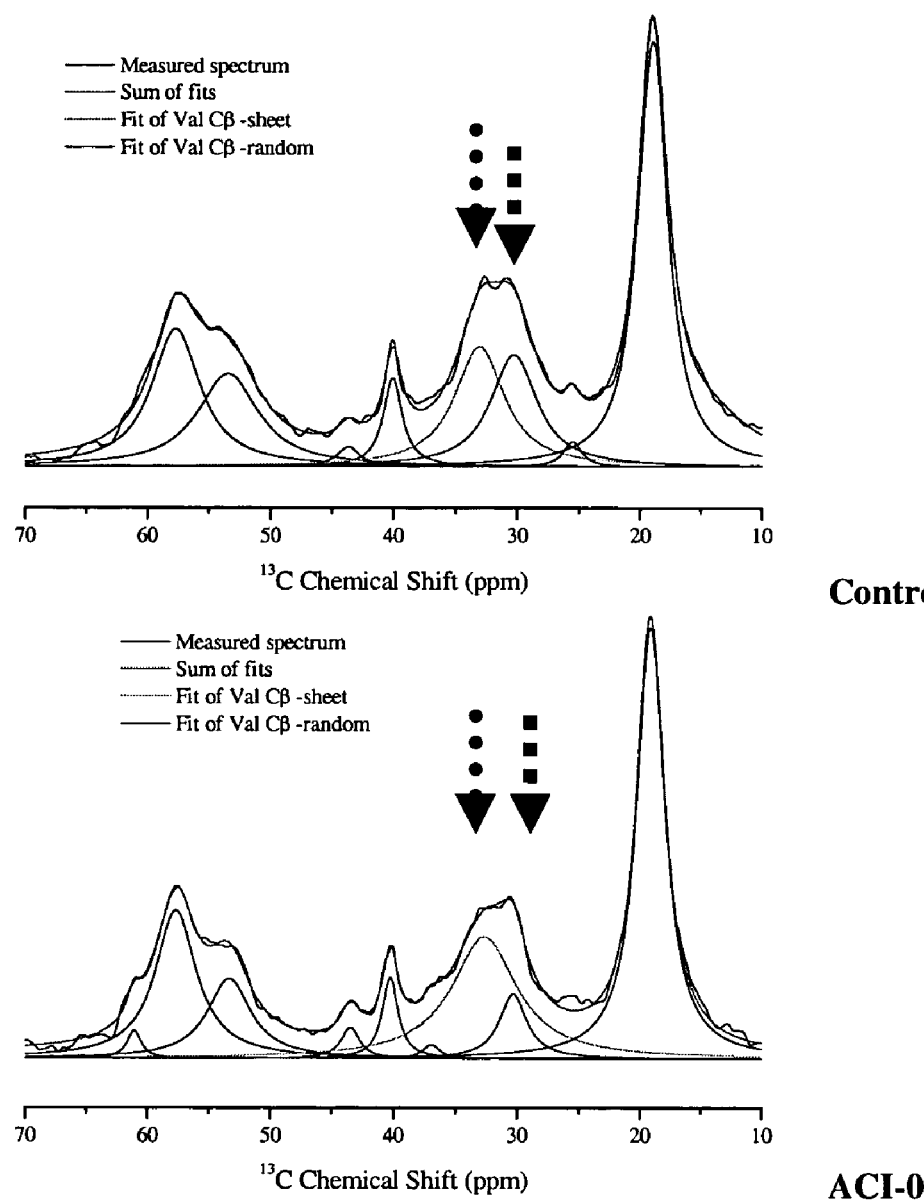
FIG: 4

MONOCLONAL ANTIBODIES THAT RECOGNIZE EPITOPES OF AMYLOID-BETA

CLAIM OF BENEFIT UNDER 35 U.S.C. 119

This application claims the benefit of European Patent Convention Application No. 05027092.5, filed Dec. 12, 2005, and European Patent Convention Application No. 06014729.5, filed Jul. 14, 2006, and European Convention Patent Application No. 06020766.9, filed Oct. 2, 2006, each of which is incorporated herein by reference in their entirety.

FIELD OF THE INVENTION

The present invention is related to methods and compositions for the therapeutic and diagnostic use in the treatment of diseases and disorders which are caused by or associated with amyloid or amyloid-like proteins including amyloidosis, a group of disorders and abnormalities associated with amyloid protein such as Alzheimer's disease.

BACKGROUND OF THE INVENTION

Amyloidosis is not a single disease entity but rather a diverse group of progressive disease processes characterized by extracellular tissue deposits of a waxy, starch-like protein called amyloid, which accumulates in one or more organs or body systems. As the amyloid deposits build up, they begin to interfere with the normal function of the organ or body system. There are at least 15 different types of amyloidosis. The major forms are primary amyloidosis without known antecedent, secondary amyloidosis following some other condition, and hereditary amyloidosis.

Secondary amyloidosis occurs in people who have a chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease, and leprosy.

Amyloid deposits typically contain three components. Amyloid protein fibrils, which account for about 90% of the amyloid material, comprise one of several different types of proteins. These proteins are capable of folding into so-called "beta-pleated" sheet fibrils, a unique protein configuration which exhibits binding sites for Congo red resulting in the unique staining properties of the amyloid protein. In addition, amyloid deposits are closely associated with the amyloid P (pentagonal) component (AP), a glycoprotein related to normal serum amyloid P (SAP), and with sulfated glycosaminoglycans (GAG), complex carbohydrates of connective tissue.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetis; senile cardiac amyloidosis; endocrine tumors, and others, including macular degeneration.

Although pathogenesis of these diseases may be diverse, their characteristic deposits often contain many shared molecular constituents. To a significant degree, this may be attributable to the local activation of pro-inflammatory pathways thereby leading to the concurrent deposition of activated complement components, acute phase reactants, immune modulators, and other inflammatory mediators (McGeer et al., 1994).

Alzheimer's Disease (AD) is a neurological disorder primarily thought to be caused by amyloid plaques, an accumulation of abnormal deposit of proteins in the brain. The most frequent type of amyloid found in the brain of affected individuals is composed primarily of Aβ fibrils. Scientific evidence demonstrates that an increase in the production and accumulation of beta-amyloid protein in plaques leads to nerve cell death, which contributes to the development and progression of AD. Loss of nerve cells in strategic brain areas, in turn, causes reduction in the neurotransmitters and impairment of memory. The proteins principally responsible for the plaque build up include amyloid precursor protein (APP) and two presenilins (presenilin I and presenilin II). Sequential cleavage of the amyloid precursor protein (APP), which is constitutively expressed and catabolized in most cells, by the enzymes β and γ secretase leads to the release of a 39 to 43 amino acid Aβ peptide. The degradation of APPs likely increases their propensity to aggregate in plaques. It is especially the Aβ(1-42) fragment that has a high propensity of building aggregates due to two very hydrophobic amino acid residues at its C-terminus. The Aβ(1-42) fragment is therefore believed to be mainly involved and responsible for the initiation of neuritic plaque formation in AD and to have, therefore, a high pathological potential. There is therefore a need for specific antibodies that can target and diffuse amyloid plaque formation.

The symptoms of AD manifest slowly and the first symptom may only be mild forgetfulness. In this stage, individuals may forget recent events, activities, the names of familiar people or things and may not be able to solve simple math problems. As the disease progresses, symptoms are more easily noticed and become serious enough to cause people with AD or their family members to seek medical help. Midstage symptoms of AD include forgetting how to do simple tasks such as grooming, and problems develop with speaking, understanding, reading, or writing. Later stage AD patients may become anxious or aggressive, may wander away from home and ultimately need total care.

Presently, the only definite way to diagnose AD is to identify plaques and tangles in brain tissue in an autopsy after death of the individual. Therefore, doctors can only make a diagnosis of "possible" or "probable" AD while the person is still alive. Using current methods, physicians can diagnose AD correctly up to 90 percent of the time using several tools to diagnose "probable" AD. Physicians ask questions about the person's general health, past medical problems, and the history of any difficulties the person has carrying out daily activities. Behavioral tests of memory, problem solving, attention, counting, and language provide information on cognitive degeneration and medical tests such as tests of blood, urine, or spinal fluid, and brain scans can provide some further information.

The management of AD consists of medication-based and non-medication based treatments. Treatments aimed at changing the underlying course of the disease (delaying or reversing the progression) have so far been largely unsuccessful. Medicines that restore the deficit (defect), or malfunctioning, in the chemical messengers of the nerve cells (neurotransmitters), in particular the cholinesterase inhibitors (ChEIs) such as tacrine and rivastigmine, have been shown to improve symptoms. ChEIs impede the enzymatic degradation of neurotransmitters thereby increasing the amount of chemical messengers available to transmit the nerve signals in the brain.

For some people in the early and middle stages of the disease, the drugs tacrine (COGNEX®, Morris Plains, N.J.), donepezil (ARICEPT®, Tokyo, JP), rivastigmine (EXELON®, East Hanover, N.J.), or galantamine (REMINYL®, New Brunswick, N.J.) may help prevent some symptoms from becoming worse for a limited time. Another drug, memantine (NAMENDA®, New York, N.Y.), has been approved for treatment of moderate to severe AD. Medications are also available to address the psychiatric manifestations of AD. Also, some medicines may help control behavioral symptoms of AD such as sleeplessness, agitation, wandering, anxiety, and depression. Treating these symptoms often makes patients more comfortable and makes their care easier for caregivers. Unfortunately, despite significant treatment advances showing that this class of agents is consistently better than a placebo, the disease continues to progress, and the average effect on mental functioning has only been modest. Many of the drugs used in AD medication such as, for example, ChEIs also have side effects that include gastrointestinal dysfunction, liver toxicity and weight loss.

Other diseases that are based on or associated with the accumulation and deposit of amyloid-like protein are mild cognitive impairment, Lewy body dementia (LBD), amyotrophic lateral sclerosis (ALS), inclusion-body myositis (IBM) and macular degeneration, in particular age-related macular degeneration (AMD).

Mild cognitive impairment (MCI) is a general term most commonly defined as a subtle but measurable memory disorder. A person with MCI experiences memory problems greater than normally expected with aging, but does not show other symptoms of dementia, such as impaired judgment or reasoning. MCI is a condition that frequently reflects a preclinical stage of AD.

The deposition of β-amyloid within the entorhinal cortex (EC) is believed to play a key role in the development of mild cognitive impairment (MCI) in the elderly. This is in line with the observation that the CSF-A Aβ(1-42) levels decline significantly once AD becomes clinically overt. In contrast to CSF-Aβ(1-42) CSF-tau levels are significantly increased in the MCI stage, and these values continue to be elevated thereafter, indicating that increased levels of CSF-tau may help in detecting MCI subjects who are predicted to develop AD.

Lewy body dementia (LBD) is a neurodegenerative disorder that can occur in persons older than 65 years of age, which typically causes symptoms of cognitive (thinking) impairment and abnormal behavioral changes. Symptoms can include cognitive impairment, neurological signs, sleep disorder, and autonomic failure. Cognitive impairment is the presenting feature of LBD in most cases. Patients have recurrent episodes of confusion that progressively worsen. The fluctuation in cognitive ability is often associated with shifting degrees of attention and alertness. Cognitive impairment and fluctuations of thinking may vary over minutes, hours, or days.

Lewy bodies are formed from phosphorylated and non-phosphorylated neurofilament proteins; they contain the synaptic protein alpha-synuclein as well as ubiquitin, which is involved in the elimination of damaged or abnormal proteins. In addition to Lewy Bodies, Lewy neurites, which are inclusion bodies in the cell processes of the nerve cells, may also be present. Amyloid plaques may form in the brains of patients afflicted with DLB, however they tend to be fewer in number than seen in patients with Alzheimer's disease. Neurofibrillary tangles, the other micropathological hallmark of AD, are not a main characteristic of DLB but are frequently present in addition to amyloid plaques.

Amyotrophic lateral sclerosis (ALS) is characterized by degeneration of upper and lower motor neurons. In some ALS patients, dementia or aphasia may be present (ALS-D). The dementia is most commonly a frontotemporal dementia (FTD), and many of these cases have ubiquitin-positive, tau-negative inclusions in neurons of the dentate gyrus and superficial layers of the frontal and temporal lobes.

Inclusion-body myositis (IBM) is a crippling disease usually found in people over age 50, in which muscle fibers develop inflammation and begin to atrophy—but in which the brain is spared and patients retain their full intellect. Two enzymes involved in the production of amyloid-β protein were found to be increased inside the muscle cells of patients with this most common, progressive muscle disease of older people, in which amyloid-β is also increased.

Another disease that is based on or associated with the accumulation and deposit of amyloid-like protein is macular degeneration.

Macular degeneration is a common eye disease that causes deterioration of the macula, which is the central area of the retina (the paper-thin tissue at the back of the eye where light-sensitive cells send visual signals to the brain). Sharp, clear, 'straight ahead' vision is processed by the macula. Damage to the macula results in the development of blind spots and blurred or distorted vision. Age-related macular degeneration (AMD) is a major cause of visual impairment in the United States and for people over age 65 it is the leading cause of legal blindness among Caucasians. Approximately 1.8 million Americans age 40 and older have advanced AMD, and another 7.3 million people with intermediate AMD are at substantial risk for vision loss. The government estimates that by 2020 there will be 2.9 million people with advanced AMD. Victims of AMD are often surprised and frustrated to find out how little is known about the causes and treatment of this blinding condition.

There are two forms of macular degeneration: dry macular degeneration and wet macular degeneration. The dry form, in which the cells of the macula slowly begin to break down, is diagnosed in 85 percent of macular degeneration cases. Both eyes are usually affected by dry AMD, although one eye can lose vision while the other eye remains unaffected. Drusen, which are yellow deposits under the retina, are common early signs of dry AMD. The risk of developing advanced dry AMD or wet AMD increases as the number or size of the drusen increases. It is possible for dry AMD to advance and cause loss of vision without turning into the wet form of the disease; however, it is also possible for early-stage dry AMD to suddenly change into the wet form.

The wet form, although it only accounts for 15 percent of the cases, results in 90 percent of the blindness, and is considered advanced AMD (there is no early or intermediate stage of wet AMD). Wet AMD is always preceded by the dry form of the disease. As the dry form worsens, some people begin to have abnormal blood vessels growing behind the macula. These vessels are very fragile and will leak fluid and blood (hence 'wet' macular degeneration), causing rapid damage to the macula.

The dry form of AMD will initially often cause slightly blurred vision. The center of vision in particular may then become blurred and this region grows larger as the disease progresses. No symptoms may be noticed if only one eye is affected. In wet AMD, straight lines may appear wavy and central vision loss can occur rapidly.

Diagnosis of macular degeneration typically involves a dilated eye exam, visual acuity test, and a viewing of the back of the eye using a procedure called fundoscopy to help diagnose AMD, and—if wet AMD is suspected—fluorescein angiography may also be performed. If dry AMD reaches the advanced stages, there is no current treatment to prevent vision loss. However, a specific high dose formula of antioxidants and zinc may delay or prevent intermediate AMD from progressing to the advanced stage. Macugen® (pegaptanib sodium injection), laser photocoagulation and photodynamic therapy can control the abnormal blood vessel growth and bleeding in the macula, which is helpful for some people who have wet AMD; however, vision that is already lost will not be restored by these techniques. If vision is already lost, low vision aids exist that can help improve the quality of life.

One of the earliest signs of age-related macular degeneration (AMD) is the accumulation of extracellular deposits known as drusen between the basal lamina of the retinal pigmented epithelium (RPE) and Bruch's membrane (BM). Recent studies conducted by Anderson et al. have confirmed that drusen contains amyloid beta. (Experimental Eye Research 78 (2004) 243-256).

Ongoing research continues with studies exploring environmental, genetic, and dietary factors that may contribute to AMD. New treatment strategies are also being explored, including retinal cell transplants, drugs that will prevent or slow down the progress of the disease, radiation therapy, gene therapies, a computer chip implanted in the retina that may help stimulate vision and agents that will prevent the growth of new blood vessels under the macula.

An important factor to consider when developing new drugs is the ease of use for the target patients. Oral drug delivery—specifically tablets, capsules and softgels—account for 70% of all dosage forms consumed because of patient convenience. Drug developers agree that patients prefer oral delivery rather than subjecting themselves to injections or other, more invasive forms of medicinal administration. Formulations resulting in low dosing intervals (i.e. once a day or sustained release) are also preferable. The ease of administering antibiotics in oral dosage forms results in an increase of patient compliance during treatment.

What is needed are effective methods and compositions for the generation of highly specific and highly effective antibodies, which is a prerequisite if the antibodies are to be provided in an oral dosage form. Preferably such antibodies would recognize specific epitopes on various antigens such as amyloid protein.

What is also needed therefore, are effective compositions and methods for addressing the complications associated with diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetis; senile cardiac amyloidosis; endocrine tumors, and others, including macular degeneration. In particular what is need are specialized and highly effective antibodies capable of counteracting the physiological manifestations of the disease such as the formation of plaques associated with aggregation of fibers of the amyloid or amyloid-like peptide.

SUMMARY OF THE INVENTION

Anti-amyloid antibodies elicited by the inoculation of $A\beta_{1-42}$ mixed with Freund complete or incomplete adjuvant had proved capable to reduce the amyloid burden in transgenic mice for human Alzheimer disease (Schenk et al., 1999).

Intraperitoneal inoculation of tetrapalmitoylated $A\beta_{1-16}$ reconstituted in liposomes to NORBA transgenic mice elicited significant titers of anti-amyloid antibodies, which also proved capable to solubilize amyloid fibers and plaques in vitro and in vivo. (Nicolau et al., 2002).

A possible mechanism by which the dissolution of amyloid plaques and fibres occurred was first suggested by Bard et al., (2000), who advanced the conclusion, based upon their data, that the antibodies opsonized the plaques, which were subsequently destroyed by the macrophages of the microglia. De Mattos et al., (2001) indicated that a MAb directed against the central domain of β-amyloid was able to bind and completely sequester plasma amyloid. They argued that the presence of these mAbs in circulation shifted the equilibrium of Aβ between brain and plasma, favoring the peripheral clearing and catabolism instead of deposition within the brain.

The present invention provides novel methods and compositions comprising highly specific and highly effective antibodies having the ability to specifically recognize and bind to specific epitopes from a range of β-amyloid antigens. The antibodies enabled by the teaching of the present invention are particularly useful for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, hereditary cerebral hemorrhage with amyloidosis Dutch type, Parkinson's disease, HIV-related dementia, ALS (amyotropic lateral sclerosis), inclusion-body myositis (IBM), Adult Onset Diabetis; senile cardiac amyloidosis; endocrine tumors, and others, including macular degeneration, to name just a few.

Moreover, the present invention provides novel methods and compositions for retaining or increasing the cognitive memory capacity in a mammal exhibiting an amyloid-associated disease or condition comprising administering to an animal, particularly a mammal, more particularly a human in need of such a treatment, a therapeutically effective amount of a monoclonal antibody according to the invention.

BRIEF DESCRIPTION OF FIGURES AND SEQUENCES

FIG. 1: Peptides derived from the Aβ sequences 1-15, 1-16 and 1-16(Δ14), 22-35, and 29-40 (SEQ ID NOs: 1-5, respectively).

FIG. 2: Binding of mACI-01-Ab7 C2 monoclonal antibody to amyloid species in Western blot and Dot blot.

FIG. 3: Binding of mACI-01-Ab7 C2 monoclonal antibody to amyloid fibers by transmission electronic microscopy.

FIG. 4: Results of a head-to-head-experiment between Th-T fluorescent assay and solid-state NMR of U-$^{13}$C Tyr10 and Val12-labeled β-amyloid 1-42 peptide SEQ ID NO: 1: Antigenic peptide Aβ$_{1-15}$
SEQ ID NO: 2: Antigenic peptide Aβ$_{1-16}$
SEQ ID NO: 3: Antigenic peptide Aβ$_{1-16(\Delta14)}$
SEQ ID NO: 4: Antigenic peptide Aβ$_{22-35}$
SEQ ID NO: 5: Antigenic peptide Aβ$_{29-40}$
SEQ ID NO: 6: Antigenic peptide Aβ$_{1-17}$
SEQ ID NO: 7: Amino acid sequence of Mouse C2 Light Chain Variable Region
SEQ ID NO: 8: Amino acid sequence of Mouse C2 Heavy Chain Variable Region
SEQ ID NO: 9: Nucleotide sequence of Mouse C2 Light Chain Variable Region
SEQ ID NO: 10: Nucleotide sequence of Mouse C2 Light Chain Variable Region including signal sequences
SEQ ID NO: 11: Nucleotide sequence of Mouse C2 Heavy Chain Variable Region
SEQ ID NO: 12: Nucleotide sequence of Mouse C2 Heavy Chain Variable Region including signal sequences
SEQ ID NO: 13-20: Amino acid sequence variants of epitopic region on the Aβ peptide
SEQ ID NO: 21: Amino acid sequence of Mouse C2 Light Chain
SEQ ID NO: 22: Amino acid sequence of Mouse C2 Heavy Chain

DETAILED DESCRIPTION

The present invention makes use of antigen presentations that result in enhanced exposure and stabilization of a preferred antigen conformation, which ultimately results in antibodies with unique properties.

In one embodiment of the invention, an antibody is provided including any functionally equivalent antibody or functional parts thereof, or, more particularly, a monoclonal antibody including any functionally equivalent antibody or functional parts thereof, which has been raised against a supramolecular antigenic construct comprising an antigenic peptide corresponding to the amino acid sequence of the β-amyloid peptide, particularly of β-amyloid peptide Aβ$_{1-15}$, Aβ$_{1-16}$ and Aβ$_{1-16(\Delta14)}$, modified with a hydrophobic moiety such as, for example, palmitic acid or a hydrophilic moiety such as, for example, polyethylene glycol (PEG) or a combination of both, wherein said hydrophobic and hydrophilic moiety, respectively, is covalently bound to each of the termini of the antigenic peptide through at least one, particularly one or two amino acids such as, for example, lysine, glutamic acid and cystein or any other suitable amino acid or amino acid analogue capable of serving as a connecting device for coupling the hydrophobic and hydrophilic moiety to the peptide fragment. When a PEG is used as the hydrophilic moiety, the free PEG termini are covalently bound to phosphatidylethanolamine or any other compound suitable to function as the anchoring element, for example, to embed the antigenic construct in the bilayer of a liposome.

In another embodiment of the invention, an antibody, particularly a monoclonal antibody, including any functionally equivalent antibody or functional parts thereof is provided, which recognized the native conformation of amyloid in that it specifically binds to amyloid oligomers and fibers, but not to not linearized amyloid species.

In a further embodiment of the invention, an antibody, particularly a monoclonal antibody, including any functionally equivalent antibody or functional parts thereof according to the present invention and as described herein before, is provided which antibody or fragment binds to an Aβ monomer with a binding affinity of at least about $1\times10^{-6}$ to at least about $1\times10^{-8}$, particularly of at least about $1\times10^{-6}$ to at least about $1\times10^{-7}$, more particularly of at least about $1\times10^{-7}$ to at least about $1\times10^{-8}$, even more particularly of at least about $1\times10^{-7}$ to at least about $4\times10^{-7}$, but, preferably, does not show any significant cross-reactivity with amyloid precursor protein (APP)

In another embodiment of the invention, an antibody, particularly a monoclonal antibody, including any functionally equivalent antibody or functional parts thereof according to the present invention and as described herein before, is provided which antibody or fragment binds to an Aβ fiber, fibril or filament with a binding affinity of at least about $1\times10^{-7}$ to at least about $1\times10^{-9}$, particularly of at least about $1\times10^{-7}$ to at least about $1\times10^{-8}$, more particularly of at least about $1\times10^{-8}$ to at least about $1\times10^{-9}$, even more particularly of at least about $1\times10^{-8}$ to at least about $5\times10^{-8}$, but, preferably, does not show any significant cross-reactivity with amyloid precursor protein (APP).

In another embodiment, the antibody, particularly a monoclonal antibody, including any functionally equivalent antibody or functional parts thereof according to the present invention and as described herein before exhibits an binding affinity to an Aβ fiber, fibril or filament which is at least 5 times, particularly at least 10 times, more particularly at least 15 times, higher than the binding affinity to an Aβ monomer.

The antibodies according to the invention are capable of inhibiting, in vitro and in vivo, the aggregation of amyloidogenic monomeric peptides, specifically β-amyloid monomeric peptides such as, for example, Aβ monomeric peptides 1-39; 1-40, 1-41, 1-42, or 1-43, but especially Aβ$_{1-42}$ monomeric peptides, into high molecular polymeric amyloid fibrils or filaments.

In a specific embodiment of the invention an antibody, particularly a monoclonal antibody, including any functionally equivalent antibody or functional parts thereof, which antibody, upon co-incubation with amyloid monomeric peptides, particularly β-amyloid monomeric peptides such as, for example, Aβ monomeric peptides 1-39; 1-40, 1-41, 1-42, or 1-43, but especially Aβ$_{1-42}$ monomeric peptides, inhibits the aggregation of the Aβ monomers into high molecular polymeric fibrils.

In a further embodiment of the invention an antibody is provided, particularly a monoclonal antibody, including any functionally equivalent antibody or functional parts thereof, which antibody, upon co-incubation, particularly upon co-incubation at a molar concentration ratio of up to 1:100, more particularly at a molar concentration ratio of between 1:30 and 1:100, but especially at a molar concentration ratio of 1:100, with amyloid monomeric peptides, particularly β-amyloid monomeric peptides such as, for example, Aβ monomeric peptides 1-39; 1-40, 1-41, 1-42, or 1-43, but especially Aβ$_{1-42}$ monomeric peptides, inhibits the aggregation of the Aβ monomers into high molecular polymeric fibrils. In particular, said inhibition amounts to at least 50%, particularly to at least 65%, more particularly to at least 75%, even more particularly to at least 80%, but especially to at least 85%-90%, or more as compared to the respective amyloid peptide monomers incubated in buffer (control).

In particular, the co-incubation of the antibody according to the invention with amyloid monomeric peptides is carried out for 24 hours to 60 hours, particularly for 30 hours to 50 hours, more particularly for 48 hours at a temperature of between 28° C. and 40° C., particularly of between 32° C. and 38° C., more particularly at 37° C.

In another embodiment the present invention provides an antibody, particularly a monoclonal antibody, including any functionally equivalent antibody or functional parts thereof which antibody, upon co-incubation for 48 hours at 37° C. at a molar concentration ratio of 1:100 with an amyloid monomeric peptide, specifically a β-amyloid monomeric peptide such as, for example, Aβ monomeric peptide 1-39; 1-40, 1-41, 1-42, or 1-43, but especially a $A\beta_{1\text{-}42}$ monomeric peptide, is capable of inhibiting the aggregation of the amyloid monomers, particularly the aggregation of β-amyloid monomeric peptides such as, for example, Aβ monomeric peptides 1-39; 1-40, 1-41, 1-42, or 1-43, but especially of the $A\beta_{1\text{-}42}$ monomeric peptide into high molecular polymeric fibrils or filaments by at least 85%, particularly by at least 89% and more particularly by at least 95% as compared to the respective amyloid peptide monomers incubated in buffer (control).

In a specific embodiment, the invention provides an antibody, particularly a monoclonal antibody, including any functionally equivalent antibody or functional parts thereof, which exhibits high specificity to $A\beta_{1\text{-}42}$ monomeric peptides but shows essentially no or only minor cross-reactivity to $A\beta_{1\text{-}38}$, $A\beta_{1\text{-}39}$, $A\beta_{1\text{-}40}$, and/or $A\beta_{1\text{-}41}$ monomeric peptides, particularly an antibody, but especially a monoclonal antibody, including any functionally equivalent antibody or functional parts thereof, which antibody is up to 100 fold, particularly 50 to 100 fold, more particularly 80 to 100 fold, but especially 100 fold more sensitive to amyloid peptide $A\beta_{1\text{-}42}$ as compared to $A\beta_{1\text{-}38}$, $A\beta_{1\text{-}39}$, $A\beta_{1\text{-}40}$, $A\beta_{1\text{-}41}$ and up to 1000 fold, particularly 500 to 1000 fold, more particularly 800 to 1000 fold, but especially 1000 fold more sensitive to amyloid peptide $A\beta_{1\text{-}42}$ as compared to $A\beta_{1\text{-}38}$, and thus capable of inhibiting, in vitro and in vivo, the aggregation of amyloidogenic monomeric peptides, but especially of amyloid peptide $A\beta_{1\text{-}42}$ In another specific embodiment of the invention an antibody, particularly a monoclonal antibody, including any functionally equivalent antibody or functional parts thereof, which has a high binding sensitivity to amyloid peptide $A\beta_{1\text{-}42}$ and is capable of detecting $A\beta_{1\text{-}42}$ fibers in a concentration of down to at least 0.001 μg, but particularly in a concentration range of between 0.5 μg and 0.001 μg, more particularly between 0.1 μg and 0.001 μg, but especially in a concentration of 0.001 μg.

In a very specific embodiment of the invention an antibody is provided, particularly a monoclonal antibody, including any functionally equivalent antibody or functional parts thereof, which antibody is capable of detecting $A\beta_{1\text{-}42}$ fibers down to a minimal concentration of 0.001 μg and $A\beta_{1\text{-}40}$ fibers down to a minimal concentration of 0.1 μg and $A\beta_{1\text{-}38}$ fibers down to a minimal concentration of 1 μg amount of fibers.

Binding of the antibodies according to the invention and as described herein before to amyloidogenic monomeric peptides but, particularly, to the amyloid form (1-42) leads to inhibition of the aggregation of monomeric amyloidogenic peptides to high molecular fibrils or filaments. Through the inhibition of the aggregation of amyloidogenic monomeric peptides the antibodies according to the present invention are capable of preventing or slowing down the formation of amyloid plaques, particularly the amyloid form (1-42), which is know to become insoluble by change of secondary conformation and to be the major part of amyloid plaques in brains of diseased animals or humans.

The aggregation inhibition potential of the antibody according to the invention may be determined by any suitable method known in the art, particularly by density-gradient ultracentrifugation followed by a SDS-PAGE sedimentation analysis on a preformed gradient and/or by a thioflavin T (Th-T) fluorescent assay.

The present invention further provides antibodies which, upon co-incubation with preformed high molecular polymeric amyloid fibrils or filaments formed by the aggregation of amyloid monomeric peptides, specifically β-amyloid monomeric peptides such as, for example, Aβ monomeric peptides 1-39; 1-40, 1-41, 1-42, or 1-43, but especially $A\beta_{1\text{-}42}$ monomeric peptides, are capable of disaggregating said high molecular polymeric amyloid fibrils or filaments.

In another embodiment of the invention an antibody is provided, but especially a monoclonal antibody including any functionally equivalent antibody or functional parts thereof, which antibody, upon co-incubation at a molar concentration ratio of up to 1:100, more particularly at a molar concentration ratio of between 1:30 and 1:100, but especially at a molar concentration ratio of 1:100, with preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42, or 1-43, but especially $A\beta_{1\text{-}42}$ monomeric peptides, is capable of disaggregating the preformed polymeric fibrils or filaments by at least 35%, particularly by at least 40%, more particularly by at least 50%, even more particularly by at least 60%, but especially by at least 70% or more.

In particular, the antibody according to the invention is co-incubated with amyloid preformed high molecular polymeric amyloid fibrils or filaments for 12 hours to 36 hours, particularly for 18 hours to 30 hours, more particularly for 24 hours at a temperature of between 28° C. and 40° C., particularly of between 32° C. and 38° C., more particularly at 37° C.

In a specific embodiment the present invention provides an antibody, particularly a monoclonal antibody, including any functionally equivalent antibody or functional parts thereof, which antibody, upon co-incubation for 24 hours at 37° C. at a molar concentration ratio of 1:100 with preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42, or 1-43, but especially $A\beta_{1\text{-}42}$ monomeric peptides, is capable of disaggregating said preformed high molecular polymeric amyloid fibrils or filaments by at least 35%, particularly by at least 40%, more particularly by at least 50%, even more particularly by at least 60%, but especially by at least 70% or more as compared to the respective preformed amyloid polymeric fibrils or filaments incubated with a control vehicle (amyloid alone) (control).

The disaggregation potential of the antibody according to the invention may be determined by any suitable method known in the art, particularly by density-gradient ultracentrifugation followed by a SDS-PAGE sedimentation analysis on a preformed gradient and/or by a thioflavin T (Th-T) fluorescent assay.

The present invention further provides antibodies or functional parts thereof which are conformationally sensitive.

In a further embodiment of the invention an antibody is provided, but especially a monoclonal antibody including any functionally equivalent antibody or functional parts thereof, which antibody, upon co-incubation with preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, is capable of inducing a transition of the β-sheet conformation towards an α-helix and/or a random coil conformation, but particularly a random coil conformation, even more particularly a random coil conformation at a given location in the molecule, especially in the environment of Val12 of the Aβ protein, which leads to an increase of the random coil conformation at the expense of the β-sheet conformation and an improved solubilization of the preformed high molecular polymeric amyloid fibrils or filaments. In particular the decrease of the β-sheet conformation amounts to at least 30%, particularly to at least 35%, and more particularly to at least 40% and more as compared to the respective preformed amyloid polymeric fibrils or filaments incubated in buffer (control).

In particular, the antibody according to the invention is co-incubated with amyloid preformed high molecular polymeric amyloid fibrils or filaments for 12 hours to 36 hours, particularly for 18 hours to 30 hours, more particularly for 24 hours at a temperature of between 28° C. and 40° C., particularly of between 32° C. and 38° C., more particularly at 37° C.

In particular, the present invention provides an antibody, particularly a monoclonal antibody, including any functionally equivalent antibody or functional parts thereof, which antibody, upon co-incubation for 24 hours at 37° C. at a molar concentration ratio of 1:100 with preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, is capable of inducing a transition of the β-sheet conformation towards an α-helix and/or a random coil conformation, but particularly a random coil conformation, even more particularly a random coil conformation at a given location in the molecule, especially in the environment of Val12 of the Aβ protein, which leads to an increase of the random coil conformation at the expense of the β-sheet conformation, with the latter being reduced by at least 30%, particularly by at least 35%, and more particularly by at least 40% and more as compared to the respective preformed amyloid polymeric fibrils or filaments incubated in buffer (control).

The antibody's potential in inducing a conformational transition may be determined by any suitable method known in the art, particularly by solid state 13C NMR spectroscopy but, in particular, by measuring the integral intensities of the conformations of Val 12 Cβ in the Aβ peptide, particularly the Aβ peptides 1-39; 1-40, 1-41, 1-42, or 1-43, but especially in the $A\beta_{1-42}$ monomeric peptide.

Through the disaggregation of amyloidogenic polymeric fibrils or filaments the antibodies according to the present invention are capable of preventing or slowing down the formation of amyloid plaques, which leads to an alleviation of the symptoms associated with the disease and a delay or reversal of its progression.

Accordingly, it is a further embodiment of the invention to provide an antibody, particularly a monoclonal antibody, including any functionally equivalent antibody or functional parts thereof as described herein before, which antibody is capable of decreasing the total amount of Aβ in the brain of an animal, particularly a mammal, but especially a human suffering from a disease or condition leading to increased concentration of Aβ in the brain.

In another embodiment of the invention an antibody, particularly a monoclonal antibody, including any functionally equivalent antibody or functional parts thereof as described herein before is provided, which antibody is capable of disrupting plaques thus decreasing the plaque load in the brain of an animal, particularly a mammal, but especially a human suffering from a disease or condition leading to an increased plaque load in the brain. The antibody according to the invention including any functionally equivalent antibody or functional parts thereof decreases the plaque load in the brain by at least 20%, particularly by at least 25%, more particularly by at least 30%, even more particularly more than 30%.

In still another embodiment of the invention an antibody, particularly a monoclonal antibody, including any functionally equivalent antibody or functional parts thereof as described herein before is provided, which antibody is capable of solubilizing plaques leading to a reduction of the amount of plaques in the brain of an animal, particularly a mammal, but especially a human suffering from a disease or condition leading to an increased plaque load in the brain. The antibody according to the invention including any functionally equivalent antibody or functional parts thereof reduces the amount of plaques in the brain by at least 10%, particularly by at least 15%, more particularly by at least 20%.

It is to be understood that the antibody according to the invention can exhibit one, two or more of the specific properties described herein before in various combinations.

For example, in one embodiment, the present invention provides antibodies, but especially monoclonal antibodies including any functionally equivalent antibody or functional parts thereof, which antibodies are bifunctional in that they exhibit both an aggregation inhibition property as well as a disaggregation property as defined herein before, particularly paired with a high degree of conformational sensitivity.

In still another embodiment of the invention a bifunctional antibody is provided including any functionally equivalent antibody or functional parts thereof, but especially a bifunctional monoclonal antibody including any functionally equivalent antibody or functional parts thereof, which antibody, upon co-incubation with amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, inhibits the aggregation of the Aβ monomers into high molecular polymeric fibrils or filaments and, in addition, upon co-incubation with preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, is capable of disaggregating the preformed polymeric fibrils or filaments.

In a specific embodiment of the invention the co-incubation of the bifunctional antibody according to the invention, but especially of the bifunctional monoclonal antibody according to the invention with amyloid monomeric peptides and preformed high molecular polymeric amyloid fibrils or filaments, respectively, takes place at a molar concentration ratio of up to 1:100, particularly at a ratio of between 1:30 and 1:100, and more particularly at a ration of 1:100.

In particular, the co-incubation of the antibody according to the invention with amyloid monomeric peptides is carried out for 24 hours to 60 hours, particularly for 30 hours to 50 hours, more particularly for 48 hours at a temperature of between 28° C. and 40° C., particularly of between 32° C. and 38° C., more particularly at 37° C., whereas the co-incubation with amyloid preformed high molecular polymeric amyloid fibrils or filaments is carried out for 12 hours to 36 hours, particularly for 18 hours to 30 hours, more particularly for 24 hours at a temperature of between 28° C. and 40° C., particularly of between 32° C. and 38° C., more particularly at 37° C.

In still another specific embodiment of the invention the bifunctional antibody according to the invention, particularly the bifunctional monoclonal antibody according to the invention, including any functionally equivalent antibody or functional parts thereof, is capable of disaggregating the preformed polymeric fibrils or filaments by at least 10%, particularly by at least 25%, more particularly by at least 35%, even more particularly by at least 50%, but especially by at least 60-70% or more.

In still another specific embodiment of the invention the bifunctional antibody according to the invention, particularly the bifunctional monoclonal antibody according to the invention, including any functionally equivalent antibody or functional parts thereof, inhibits the aggregation of amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides by at least 50%, particularly by at least 65%, more particularly by at least 75%, even more particularly by at least 80%, but especially by at least 85-90%, or more as compared to the respective amyloid peptide monomers incubated in buffer (control).

In particular, the present invention provides an antibody, particularly a bifunctional antibody, but especially a monoclonal antibody, particularly a bifunctional monoclonal antibody, including any functionally equivalent antibody or functional parts thereof, which antibody mediates inhibition of polymerization of amyloid monomeric peptides, specifically β-amyloid monomeric peptides such as, for example, Aβ monomeric peptides 1-39, 1-40, 1-41, 1-42, or 1-43, but especially $A\beta_{1-42}$ monomeric peptides and/or induces solubilization of preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, through specific and direct binding of the antibody to the Aβ fibers, which leads to a transition of secondary conformation.

The present invention further provides an antibody, particularly a bifunctional antibody, but especially a monoclonal antibody, particularly a bifunctional monoclonal antibody, including any functionally equivalent antibody or functional parts thereof, which antibody directly and specifically binds to β-amyloid fibers such as, for example, fibers comprising Aβ monomeric peptides 1-39; 1-40, 1-41, 1-42, or 1-43, but especially to fibers comprising $A\beta_{1-42}$ monomeric peptides and/or induces solubilization of preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, by targeting and specifically binding to an epitope within an epitopic region of the β-amyloid protein, particularly an epitopic region of the Aβ polypeptide confined by amino acid residues $aa_n$-$aa_m$ with n being an integer between 2 and 16, particularly between 5 and 16, more particularly between 8 and 16, even more particularly between 10 and 16 and m being an integer between 3 and 25, particularly between 3 and 23, particularly between 3 and 20, particularly between 3 and 17, particularly between 6 and 17, more particularly between 9 and 17, even more particularly between 11 and 17, wherein n and m cannot be identical numbers and n must always be a smaller number than m, with the difference between n and m≧2.

In a specific embodiment of the invention, n is an integer between 13 and 15, but especially 14 and m is an integer between 22 and 24, but especially 23.

The binding of the antibody according to the invention may induce a conformational transition in said protein, particularly a transition of the α-sheet conformation towards an α-helix and/or a random coil conformation, but particularly a random coil conformation, even more particularly a random coil conformation at a given location in the molecule, particularly in the environment of Val12 of the Aβ protein.

In a further embodiment, the invention provides an antibody, particularly a monoclonal antibody, including any functionally equivalent antibody or functional parts thereof, which antibody incorporates at least one of the properties mentioned herein before and selected from the group consisting of aggregation inhibition, disaggregation, induction of conformational transition, recognition of and direct binding to an epitope, particularly a conformational discontinuous epitope in the 14-23, particularly in the 14-20 region, preventing or slowing down the formation of amyloid plaques, decreasing the total amount of soluble Aβ in the brain, decreasing the plaque load in the brain, reducing the amount of plaques in the brain, retaining or increasing cognitive memory capacity, but especially a combination of two or more of said properties.

In specific embodiment, the invention relates to an antibody, particularly a monoclonal antibody, including any functionally equivalent antibody or functional parts thereof, which antibody incorporates at least 2, particularly at least 3, more particularly at least 4, even more particularly at least 5, 6, 7 or 8, but especially all of the above mentioned properties.

In a specific embodiment, the invention provides an antibody, particularly a bifunctional antibody, but especially a monoclonal antibody, particularly a bifunctional monoclonal antibody, including any functionally equivalent antibody or functional parts thereof, which exhibits high specificity to $A\beta_{1-42}$ monomeric peptides but shows essentially no or only minor cross-reactivity to $A\beta_{1-38}$, $A\beta_{1-39}$, $A\beta_{1-40}$, and/or $A\beta_{1-41}$ monomeric peptides, particularly an antibody, but especially a monoclonal antibody, including any functionally equivalent antibody or functional parts thereof, which antibody is up to 100 fold, particularly 50 to 100 fold, more particularly 80 to 100 fold, but especially 100 fold more sensitive to amyloid peptide $A\beta_{1-42}$ as compared to $A\beta_{1-38}$, $A\beta_{1-39}$, $A\beta_{1-40}$, $A\beta_{1-41}$ and up to 1000 fold, particularly 500 to 1000 fold, more particularly 800 to 1000 fold, but especially 1000 fold more sensitive to amyloid peptide $A\beta_{1-42}$ as compared to $A\beta_{1-38}$, and thus capable of inhibiting, in vitro and in vivo, the aggregation of amyloidogenic monomeric peptides, but especially of amyloid peptide $A\beta_{1-42}$ In another specific embodiment of the invention an antibody, particularly a bifunctional antibody, but especially a monoclonal antibody, particularly a bifunctional monoclonal antibody, including any functionally equivalent antibody or functional parts thereof, which has a high binding affinity to amyloid peptide $A\beta_{1-42}$ and is capable of detecting $A\beta_{1-42}$ fibers in a concentration of down to at least 0.001 μg, but particularly in a concentration range of between 0.5 μg and 0.001 μg, more particularly between 0.1 μg and 0.001 μg, but especially in a concentration of 0.001 μg.

In a very specific embodiment of the invention an antibody is provided, particularly a bifunctional antibody, but especially a monoclonal antibody, particularly a bifunctional monoclonal antibody, including any functionally equivalent antibody or functional parts thereof, which antibody is capable of detecting $A\beta_{1-42}$ fibers down to a minimal concentration of 0.001 μg and $A\beta_{1-40}$ fibers down to a minimal concentration of 0.1 μg and $A\beta_{1-38}$ fibers down to a minimal concentration of 1 μg amount of fibers.

In one specific aspect, the invention relates to an antibody or a fragment thereof, which recognizes and binds to at least one distinct binding site, particularly to a least two distinct binding sites on the β-amyloid protein.

In a specific embodiment, the invention relates to an antibody including any functionally equivalent antibody or functional parts thereof which antibody recognizes and binds to at least one distinct binding site, particularly to at least two distinct binding sites on the β-amyloid protein wherein the said at least one or said at least two distinct binding sites comprise at least one amino acid residue and at least two consecutive amino acid residues, respectively, predominantly involved in the binding of the antibody, wherein, in a specific embodiment of the invention, the at least one residue comprising the first distinct binding site is Leu and the at least two consecutive amino acid residues, comprising the second distinct binding site, are -Phe-Phe- embedded within the following core sequence:

-Xaa1-Xaa2-Xaa3-Leu-Xaa4-Phe-Phe-Xaa5-Xaa6-Xaa7- (SEQ ID NO: 19)

wherein $Xaa_1$ is an amino acid residue selected from the group comprising His, Asn, Gln Lys, and Arg;

$Xaa_2$ is an amino acid residue selected from the group comprising Asn and Gln;

$Xaa_3$ is an amino acid residue selected from the group comprising Lys, His, Asn, Gln and Arg $Xaa_4$ is an amino acid residue selected from the group comprising Ala, Val, Leu, norleucine, Met, Phe, and Ile;

$Xaa_5$ is an amino acid residue selected from the group comprising Ala, Val, Leu, Ser and Ile;

$Xaa_6$ is an amino acid residue selected from the group comprising Glu and Asp, $Xaa_7$ is an amino acid residue selected from the group comprising Glu and Asp.

In particular, an antibody or a fragment thereof is provided, which recognizes and binds to at least one distinct binding site, particularly to a least two distinct binding sites on the β-amyloid protein wherein the said at least one or said at least two distinct binding sites comprise at least one amino acid residue and at least two consecutive amino acid residues, respectively, predominantly involved in the binding of the antibody, wherein, in a specific embodiment of the invention, the at least one residue constituting the first distinct binding site is Leu and the at least two consecutive amino acid residues, constituting the second distinct binding site, are -Phe-Phe- embedded within the following core sequence:

-Xaa1-Xaa2-Xaa3-Leu-Xaa4-Phe-Phe-Xaa5-Xaa6-Xaa7- (SEQ ID NO: 19)

wherein $Xaa_1$ is an amino acid residue selected from the group comprising His, Asn, Gln Lys, and Arg;

$Xaa_2$ is an amino acid residue selected from the group comprising Asn and Gln;

$Xaa_3$ is an amino acid residue selected from the group comprising Lys, His, Asn, Gln and Arg $Xaa_4$ is an amino acid residue selected from the group comprising Ala, Val, Leu, norleucine, Met, Phe, and Ile;

$Xaa_5$ is an amino acid residue selected from the group comprising Ala, Val, Leu, Ser and Ile;

$Xaa_6$ is an amino acid residue selected from the group comprising Glu and Asp, $Xaa_7$ is an amino acid residue selected from the group comprising Glu and Asp.

In another embodiment of the invention, an antibody or a fragment thereof is provided, wherein $Xaa_1$ is His or Arg, but particularly His;

$Xaa_2$ is Gln or Asn, but particularly Gln;

$Xaa_3$ is Lys or Arg, but particularly Lys $Xaa_4$ is Val or Leu, but particularly Val;

$Xaa_5$ is Ala or Val, but particularly Ala;

$Xaa_6$ is Glu or Asp, but particularly Glu; and $Xaa_7$ is Asp or Glu, but particularly Asp.

In another aspect, the invention relates to an antibody or a fragment thereof, which recognizes and binds to at least one distinct binding site, particularly to a least two distinct binding sites, more particularly to at least three distinct binding sites on the β-amyloid protein, wherein said one or the at least two or the at least three distinct binding sites each comprise at least one, particularly at least two consecutive amino acid residues predominantly involved in the binding of the antibody.

In particular, the antibody or a fragment thereof according to the invention binds to at least two distinct binding sites on the β-amyloid protein, wherein said at least two distinct binding sites each comprise at least two consecutive amino acid residues predominantly involved in the binding of the antibody, wherein said at least two distinct binding sites are located in close proximity to each other on the antigen, separated by at least one amino acid residue not involved in antibody binding or to a significantly smaller extent as compared to said at least two consecutive amino acid residues, thus forming a conformational discontinuous epitope.

In another embodiment of the invention, an antibody or a fragment thereof according to the invention is provided, which recognizes and binds to at least one distinct binding site, particularly to at least two distinct binding sites, more particularly to at least three distinct binding sites on the β-amyloid protein wherein said distinct binding sites comprise at least one and at least two consecutive amino acid residues, respectively, predominantly involved in the binding of the antibody, wherein the at least one and the at least two consecutive amino acids, which are separated by at least one amino acid residue not involved in antibody binding or to a significantly smaller extent as compared to the amino acid residues predominantly involved in the binding of the antibody, are -His- and -Lys-Leu-, respectively, embedded within the following core sequence:

-His-Xaa2-Lys-Leu-Xaa3-Xaa4-Xaa5-Xaa6-Xaa7-Xaa8- (SEQ ID NO: 13) wherein

Xaa2 is an amino acid residue selected from the group comprising Asn and Gln;

Xaa3 is an amino acid residue selected from the group comprising Ala, Val, Leu, norleucine, Met, Phe, and Ile;

Xaa4 is an amino acid residue selected from the group comprising Ala, Val, Leu, norleucine, Met, Phe, and Ile Xaa5 is an amino acid residue selected from the group comprising Ala, Val, Leu, norleucine, Met, Phe, and Ile Xaa6 is an amino acid residue selected from the group comprising Ala, Val, Leu, Ser and Ile;

Xaa7 is an amino acid residue selected from the group comprising Glu and Asp,

Xaa8 is an amino acid residue selected from the group comprising Glu and Asp and wherein said amino acid residues Xaa2, Xaa3, Xaa6, Xaa7, Xaa8, are not involved in antibody binding or to a significantly smaller extent as compared to the -His- and the -Lys-Leu- binding site.

In another embodiment, an antibody or a fragment thereof is provided, which recognizes and binds to at least one distinct binding site, particularly to a least two distinct binding sites, more particularly to at least three distinct binding sites on the β-amyloid protein wherein said distinct binding sites comprise at least one and at least two consecutive amino acid residues, respectively, predominantly involved in the binding of the antibody, wherein the at least two consecutive amino acid residues representing a first binding site are -Phe-Phe- and the at least one amino acid residue is -His- embedded within the following core sequence:

-Xaa1-His-Xaa3-Xaa4-Xaa5-Xaa6-Phe-Phe-Xaa7-Xaa8-Xaa9- (SEQ ID NO: 14),
wherein
Xaa$_1$ is an amino acid residue selected from the group comprising His, Asn, Gln, Lys and Arg
Xaa$_3$ is an amino acid residue selected from the group comprising Asn and Gln
Xaa$_4$ is an amino acid residue selected from the group comprising His, Asn, Gln, Lys and Arg
Xaa$_5$ is an amino acid residue selected from the group comprising Ala, Val, Leu, Ser and Ile;
Xaa$_6$ is an amino acid residue selected from the group comprising Ala, Val, Leu and Ile
Xaa$_7$ is an amino acid residue selected from the group comprising Ala, Val, Leu and Ile
Xaa$_8$ is an amino acid residue selected from the group comprising Glu and Asp,
Xaa$_9$ is an amino acid residue selected from the group comprising Glu and Asp, and wherein said amino acid residues Xaa$_1$, Xaa$_3$, Xaa$_6$, Xaa$_7$, Xaa$_8$ and Xaa$_9$, are not involved in antibody binding or to a significantly smaller extent as compared to the His and the -Phe-Phe- binding site.

In a specific embodiment of the invention, the first of at least two consecutive amino acid residues predominantly involved in the binding of the antibody involve -Lys- and -Leu-, and the second of the at least two consecutive amino acid residues involve -Phe-Phe- embedded within the following core sequence:

-Xaa1-Xaa2-Lys-Leu-Xaa4-Phe-Phe-Xaa5-Xaa6-Xaa7- (SEQ ID NO: 15),
wherein
Xaa$_1$ is an amino acid residue selected from the group comprising His, Asn, Gln Lys, and Arg;
Xaa$_2$ is an amino acid residue selected from the group comprising Asn and Gln;
Xaa$_4$ is an amino acid residue selected from the group comprising Ala, Val, Leu, norleucine, Met, Phe, and Ile;
Xaa$_5$ is an amino acid residue selected from the group comprising Ala, Val, Leu, Ser and Ile;
Xaa$_6$ is an amino acid residue selected from the group comprising Glu and Asp,
Xaa$_7$ is an amino acid residue selected from the group comprising Glu and Asp, and wherein said amino acid residues Xaa$_2$, Xaa$_3$, Xaa$_4$, Xaa$_5$, Xaa$_6$, Xaa$_7$ are not involved in antibody binding or to a significantly smaller extent as compared to the -Lys-Leu and the -Phe-Phe- binding site.

In another embodiment of the invention, an antibody or a fragment thereof is provided, wherein
Xaa$_1$ is His or Arg, but particularly His;
Xaa$_2$ is Gln or Asn, but particularly Gln;
Xaa$_4$ is Val or Leu, but particularly Val;
Xaa$_5$ is Ala or Val, but particularly Ala;
Xaa$_6$ is Glu or Asp, but particularly Glu; and
Xaa$_7$ is Asp or Glu, but particularly Asp.

In a further embodiment of the invention, the antibody or a fragment thereof according to the invention binds to at least three distinct binding sites on the β-amyloid protein wherein said at least three distinct binding sites comprise at least one amino acid residue and at least two consecutive amino acid residues, respectively, which residues are predominantly involved in the binding of the antibody, wherein said at least three distinct binding sites are located in close proximity to each other on the antigen, separated by at least one amino acid residue not involved in antibody binding or to a significantly smaller extent as compared to said at least one amino acid residue and said at least two consecutive amino acid residues, respectively, thus forming a conformational discontinuous epitope.

In a specific embodiment of the invention, the first of the at least two consecutive amino acid residues predominantly involved in the binding of the antibody involve -Lys-Leu-, and the second of the at least two consecutive amino acid residues involve -Phe-Phe-, and the third at least one amino residue involves -His- embedded within the following core sequence:

-His-Xaa2-Lys-Leu-Xaa4-Phe-Phe-Xaa5-Xaa6-Xaa7- (SEQ ID NO: 16)
wherein
Xaa$_2$ is an amino acid residue selected from the group comprising Asn and Gln;
Xaa$_4$ is an amino acid residue selected from the group comprising Ala, Val, Leu, norleucine, Met, Phe, and Ile;
Xaa$_5$ is an amino acid residue selected from the group comprising Ala, Val, Leu, Ser and Ile;
Xaa$_6$ is an amino acid residue selected from the group comprising Glu and Asp,
Xaa$_7$ is an amino acid residue selected from the group comprising Glu and Asp, and wherein said amino acid residues Xaa$_2$, Xaa$_3$, Xaa$_4$, Xaa$_5$, Xaa$_6$, Xaa$_7$ are not involved in antibody binding or to a significantly smaller extent as compared to the -His-, the -Lys-Leu, and the -Phe-Phe- binding site.

In another embodiment of the invention, an antibody or a fragment thereof is provided, wherein
Xaa$_2$ is Gln or Asn, but particularly Gln;
Xaa$_4$ is Val or Leu, but particularly Val;
Xaa$_5$ is Ala or Val, but particularly Ala;
Xaa$_6$ is Glu or Asp, but particularly Glu; and
Xaa$_7$ is Glu or Asp, but particularly Asp.

In a specific embodiment of the invention, the first of the at least two consecutive amino acid residues predominantly involved in the binding of the antibody involve -Lys-Leu-, and the second of the at least two consecutive amino acid residues involve -Phe-Phe-, and the third at least one amino residue involves -Asp- embedded within the following core sequence:

-Xaa1-Xaa2-Lys-Leu-Xaa4-Phe-Phe-Xaa5-Xaa6-Asp- (SEQ ID NO: 17)
wherein
Xaa$_1$ is an amino acid residue selected from the group comprising His, Asn, Gln Lys, and Arg;
Xaa$_2$ is an amino acid residue selected from the group comprising Asn and Gln;
Xaa$_4$ is an amino acid residue selected from the group comprising Ala, Val, Leu, norleucine, Met, Phe, and Ile;
Xaa$_5$ is an amino acid residue selected from the group comprising Ala, Val, Leu, Ser and Ile;

Xaa$_6$ is an amino acid residue selected from the group comprising Glu and Asp, and wherein said amino acid residues Xaa$_2$, Xaa$_3$, Xaa$_4$, Xaa$_5$, Xaa$_6$, Xaa$_7$ are not involved in antibody binding or to a significantly smaller extent as compared to the -Asp-, the -Lys-Leu, and the -Phe-Phe- binding site.

In another embodiment of the invention, an antibody or a fragment thereof is provided, wherein Xaa$_1$ is His or Arg, but particularly His;
Xaa$_2$ is Gln or Asn, but particularly Gln;
Xaa$_4$ is Val or Leu, but particularly Val;
Xaa$_5$ is Ala or Val, but particularly Ala; and
Xaa$_6$ is Glu or Asp, but particularly Glu In a further specific embodiment of the invention, an antibody or a fragment thereof according to the invention is provided, which binds to 4 distinct binding sites on the β-amyloid protein wherein said 4 distinct binding sites comprise one amino acid residue and two consecutive amino acid

| Val- | His- | His- | Gln- | Lys- | Leu- | Val- | Phe- | Phe- | Ala- | Glu- | Asp |
|---|---|---|---|---|---|---|---|---|---|---|---|
| 12 | 13 | 14 | 15 | 16 | 17 | 18 | 19 | 20 | 21 | 22 | 23 (SEQ ID NO: 45) | residues, respectively, which residues are predominantly involved in the binding of the antibody, wherein said 4 distinct binding sites are located in close proximity to each other on the antigen, separated by at least one amino acid residue not involved in antibody binding or to a significantly smaller extent as compared to said one amino acid residue and said two consecutive amino acid residues of the 4 distinct binding sites thus forming a conformational discontinuous epitope.

In particular, the first of the two consecutive amino acid residues predominantly involved in the binding of the antibody are -Lys-Leu-, and the second of the at least two consecutive amino acid residues are -Phe-Phe-, the first of the single amino residues is -His- and the second of the single amino residues is -Asp- embedded within the following core sequence:

-His-Xaa2-Lys-Leu-Xaa4-Phe-Phe-Xaa5-Xaa6-Asp- (SEQ ID NO: 18)

wherein

Xaa$_2$ is an amino acid residue selected from the group comprising Asn and Gln;

Xaa$_4$ is an amino acid residue selected from the group comprising Ala, Val, Leu, norleucine, Met, Phe, and Ile;

Xaa$_5$ is an amino acid residue selected from the group comprising Ala, Val, Leu, Ser and Ile;

Xaa$_6$ is an amino acid residue selected from the group comprising Glu and Asp, and wherein said amino acid residues Xaa$_2$, Xaa$_3$, Xaa$_4$, Xaa$_5$, Xaa$_6$, Xaa$_7$ are not involved in antibody binding or to a significantly smaller extent as compared to the -His-, -Asp-, the -Lys-Leu, and the -Phe-Phe- binding site.

In a specific embodiment of the invention, the recognition and binding sites as defined herein before are forming a conformational discontinuous epitope localized in a region of the β-amyloid protein between amino acid residue 12 to 24, particularly between residues 14 to 23, more particularly between amino acid residues 14 and 20, wherein the three distinct recognition and binding sites comprising 1 and 2 amino acid residues, respectively, are located at position 16, 17, and at position 19 and 20, and at position 14, respectively, which residues are predominantly involved in the binding of the β-amyloid protein and wherein said three distinct recognition and binding sites are separated by one amino acid residue located at position 15 and 18, respectively, which amino acids are not involved in the binding of the antigen or, at least, to a substantially smaller extent.

In a specific embodiment, said consecutive amino acid residues, particularly -Lys-Leu- at position 16 and 17 and -Phe-Phe- at position 19 and 20, which are predominantly involved in the binding of the β-amyloid protein, are embedded into the following core region:

| Val- | His- | His- | Gln- | Lys- | Leu- | Val- | Phe- | Phe- | Ala- | Glu- | Asp |
|---|---|---|---|---|---|---|---|---|---|---|---|
| 12 | 13 | 14 | 15 | 16 | 17 | 18 | 19 | 20 | 21 | 22 | 23 (SEQ ID NO: 45) |

In a further specific embodiment, said consecutive amino acid residues, particularly -Lys- at position 16, -Leu- at position 17 and -Phe-Phe- at position 19 and 20, and -His- at position 14, which are predominantly involved in the binding of the β-amyloid protein are embedded into the following core region:

| Val- | His- | His- | Gln- | Lys- | Leu- | Val- | Phe- | Phe- | Ala- | Glu- | Asp- |
|---|---|---|---|---|---|---|---|---|---|---|---|
| 12 | 13 | 14 | 15 | 16 | 17 | 18 | 19 | 20 | 21 | 22 | 23 (SEQ ID NO: 45) |

In a specific embodiment of the invention, the antibody according to the invention is raised against an antigen fragment which does not contain said distinct binding site.

This shift in the epitopic region may have at least partially been caused by the use of a supramolecular antigenic construct comprising an antigenic peptide corresponding to the amino acid sequence of the β-amyloid peptide, particularly of β-amyloid peptide Aβ$_{1-16}$, modified with a hydrophilic moiety such as, for example, polyethylene glycol (PEG), wherein said hydrophilic moiety is covalently bound to each of the termini of the antigenic peptide through at least one, particularly one or two amino acids such as, for example, lysine, glutamic acid and cystein or any other suitable amino acid or amino acid analogue capable of serving as a connecting device for coupling the hydrophilic moiety to the peptide fragment, as described herein below in the immunization process. When a PEG is used as the hydrophilic moiety, the free PEG termini are covalently bound to phosphatidylethanolamine or any other compound suitable to function as the anchoring element, for example, to embed the antigenic construct in the bilayer of a liposome as described herein.

Also the use of lipid A as part of the immunization protocol may have contributed to a shift in the epitopic region.

In a specific embodiment of the invention, an antibody is provided, which comprises the Light Chain Variable Region (LCVR) of SEQ ID NO: 7.

In another specific embodiment, the invention relates to the Light Chain Variable Region (LCVR) of SEQ ID NO: 7.

In still another specific embodiment of the invention, an antibody is provided, which comprises the Heavy Chain Variable Region (HCVR) of SEQ ID NO: 8.

In a further specific embodiment, the invention relates to the Heavy Chain Variable Region (HCVR) of SEQ ID NO: 8.

In one embodiment, the invention relates to an antibody, which comprises both the heavy chain variable region of SEQ ID NO: 8 and the light chain variable region of SEQ ID NO: 7.

Also part of the invention is an antibody comprising a Light Chain Variable Region (LCVR) or Heavy Chain Variable Region (HCVR) or both, a Light Chain Variable Region (LCVR) and a Heavy Chain Variable Region (HCVR) that is homolgous to any of the peptides provided in SEQ ID NO: 7 and 8, respectively.

In particular, the invention relates to an antibody or a fragment thereof, according to the present invention and as described herein before wherein the Light Chain Variable Region (LCVR) has an amino acid sequence that is 90%, 91%, 92%, 93%, 94%, 95%, 96%, 97%, 98% or 99% identical to the sequence given in SEQ ID NO: 7.

Further, the invention relates to an antibody or a fragment thereof, according to the present invention and as described herein before wherein the Heavy Chain Variable Region (HCVR) has an amino acid sequence that is 90%, 91%, 92%, 93%, 94%, 95%, 96%, 97%, 98% or 99% identical to the sequence given in SEQ ID NO: 8.

Further, the invention relates to an antibody or a fragment thereof, according to the present invention and as described herein before wherein the Light Chain Variable Region (LCVR) and the Heavy Chain Variable Region (HCVR) together have an amino acid sequence that is 85%, 86%, 87%, 88%, 89%, 90%, 91%, 92%, 93%, 94%, 95%, 96%, 97%, 98% or 99% identical to the sequence given in SEQ ID NOS: 7 and 8.

In another specific embodiment, the invention relates to the light chain variable region which has an amino acid sequence that is 90%, 91%, 92%, 93%, 94%, 95%, 96%, 97%, 98% or 99% identical to the sequence given in SEQ ID NO: 7.

In a further specific embodiment, the invention relates to the heavy chain variable region which has an amino acid sequence that is 90%, 91%, 92%, 93%, 94%, 95%, 96%, 97%, 98% or 99% identical to the sequence given in SEQ ID NO: 8.

In another embodiment of the invention, a polynucleotide is provided comprising a nucleotide sequence encoding the antibody according to the invention as described herein before.

In particular, the invention relates to a polynucleotide comprising a nucleotide sequence encoding an antibody according to the invention comprising
  a) at least the nucleotide sequence of the light chain variable region of SEQ ID NO: 9
  b) a nucleotide sequence that differ from the nucleotide sequence of (a) in codon sequence due to the degeneracy of the genetic code
  c) the complementary sequence to (a) and (b) or
  d) a fragment of a nucleotide sequence of (a), (b) or (c) comprising a contiguous stretch of nucleotides selected from the group consisting of at least 20 contiguous nucleotides, at least 25 contiguous nucleotides, at least 30 contiguous nucleotides, at least 35 contiguous nucleotides, at least 40 contiguous nucleotides, at least 45 contiguous nucleotides, and at least 50 contiguous nucleotides.

In another embodiment, the invention relates to a polynucleotide comprising a nucleotide sequence encoding an antibody according to the invention comprising
  a) at least the nucleotide sequence of the light chain of SEQ ID NO: 10
  b) a nucleotide sequence that differ from the nucleotide sequence of (a) in codon sequence due to the degeneracy of the genetic code
  c) the complementary sequence to (a) and (b) or
  d) a fragment of a nucleotide sequence of (a), (b) or (c) comprising a contiguous stretch of nucleotides selected from the group consisting of at least 20 contiguous nucleotides, at least 25 contiguous nucleotides, at least 30 contiguous nucleotides, at least 35 contiguous nucleotides, at least 40 contiguous nucleotides, at least 45 contiguous nucleotides, and at least 50 contiguous nucleotides.

In still another embodiment, the invention relates to a polynucleotide comprising a nucleotide sequence encoding an antibody according to the invention comprising
  a) at least the nucleotide sequence of the heavy chain variable region of SEQ ID NO: 11.
  b) a nucleotide sequence that differ from the nucleotide sequence of (a) in codon sequence due to the degeneracy of the genetic code
  c) the complementary sequence to (a) and (b) or
  d) a fragment of a nucleotide sequence of (a), (b) or (c) comprising a contiguous stretch of nucleotides selected from the group consisting of at least 20 contiguous nucleotides, at least 25 contiguous nucleotides, at least 30 contiguous nucleotides, at least 35 contiguous nucleotides, at least 40 contiguous nucleotides, at least 45 contiguous nucleotides, and at least 50 contiguous nucleotides.

In still another embodiment, the invention relates to a polynucleotide comprising a nucleotide sequence encoding an antibody according to the invention comprising
  a) at least the nucleotide sequence of the heavy chain of SEQ ID NO: 12 or to the complementary sequence
  b) a nucleotide sequence that differ from the nucleotide sequence of (a) in codon sequence due to the degeneracy of the genetic code
  c) the complementary sequence to (a) and (b) or
  d) a fragment of a nucleotide sequence of (a), (b) or (c) comprising a contiguous stretch of nucleotides selected from the group consisting of at least 20 contiguous nucleotides, at least 25 contiguous nucleotides, at least 30 contiguous nucleotides, at least 35 contiguous nucleotides, at least 40 contiguous nucleotides, at least 45 contiguous nucleotides, and at least 50 contiguous nucleotides.

Also comprised by the invention is a polynucleotide comprising
  a) the nucleotide sequence of SEQ ID NO: 9 encoding the light chain variable region
  b) a nucleotide sequence that differ from the nucleotide sequence of (a) in codon sequence due to the degeneracy of the genetic code
  c) the complementary sequence to (a) and (b) or
  d) a fragment of a nucleotide sequence of (a), (b) or (c) comprising a contiguous stretch of nucleotides selected from the group consisting of at least 20 contiguous nucleotides, at least 25 contiguous nucleotides, at least 30 contiguous nucleotides, at least 35 contiguous nucleotides, at least 40 contiguous nucleotides, at least 45 contiguous nucleotides, and at least 50 contiguous nucleotides.

Also comprised by the invention is a polynucleotide comprising
  a) the nucleotide sequence of SEQ ID NO: 10 encoding the light chain.
  b) a nucleotide sequence that differ from the nucleotide sequence of (a) in codon sequence due to the degeneracy of the genetic code
  c) the complementary sequence to (a) and (b) or
  d) a fragment of a nucleotide sequence of (a), (b) or (c) comprising a contiguous stretch of nucleotides selected from the group consisting of at least 20 contiguous nucleotides, at least 25 contiguous nucleotides, at least 30 contiguous nucleotides, at least 35 contiguous nucleotides, at least 40 contiguous nucleotides, at least 45 contiguous nucleotides, and at least 50 contiguous nucleotides.

Also comprised by the invention is a polynucleotide comprising
  a) the nucleotide sequence of SEQ ID NO: 11 encoding the heavy chain variable region
  b) a nucleotide sequence that differ from the nucleotide sequence of (a) in codon sequence due to the degeneracy of the genetic code
  c) the complementary sequence to (a) and (b) or
  d) a fragment of a nucleotide sequence of (a), (b) or (c) comprising a contiguous stretch of nucleotides selected from the group consisting of at least 20 contiguous nucleotides, at least 25 contiguous nucleotides, at least 30 contiguous nucleotides, at least 35 contiguous nucleotides, at least 40 contiguous nucleotides, at least 45 contiguous nucleotides, and at least 50 contiguous nucleotides.

Also comprised by the invention is a polynucleotide comprising
  a) the nucleotide sequence of SEQ ID NO: 12 encoding the heavy chain
  b) a nucleotide sequence that differ from the nucleotide sequence of (a) in codon sequence due to the degeneracy of the genetic code
  c) the complementary sequence to (a) and (b) or
  d) a fragment of a nucleotide sequence of (a), (b) or (c) comprising a contiguous stretch of nucleotides selected from the group consisting of at least 20 contiguous nucleotides, at least 25 contiguous nucleotides, at least 30 contiguous nucleotides, at least 35 contiguous nucleotides, at least 40 contiguous nucleotides, at least 45 contiguous nucleotides, and at least 50 contiguous nucleotides.

In a further embodiment, the invention relates to any nucleotide sequence that hybridizes to
  a) a nucleotide sequence according to the invention and as given in SEQ ID NOS: 9, 10, 11 and 12, respectively,
  b) a nucleotide sequence that differ from the nucleotide sequence of (a) in codon sequence due to the degeneracy of the genetic code
  c) the complementary sequence to (a) and (b) or
  d) a fragment of a nucleotide sequence of (a), (b) or (c) comprising a contiguous stretch of nucleotides selected from the group consisting of at least 20 contiguous nucleotides, at least 25 contiguous nucleotides, at least 30 contiguous nucleotides, at least 35 contiguous nucleotides, at least 40 contiguous nucleotides, at least 45 contiguous nucleotides, and at least 50 contiguous nucleotides.

In particular, the invention relates to any nucleotide sequence that hybridizes under conventional hybridization conditions, particularly under stringent hybridization conditions, to a nucleotide sequence according to the invention and as given in SEQ ID NOS: 9, 10, 11 and 12, respectively, particularly to the complementary strand thereof.

In a further embodiment, the invention relates to any nucleotide sequence that hybridizes to a nucleotide sequence according to the present invention and as given in SEQ ID NOS: 9, 10, 11 and 12, respectively, particularly to the complementary strand thereof, under conventional hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 70° C., preferably at 65° C. (regarding the definition of SSPE, SSC and Denhardts solution (see Sambrook et al. loc. cit.).

In particular, the invention relates to any nucleotide sequence that hybridizes to a nucleotide sequence according to the present invention and as given in SEQ ID NOS: 9, 10, 11 and 12, respectively, particularly to the complementary strand thereof, under stringent hybridization conditions as for instance described in Sambrook et al, supra, more particularly under stringent hybridization conditions where hybridization and washing occurs at 65° C. as indicated above.

In a specific embodiment the present invention provides an antibody, particularly a bifunctional antibody, but especially a monoclonal antibody, particularly a bifunctional monoclonal antibody, including any functionally equivalent antibody or functional parts thereof, which antibody has the characteristic properties of an antibody produced by a hybridoma cell line selected from the group consisting of FP 12H3, FP 12H3-C2, and FP 12H3-G2 deposited on Dec. 1, 2005 and Dec. 9, 2005, respectively, as DSM ACC2752, DSM ACC 2750 and DSM ACC2751, respectively.

More particularly, the invention relates to an antibody including any functionally equivalent antibody or functional parts thereof produced by hybridoma cell line FP 12H3, deposited on Dec. 1, 2005 and Dec. 9, 2005, respectively as DSM ACC2752.

More particularly, the invention relates to a monoclonal antibody including any functionally equivalent antibody or functional parts thereof produced by hybridoma cell line FP 12H3-C2, deposited on Dec. 1, 2005 and Dec. 9, 2005, respectively as DSM ACC2750.

More particularly, the invention relates to a monoclonal antibody including any functionally equivalent antibody or functional parts thereof produced by hybridoma cell line FP 12H3-C2, deposited on Dec. 1, 2005 and Dec. 9, 2005, respectively as DSM ACC2751.

In another specific embodiment the present invention provides an antibody, particularly a bifunctional antibody, but especially a monoclonal antibody, particularly a bifunctional monoclonal antibody, including any functionally equivalent antibody or functional parts thereof, which antibody has the characteristic properties of an antibody produced by hybridoma cell line ET 7E3 deposited on Dec. 8, 2005 as DSM ACC2755.

More particularly, the invention relates to a monoclonal antibody including any functionally equivalent antibody or functional parts thereof produced by hybridoma cell line ET 7E3, deposited on Dec. 8, 2005 as DSM ACC2755.

In another specific embodiment the present invention provides an antibody, particularly a bifunctional antibody, but especially a monoclonal antibody, particularly a bifunctional monoclonal antibody, including any functionally equivalent antibody or functional parts thereof, which antibody has the characteristic properties of an antibody produced by hybridoma cell line EJ 7H3 deposited on Dec. 8, 2005 as DSM ACC2756.

More particularly, the invention relates to a monoclonal antibody including any functionally equivalent antibody or functional parts thereof produced by hybridoma cell line EJ 7H3, deposited on Dec. 8, 2005 as DSM ACC2756.

It is another object of the present invention to provide methods and compositions comprising an antibody according to the invention and as described herein before for the prevention and/or therapeutic treatment and/or alleviation of the effects of diseases and disorders which are caused by or associated with amyloid or amyloid-like proteins including amyloidosis, a group of diseases and disorders associated with amyloid plaque formation including secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases and conditions which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetis; senile cardiac amyloidosis; endocrine tumors, and others, including macular degeneration, for example, by passively immunizing a human or animal with an antibody according to the invention and as described herein before.

Another object of the present invention is to provide a method of using a monoclonal antibody and/or a functional part thereof according to the invention and compositions comprising an antibody according to the invention and as described herein before for diagnosing and therapeutic intervention of diseases and disorders which are caused by or associated with amyloid or amyloid-like proteins including amyloidosis, a group of diseases and disorders associated with amyloid plaque formation including secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetis; senile cardiac amyloidosis; endocrine tumors, and others, including macular degeneration.

In particular, it is an object of the present invention to provide a method of using a monoclonal antibody and/or a functional part thereof according to the invention and compositions comprising an antibody, particularly a bispecific or bi-effective antibody but especially a bispecific or bi-effective monoclonal antibody according to the invention and as described herein before for reducing and preventing the occurrence of neurological disorders, including but not limited to Alzheimer's Disease.

The compositions according to the present invention comprise an antibody, particularly a bispecific or bi-effective antibody, according to the invention and as described herein before including any functionally equivalent antibody or functional parts thereof, particularly in a therapeutically effective amount or, more particularly, a monoclonal antibody, especially a bispecific or bi-effective monoclonal antibody, according to the invention and as described herein before including any functionally equivalent antibody or functional parts thereof, particularly in a therapeutically effective amount and, optionally, a pharmaceutically acceptable carrier and/or a diluent and/or an excipient.

Particularly, the composition according to the present invention comprises an antibody, particularly a monoclonal antibody including any functionally equivalent antibody or functional parts thereof which antibody is capable of inhibiting the aggregation of amyloid monomeric peptides, specifically β-amyloid monomeric peptides such as, for example, Aβ monomeric peptides 1-39; 1-40, 1-41, 1-42, or 1-43, but especially $A\beta_{1-42}$ monomeric peptides, into high molecular polymeric amyloid fibrils or filaments and, optionally, a pharmaceutically acceptable carrier and/or a diluent and/or an excipient.

In a further embodiment of the invention a composition is provided comprising an antibody, particularly a monoclonal antibody, including any functionally equivalent antibody or functional parts thereof, which antibody, upon co-incubation, particularly upon co-incubation at a molar concentration ratio of up to 1:100, more particularly at a molar concentration ratio of between 1:30 and 1:100, but especially at a molar concentration ratio of 1:100, with amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, inhibits the aggregation of the Aβ monomers into high molecular polymeric fibrils or filaments. In particular, said inhibition amounts to at least 50%, particularly to at least 65%, more particularly to at least 75%, even more particularly to at least 80%, but especially to at least 85%-90%, or more as compared to the respective amyloid peptide monomers incubated in buffer (control) and, optionally, a pharmaceutically acceptable carrier and/or a diluent and/or an excipient.

In particular, the co-incubation of the antibody according to the invention with amyloid monomeric peptides is carried out for 48 hours at a temperature of 37° C.

The aggregation inhibition potential of the antibody according to the invention may be determined by density-gradient ultracentrifugation followed by a SDS-PAGE sedimentation analysis on a preformed gradient and/or by a thioflavin T (Th-T) fluorescent assay.

The present invention further provides a composition comprising an antibody which is capable of disaggregating high molecular polymeric amyloid fibrils or filaments formed by the aggregation of amyloid monomeric peptides, specifically β-amyloid monomeric peptides such as, for example, Aβ monomeric peptides 1-39; 1-40, 1-41, 1-42, or 1-43, but especially $A\beta_{1-42}$ monomeric peptides and, optionally, a pharmaceutically acceptable carrier and/or a diluent and/or an excipient.

Through the disaggregation of amyloidogenic polymeric fibrils or filaments the antibodies according to the present invention are capable of preventing or slowing down the formation of amyloid plaques which leads to an alleviation of the symptoms associated with the disease and a delay or reversal of its progression.

In another embodiment of the invention a composition is provided comprising an antibody, particularly a monoclonal antibody, including any functionally equivalent antibody or functional parts thereof, which antibody, upon co-incubation at a molar concentration ratio of between 1:30 and 1:100, particularly at a ratio of 1:100, with preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, particularly upon co-incubation for 24 hours at a temperature of 37° C., is capable of disaggregating the preformed polymeric fibrils or filaments by at least 35%, particularly by at least 40%, more particularly by at least 50%, even more particularly by at least 60%, but especially by at least 70% or more and, optionally, a pharmaceutically acceptable carrier and/or a diluent and/or an excipient.

The disaggregation potential of the antibody according to the invention may be determined by density-gradient ultracentrifugation followed by a SDS-PAGE sedimentation analysis on a preformed gradient and/or by a thioflavin T (Th-T) fluorescent assay.

The present invention further provides a composition comprising an antibody or functional parts thereof which antibody is conformationally sensitive, particularly in an effective amount, more particularly in a therapeutically effective amount.

In a further embodiment of the invention composition is provided comprising an antibody is provided, but especially a monoclonal antibody, including any functionally equivalent antibody or functional parts thereof, which antibody, upon co-incubation with preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, particularly upon co-incubation for 24 hours at a temperature of 37° C., is capable of inducing a transition of the β-sheet conformation towards an α-helix and/or a random coil conformation, but particularly a random coil conformation, even more particularly a random coil conformation at a given location in the molecule, especially in the environment of Val12 of the Aβ protein, which leads to an increase of the random coil conformation at the expense of the β-sheet conformation and an improved solubilization of the preformed high molecular polymeric amyloid fibrils or filaments and, optionally, a pharmaceutically acceptable carrier and/or a diluent and/or an excipient. In particular the decrease of the β-sheet conformation amounts to at least 30%, particularly to at least 35%, and more particularly to at least 40% and more as compared to the respective preformed amyloid polymeric fibrils or filaments incubated in buffer (control).

The antibody's potential in inducing a transition in the secondary structure is determined by solid state 13C NMR spectroscopy but, in particular, by measuring the integral intensities of the conformations of Val 12 Cβ in the $A\beta_{1-42}$ peptide.

The present invention further provides a composition comprising an antibody, particularly a monoclonal antibody, including any functionally equivalent antibody or functional parts thereof, particularly in a therapeutically effective amount, which antibody is bifunctional in that it exhibits both an aggregation inhibition property as well as a disaggregation property as defined herein before, preferably paired with a high degree of conformational sensitivity and, optionally, a pharmaceutically acceptable carrier and/or a diluent and/or an excipient.

In still another embodiment of the invention a composition is provided comprising a bifunctional antibody, but especially a bifunctional monoclonal antibody, including any functionally equivalent antibody or functional parts thereof, which antibody, upon co-incubation with amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, inhibits the aggregation of the Aβ monomers into high molecular polymeric fibrils and, in addition, upon co-incubation with preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, is capable of disaggregating the preformed polymeric fibrils or filaments and, optionally, a pharmaceutically acceptable carrier and/or a diluent and/or an excipient.

In a specific embodiment of the invention the co-incubation of the bifunctional antibody according to the invention, but especially of the bifunctional monoclonal antibody according to the invention with amyloid monomeric peptides and preformed high molecular polymeric amyloid fibrils or filaments, respectively, takes place at a molar concentration ratio of up to 1:100, particularly at a ratio of between 1:30 and 1:100, and more particularly at a ration of 1:100.

In a further specific embodiment of the invention co-incubation with amyloid monomeric peptides and preformed high molecular polymeric amyloid fibrils or filaments is done for 48 hours and 24 hours, respectively, at a temperature of 37° C.

In still another specific embodiment of the invention a composition is provided comprising a bifunctional antibody according to the invention, but especially a bifunctional monoclonal antibody according to the invention which is capable of disaggregating the preformed polymeric fibrils or filaments by at least 10%, particularly by at least 25%, more particularly by at least 35%, even more particularly by at least 50%, but especially by at least 60-70% or more and, optionally, a pharmaceutically acceptable carrier and/or a diluent and/or an excipient.

In still another specific embodiment of the invention a composition is provided comprising a bifunctional antibody according to the invention, but especially a bifunctional monoclonal antibody according to the invention inhibits the aggregation of amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides by at least 50%, particularly by at least 65%, more particularly by at least 75%, even more particularly by at least 80%, but especially by at least 85-90%, or more as compared to the respective amyloid peptide monomers incubated in buffer (control) and, optionally, a pharmaceutically acceptable carrier and/or a diluent and/or an excipient.

In particular, the present invention provides a composition comprising an antibody, particularly a monoclonal antibody, including any functionally equivalent antibody or functional parts thereof, which antibody mediates the inhibition of polymerization of amyloid monomeric peptides, specifically β-amyloid monomeric peptides such as, for example, Aβ monomeric peptides 1-39; 1-40, 1-41, 1-42, or 1-43, but especially a $A\beta_{1-42}$ monomeric peptides and/or induces solubilization of preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, through specific and direct binding of the antibody to the Aβ fibers, which leads to a transition of secondary conformation and, optionally, a pharmaceutically acceptable carrier and/or a diluent and/or an excipient.

The present invention further provides a composition comprising an antibody, particularly a monoclonal antibody, including any functionally equivalent antibody or functional parts thereof, which antibody directly and specifically binds to β-amyloid fibers such as, for example, fibers comprising Aβ monomeric peptides 1-39; 1-40, 1-41, 1-42, or 1-43, but especially to fibers comprising $A\beta_{1-42}$ monomeric peptides and/or induces solubilization of preformed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42, or 1-43, but especially $A\beta_{1-42}$ monomeric peptides, by targeting and specifically binding to an epitopic region of the β-amyloid protein, particularly an epitopic region of the Aβ polypeptide confined by amino acid residues $aa_n$-$aa_m$ with n being an integer between 2 and 15, particularly between 5 and 15, more particularly between 8 and 15, even more particularly between 10 and 15 and m being an integer between 3 and 17, particularly between 6 and 17, more particularly between 9 and 17, even more particularly between 11 and 17, wherein n and m cannot be identical numbers and n must always be a smaller number than m, with the difference between n and m$\geq$2 and, optionally, a pharmaceutically acceptable carrier and/or a diluent and/or an excipient.

The binding of the antibody according to the invention may induce a conformational transition in said protein, particularly a transition of the β-sheet conformation towards an α-helix and/or a random coil conformation, but particularly a random coil conformation, even more particularly a random coil conformation at a given location in the molecule, especially in the environment of Val12 of the Aβ protein.

In a further embodiment, the invention provides a composition comprising an antibody, particularly a monoclonal antibody, including any functionally equivalent antibody or functional parts thereof, which antibody incorporates at least one of the properties mentioned herein before, that is aggregation inhibition, disaggregation, induction of conformational transition, recognition of and direct binding to the 4-16 and/or the 14 to 23, but particularly the 14 to 20 epitopic region, but especially a combination of two or more of said properties and, optionally, a pharmaceutically acceptable carrier and/or a diluent and/or an excipient.

In a specific embodiment, the invention provides a composition comprising an antibody, particularly a bifunctional antibody, but especially a monoclonal antibody, particularly a bifunctional monoclonal antibody, including any functionally equivalent antibody or functional parts thereof, which exhibits high specificity to $A\beta_{1-42}$ monomeric peptides but shows essentially no or only minor cross-reactivity to $A\beta_{1-38}$, $A\beta_{1-39}$, $A\beta_{1-40}$, and/or $A\beta_{1-41}$ monomeric peptides, particularly an antibody, but especially a monoclonal antibody, including any functionally equivalent antibody or functional parts thereof, which antibody is up to 100 fold, particularly 50 to 100 fold, more particularly 80 to 100 fold, but especially 100 fold more sensitive to amyloid peptide $A\beta_{1-42}$ as compared to $A\beta_{1-38}$, $A\beta_{1-39}$, $A\beta_{1-40}$, $A\beta_{1-41}$ and up to 1000 fold, particularly 500 to 1000 fold, more particularly 800 to 1000 fold, but especially 1000 fold more sensitive to amyloid peptide $A\beta_{1-42}$ as compared to $A\beta_{1-38}$, and thus capable of inhibiting, in vitro and in vivo, the aggregation of amyloidogenic monomeric peptides, but especially of amyloid peptide $A\beta_{1-42}$ and, optionally, a pharmaceutically acceptable carrier and/or a diluent and/or an excipient.

In another specific embodiment of the invention a composition is provided comprising an antibody, particularly a bifunctional antibody, but especially a monoclonal antibody, particularly a bifunctional monoclonal antibody, including any functionally equivalent antibody or functional parts thereof, which has a high binding sensitivity to amyloid peptide $A\beta_{1-42}$ and is capable of detecting $A\beta_{1-42}$ fibers in a concentration of down to at least 0.001 μg, but particularly in a concentration range of between 0.5 μg and 0.001 μg, more particularly between 0.1 μg and 0.001 μg, but especially in a concentration of 0.001 μg and, optionally, a pharmaceutically acceptable carrier and/or a diluent and/or an excipient.

In a very specific embodiment of the invention a composition comprising an antibody is provided, particularly a bifunctional antibody, but especially a monoclonal antibody, particularly a bifunctional monoclonal antibody, including any functionally equivalent antibody or functional parts thereof, which antibody is capable of detecting $A\beta_{1-42}$ fibers down to a minimal concentration of 0.001 μg and $A\beta_{1-40}$ fibers down to a minimal concentration of 0.1 μg and $A\beta_{1-38}$ fibers down to a minimal concentration of 1 μg amount of fibers and, optionally, a pharmaceutically acceptable carrier and/or a diluent and/or an excipient.

In a specific embodiment the present invention relates to a composition comprising a monoclonal antibody including any functionally equivalent antibody or functional parts thereof which antibody has the characteristic properties of an antibody produced by a hybridoma cell line selected from the group consisting of FP 12H3, FP 12H3-C2, and FP 12H3-G2 deposited on Dec. 1, 2005 and Dec. 9, 2005, respectively, as DSM ACC2752, DSM ACC2750 and DSM ACC2751, and, optionally, a pharmaceutically acceptable carrier and/or a diluent and/or an excipient.

More particularly, the invention relates to a composition comprising a monoclonal antibody including any functionally equivalent antibody or functional parts thereof produced by hybridoma cell line FP 12H3, deposited on Dec. 1, 2005 and Dec. 9, 2005, respectively as DSM ACC2752 and, optionally, a pharmaceutically acceptable carrier and/or a diluent and/or an excipient.

More particularly, the invention relates to a composition comprising a monoclonal antibody including any functionally equivalent antibody or functional parts thereof produced by hybridoma cell line FP 12H3-C2, deposited on Dec. 1, 2005 and Dec. 9, 2005, respectively as DSM ACC2750 and, optionally, a pharmaceutically acceptable carrier and/or a diluent and/or an excipient The invention further relates to a composition comprising a monoclonal antibody including any functionally equivalent antibody or functional parts thereof produced by hybridoma cell line FP 12H3-G2, deposited on Dec. 1, 2005 and Dec. 9, 2005, respectively as DSM ACC2751 and, optionally, a pharmaceutically acceptable carrier and/or a diluent and/or an excipient.

In another specific embodiment the present invention relates to a composition comprising a monoclonal antibody including any functionally equivalent antibody or functional parts thereof which antibody has the characteristic properties of an antibody produced by hybridoma cell line ET 7E3 deposited on Dec. 8, 2005 as DSM ACC2755 and, optionally, a pharmaceutically acceptable carrier and/or a diluent and/or an excipient.

The invention further relates to a composition comprising a monoclonal antibody including any functionally equivalent antibody or functional parts thereof produced by hybridoma cell line ET 7E3, deposited on Dec. 8, 2005 as DSM ACC2755 and, optionally, a pharmaceutically acceptable carrier and/or a diluent and/or an excipient In another specific embodiment the present invention relates to a composition comprising a monoclonal antibody including any functionally equivalent antibody or functional parts thereof which antibody has the characteristic properties of an antibody produced by hybridoma cell line EJ 7H3 deposited on Dec. 8, 2005 as DSM ACC2756 and, optionally, a pharmaceutically acceptable carrier and/or a diluent and/or an excipient.

The invention further relates to a composition comprising a monoclonal antibody including any functionally equivalent antibody or functional parts thereof produced by hybridoma cell line EJ 7H3, deposited on Dec. 8, 2005 as DSM ACC2756 and, optionally, a pharmaceutically acceptable carrier and/or a diluent and/or an excipient.

The antibody, particularly the monoclonal antibody according to the invention including any functionally equivalent antibody or functional parts thereof may be administered in combination with other biologically active substances and procedures for the treatment of diseases. The other biologically active substances may be part of the same composition already comprising the antibody according to the invention, in form of a mixture, wherein the antibody and the other biologically active substance are intermixed in or with the same pharmaceutically acceptable solvent and/or carrier or may be provided separately as part of a separate composition, which may be offered separately or together in form a kit of parts.

The antibody, particularly the monoclonal antibody according to the invention including any functionally equivalent antibody or functional parts thereof may be administered at the same time with the other biologically active substance or substances, intermittently or sequentially. For example, the monoclonal antibody according to the invention including any functionally equivalent antibody or functional parts thereof may be administered simultaneously with a first additional biologically active substance or sequentially after or before administration of the antibody. If an application scheme is chosen where more than one additional biologically active substance are administered together with the at least one antibody according to the invention, the compounds or substances may partially be administered simultaneously, partially sequentially in various combinations.

It is another object of the present invention to provide for mixtures of antibodies comprising at least one antibody according to the present invention and, optionally, one or more further biologically active substances, as well as to methods of using individual antibodies, or mixtures thereof including compositions comprising said antibodies or mixtures of antibodies for the prevention and/or therapeutic treatment and/or alleviation of the effects of diseases and disorders which are caused by or associated with amyloid or amyloid-like proteins including amyloidosis, a group of diseases and disorders associated with amyloid plaque formation including secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetis; senile cardiac amyloidosis; endocrine tumors, and others, including macular degeneration.

The mixtures according to the invention may comprise, in addition to an antibody according to the invention, a biologically active substance such as, for example, known compounds used in the medication of diseases and disorders which are caused by or associated with amyloid or amyloid-like proteins including amyloidosis, a group of diseases and disorders associated with amyloid or amyloid-like protein such as the Aβ protein involved in Alzheimer's disease.

In another embodiment of the invention, the other biologically active substance or compound may also be a therapeutic agent that may be used in the treatment of diseases and disorders which are caused by or associated with amyloid or amyloid-like proteins including amyloidosis caused by amyloid β or may be used in the medication of other neurological disorders.

The other biologically active substance or compound may exert its biological effect by the same or a similar mechanism as the antibody according to the invention or by an unrelated mechanism of action or by a multiplicity of related and/or unrelated mechanisms of action.

Generally, the other biologically active compound may include neutron-transmission enhancers, psychotherapeutic drugs, acterylcholine esterase inhibitors, calcium-channel blockers, biogenic amines, benzodiazepine tranquilizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists.

In particular, the mixture according to the invention may comprise at least one other biologically active compound selected from the group consisting of compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), secretase activators, β- and γ-secretase inhibitors, tau proteins, neurotransmitter, β-sheet breakers, anti-inflammatory molecules, or cholinesterase inhibitors (ChEIs) such as tacrine, rivastigmine, donepezil, and/or galantamine and other drugs and nutritive supplements, together with an antibody according to the present invention and, optionally, a pharmaceutically acceptable carrier and/or a diluent and/or an excipient.

In a further embodiment, the mixtures according to the invention may comprise niacin or memantine together with an antibody according to the present invention and, optionally, a pharmaceutically acceptable carrier and/or a diluent and/or an excipient.

In still another embodiment of the invention mixtures are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with an antibody according to the invention and, optionally, a pharmaceutically acceptable carrier and/or a diluent and/or an excipient.

In a specific embodiment of the invention, the compositions and mixtures according to the invention and as described herein before comprise the antibody and the biologically active substance, respectively, in a therapeutically effective amount.

Other compounds that can be suitably used in mixtures in combination with the antibody according to the present invention are, for example, described in WO 2004/058258 (see especially pages 16 and 17) including therapeutic drug targets (page 36-39), alkanesulfonic acids and alkanolsulfuric acids (pages 39-51), cholinesterase inhibitors (pages 51-56), NMDA receptor antagonists (pages 56-58), estrogens (pages 58-59), non-steroidal anti-inflammatory drugs (pages 60-61), antioxidants (pages 61-62), peroxisome proliferators-activated receptor (PPAR) agonists (pages 63-67), cholesterol-lowering agents (pages 68-75); amyloid inhibitors (pages 75-77), amyloid formation inhibitors (pages 77-78), metal chelators (pages 78-79), anti-psychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference.

Further provided is a method for producing an antibody, particularly a method for producing a monoclonal antibody, including any functionally equivalent antibody or functional parts thereof according to the invention, which method comprises raising antibodies but particularly monoclonal antibodies against a supramolecular antigenic construct comprising an antigenic peptide corresponding to the amino acid sequence of the β-amyloid peptide, particularly of β-amyloid peptide $A\beta_{1-15}$, $A\beta_{1-16}$ and $A\beta_{1-16(A14)}$, modified with hydrophobic moieties such as, for example, palmitic acid or a hydrophilic moiety such as, for example, polyethylene glycol (PEG) or a combination of both, wherein said hydrophobic and hydrophilic moiety, respectively, is covalently bound to each terminus through at least one, particularly one or two, amino acids such as, for example, lysine or any other suitable amino acid or amino acid analogue capable of serving as a coupling device or linker molecule for the coupling of said hydrophobic and hydrophilic moiety such as, for example, glutamic acid or cystein.

Also part of the invention is the use of a monoclonal antibody and/or a functional part thereof according to the invention and as described herein before and/or a pharmaceutical composition, or a mixture comprising said antibody, for the preparation of a medicament for treating or alleviating the effects of diseases and disorders which are caused by or associated with amyloid or amyloid-like proteins including amyloidosis, a group of diseases and disorders associated with amyloid plaque formation including secondary amyloidosis and age-related amyloidosis such as diseases including, but not limited to, neurological disorders such as Alzheimer's Disease (AD and diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetis; senile cardiac amyloidosis; endocrine tumors, and others, including macular degeneration.

In another embodiment of the present invention a method is provided for the preparation of a pharmaceutical composition using an antibody according to the invention and/or a functional part thereof but especially a monoclonal antibody and/or a functional part thereof or a functionally equivalent antibody, for use in treating or alleviating the effects of diseases and disorders which are caused by or associated with amyloid or amyloid-like proteins including amyloidosis, a group of diseases and disorders associated with amyloid plaque formation including secondary amyloidosis and age-related amyloidosis such as diseases including, but not limited to, neurological disorders such as Alzheimer's Disease (AD) and diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetis; senile cardiac amyloidosis; endocrine tumors, and others, including macular degeneration comprising formulating an antibody according to the invention in a pharmaceutically acceptable form.

The antibodies and/or functional parts thereof but especially the monoclonal antibodies and/or functional parts thereof or a functionally equivalent antibody and the compositions and mixtures comprising said antibody according to the present invention may be used for the preparation of a medicament for preventing, treating or alleviating the effects of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetis; senile cardiac amyloidosis; endocrine tumors, and others, including macular degeneration.

In a further embodiment of the invention a method is provided for reducing the plaque load in the brain of an animal, particularly a mammal, but especially a human suffering from a disease or condition leading to an increased plaque load in the brain comprising administering to an animal, particularly a mammal, more particularly a human in need of such a treatment, a therapeutically effective amount of an antibody and/or a functional part thereof but especially of the monoclonal antibody and/or a functional part thereof or of a functionally equivalent antibody according to the invention and as described herein before, or a composition or a mixture comprising said antibody.

In particular, the plaque load is reduced by at least 20%, particularly by at least 25%, more particularly by at least 30%, even more particularly by more than 30%.

In a further embodiment of the invention a method for reducing the amount of plaques in the brain of an animal, particularly a mammal, but especially a human suffering from a disease or condition leading to an increased plaque load in the brain comprising administering to an animal, particularly a mammal, more particularly a human in need of such a treatment, a therapeutically effective amount of an antibody and/or a functional part thereof but especially of the monoclonal antibody and/or a functional part thereof or of a functionally equivalent antibody according to the invention and as described herein before, or a composition or a mixture comprising said antibody.

In particular, the amount of plaques in the brain is reduced by at least 10%, particularly by at least 15%, more particularly by more than 15%.

In still another embodiment of the invention a method for decreasing the total amount of soluble Aβ in the brain of an animal, particularly a mammal, but especially a human suffering from a disease or condition leading to increased concentrations of soluble Aβ in the brain comprising administering to an animal, particularly a mammal, more particularly a human in need of such a treatment, a therapeutically effective amount of an antibody and/or a functional part thereof but especially of the monoclonal antibody and/or a functional part thereof or of a functionally equivalent antibody according to the invention and as described herein before, or a composition or a mixture comprising said antibody.

It is an objective of the present invention to provide a method for preventing, treating or alleviating the effects of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetis; senile cardiac amyloidosis; endocrine tumors, and others, including macular degeneration, by administering an antibody, but particularly a monoclonal antibody or a composition or mixture comprising such an antibody according to the invention to an animal or a human affected by such a disorder comprising administering to an animal, particularly a mammal, more particularly a human in need of such a treatment, a therapeutically effective amount of an antibody and/or a functional part thereof but especially of the monoclonal antibody and/or a functional part thereof or of a functionally equivalent antibody according to the invention and as described herein before, or a composition or a mixture comprising said antibody.

In a specific embodiment the invention provides a method for retaining or increasing cognitive memory capacity of an animal, particularly a mammal or a human suffering from memory impairment by administering to an animal, particularly a mammal or a human in need of such a treatment, an antibody, but particularly a monoclonal antibody according to the invention or a composition or mixture comprising such an antibody according to the invention and as described herein before.

In another embodiment of the present invention a method is provided for the preparation of a pharmaceutical composition using an antibody according to the invention and/or a functional part thereof but especially a monoclonal antibody and/or a functional part thereof or a functionally equivalent antibody for preventing, treating or alleviating the effects of diseases and disorders which are caused by or associated with amyloid or amyloid-like proteins including amyloidosis, a group of diseases and disorders associated with amyloid plaque formation including secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetis; senile cardiac amyloidosis; endocrine tumors, and others, including macular degeneration.

In a specific embodiment the invention provides a method for the preparation of a pharmaceutical composition using an antibody according to the invention and/or a functional part thereof but especially a monoclonal antibody and/or a functional part thereof or a functionally equivalent antibody for retaining or increasing cognitive memory capacity of an animal, particularly a mammal or a human, suffering from memory impairment by administering to an animal, particularly a mammal or a human, an antibody, but particularly a monoclonal antibody or a composition or mixture comprising such an antibody according to the invention and as described herein before.

These and other objects, features and advantages of the present invention will become apparent after a review of the following detailed description of the disclosed embodiment and the appended claims.

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

The terms "detecting" or "detected" as used herein mean using known techniques for detection of biologic molecules such as immunochemical or histological methods and refer to qualitatively or quantitatively determining the presence or concentration of the biomolecule under investigation.

"Amyloid β, Aβ or β-amyloid" is an art recognized term and refers to amyloid β proteins and peptides, amyloid β precursor protein (APP), as well as modifications, fragments and any functional equivalents thereof. In particular, by amyloid β as used herein is meant any fragment produced by proteolytic cleavage of APP but especially those fragments which are involved in or associated with the amyloid pathologies including, but not limited to, $A\beta_{1-38}$, $A\beta_{1-39}$, $A\beta_{1-40}$, $A\beta_{1-41}$ $A\beta_{1-42}$ and $A\beta_{1-43}$.

The structure and sequences of the amyloid β peptides as mentioned above are well known to those skilled in the art and methods of producing said peptides or of extracting them from brain and other tissues are described, for example, in Glenner and Wong, Biochem Biophys Res Comm 129, 885-890 (1984). Moreover, amyloid β peptides are also commercially available in various forms.

"Aβ Fibril" or "Aβ Filament" or "Amyloid fibrils" are polymeric forms of monomeric protein forming individual or bundled fibers with constant fiber diameter which are insoluble in aqueous medium and contain large amounts of a cross-☐ structure in their core; mostly with beta-strands perpendicular to the fibril axis 1.2,3)

"Monomeric Aβ" or "Aβ monomer" are completely solubilized amyloid ☐ protein without aggregated complexes in aqueous medium.

"Polymeric soluble amyloid" and "oligomeric Aβ" and "Aβ" refers to multiple aggregated monomers of amyloid peptides, or of amyloid-like peptides, or of modified or truncated amyloid peptides or of other derivates of amyloid peptides forming oligomeric or polymeric structures which are soluble both in vitro in aqueous medium and in vivo in the mammalian or human body more particularly in the brain, but particularly to multiple aggregated monomers of amyloid β (Aβ) or of modified or truncated amyloid β (Aβ) peptides or of derivatives thereof, which are soluble in the mammalian or human body more particularly in the brain, respectively.

By "isolated" is meant a biological molecule free from at least some of the components with which it naturally occurs.

The terms "antibody" or "antibodies" as used herein is an art recognized term and is understood to refer to molecules or active fragments of molecules that bind to known antigens, particularly to immunoglobulin molecules and to immunologically active portions of immunoglobulin molecules, i.e. molecules that contain a binding site that immunospecifically binds an antigen. The immunoglobulin according to the invention can be of any type (IgG, IgM, IgD, IgE, IgA and IgY) or class (IgG1, IgG2, IgG3, IgG4, IgA1 and IgA2) or subclasses of immunoglobulin molecule.

"Antibodies" are intended within the scope of the present invention to include monoclonal antibodies, polyclonal, chimeric, single chain, bispecific or bi-effective, simianized, human and humanized antibodies as well as active fragments thereof. Examples of active fragments of molecules that bind to known antigens include Fab and F(ab')$_2$ fragments, including the products of an Fab immunoglobulin expression library and epitope-binding fragments of any of the antibodies and fragments mentioned above.

These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl. Acad Sci USA, 86:10029-10032 (1989), Hodgson et al., Bio/Technology, 9:421 (1991)).

A "humanized antibody" may also be obtained by a novel genetic engineering approach that enables production of affinity-matured humanlike polyclonal antibodies in large animals such as, for example, rabbits (http://www.rctech.com/bioventures/therapeutic.php).

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody.

For the purpose of the present invention, "monoclonal antibody" is also to be understood to comprise antibodies that are produced by a mother clone which has not yet reached full monoclonality.

"Functionally equivalent antibody" is understood within the scope of the present invention to refer to an antibody which substantially shares at least one major functional property with an antibody mentioned above and herein described comprising: binding specificity to the β-amyloid protein, particularly to the $Aβ_{1-42}$ protein, and more particularly to the 4-16 epitopic region of the $Aβ_{1-42}$ protein, immunoreactivity in vitro, inhibition of aggregation of the $Aβ_{1-42}$ monomers into high molecular polymeric fibrils and/or disaggregation of preformed $Aβ_{1-42}$ polymeric fibrils, and/or a β-sheet breaking property and alleviating the effects of diseases and disorders which are caused by or associated with amyloid or amyloid-like proteins including amyloidosis, a group of diseases and disorders associated with amyloid plaque formation including secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetis; senile cardiac amyloidosis; endocrine tumors, and others, including macular degeneration, when administered prophylactically or therapeutically. The antibodies can be of any class such as IgG, IgM, or IgA, etc or any subclass such as IgG1, IgG2a, etc and other subclasses mentioned herein above or known in the art, but particularly of the IgG2 class. Further, the antibodies can be produced by any method, such as phage display, or produced in any organism or cell line, including bacteria, insect, mammal or other type of cell or cell line which produces antibodies with desired characteristics, such as humanized antibodies. The antibodies can also be formed by combining a Fab portion and an Fc region from different species.

The term "bispecific" or "bifunctional" and "bi-effective" is used synonymously within the scope of this application to characterize an antibody which exhibits both an inhibition property on amyloid or amyloid-like fiber formation as well as a disaggregation property of amyloid or amyloid-like fibers . . . .

The term "antigen" refers to an entity or fragment thereof which can induce an immune response in an organism, particularly an animal, more particularly a mammal including a human. The term includes immunogens and regions responsible for antigenicity or antigenic determinants.

As used herein, the term "soluble" means partially or completely dissolved in an aqueous solution.

Also as used herein, the term "immunogenic" refers to substances which elicit or enhance the production of antibodies, T-cells and other reactive immune cells directed against an immunogenic agent and contribute to an immune response in humans or animals.

An immune response occurs when an individual produces sufficient antibodies, T-cells and other reactive immune cells against administered immunogenic compositions of the present invention to moderate or alleviate the disorder to be treated.

"Polymeric soluble amyloid" refers to multiple aggregated monomers of amyloid peptides, or of amyloid-like peptides, or of modified or truncated amyloid peptides or of other derivates of amyloid peptides forming oligomeric or polymeric structures which are soluble in the mammalian or human body more particularly in the brain, but particularly to multiple aggregated monomers of amyloid β (Aβ) or of modified or truncated amyloid β (Aβ) peptides or of derivatives thereof, which are soluble in the mammalian or human body more particularly in the brain.

The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The term "carrier" as used herein means a structure in which antigenic peptide or supramolecular construct can be incorporated into or can be associated with, thereby presenting or exposing antigenic peptides or part of the peptide to the immune system of a human or animal. Any particle that can be suitably used in animal or human therapy such as, for example, a vesicle, a particle or a particulate body may be used as a carrier within the context of the present invention.

The term "carrier" further comprises methods of delivery wherein supramolecular antigenic construct compositions comprising the antigenic peptide may be transported to desired sites by delivery mechanisms. One example of such a delivery system utilizes colloidal metals such as colloidal gold.

In addition, the term "carrier" further comprises delivery mechanisms known to those skilled in the art including, but not limited to, keyhole limpet hemocyanin (KLH), bovine serum albumin (BSA) and other adjuvants.

In the supramolecular antigenic construct according to the present invention, the liposome may have a dual function in that it can be used as a carrier comprising the supramolecular construct as described herein before and, at the same time, function as an adjuvant to increase or stimulate the immune response within the target animal or human to be treated with the therapeutic vaccine according to the invention. It is also to be understood that the supramolecular antigenic construct compositions of the present invention can further comprise additional adjuvants such as, for example, lipid A, alum, calcium phosphate, interleukin 1, and/or microcapsules of polysaccharides and proteins, but particularly a detoxified lipid A, such as monophosphoryl or diphosphoryl lipid A, or alum, further preservatives, diluents, emulsifiers, stabilizers, and other components that are known and used in vaccines of the prior art. Moreover, any adjuvant system known in the art can be used in the composition of the present invention. Such adjuvants include, but are not limited to, Freund's incomplete adjuvant, Freund's complete adjuvant, polydispersed β-(1,4) linked acetylated mannan ("Acemannan"), TITERMAX® (polyoxyethylene-polyoxypropylene copolymer adjuvants from CytRx Corporation), modified lipid adjuvants from Chiron Corporation, saponin derivative adjuvants from Cambridge Biotech, killed *Bordetella pertussis*, the lipopolysaccharide (LPS) of gram-negative bacteria, large polymeric anions such as dextran sulfate, and inorganic gels such as alum, aluminum hydroxide, or aluminum phosphate.

Carrier proteins that can be used in the supramolecular antigenic construct compositions of the present invention include, but are not limited to, maltose binding protein "MBP"; bovine serum albumin "BSA"; keyhole lympet hemocyanin "KLH"; ovalbumin; flagellin; thyroglobulin; serum albumin of any species; gamma globulin of any species; syngeneic cells; syngeneic cells bearing Ia antigens; and polymers of D- and/or L-amino acids.

Further, the term "therapeutically effective amount" refers to the amount of antibody which, when administered to a human or animal, elicits an immune response which is sufficient to result in a therapeutic effect in said human or animal. The effective amount is readily determined by one of skill in the art following routine procedures.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

The term "hybridize" as used refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 70° C., preferably at 65° C. (regarding the definition of SSPE, SSC and Denhardts solution see Sambrook et al. loc. cit.). Stringent hybridization conditions as for instance described in Sambrook et al, supra, are particularly preferred. Particularly preferred stringent hybridization conditions are for instance present if hybridization and washing occur at 65° C. as indicated above. Non-stringent hybridization conditions, for instance with hybridization and washing carried out at 45° C. are less preferred and at 35° C. even less.

The present invention may be understood more readily by reference to the following detailed description of specific embodiments included herein. Although the present invention has been described with reference to specific details of certain embodiments, thereof, it is not intended that such details should be regarded as limitations upon the scope of the invention.

The present invention provides antibodies and functional parts thereof which are conformationally sensitive antibodies. These antibodies recognize specific epitopes on a wide variety of amyloid proteinic antigens. The antibodies are useful for diagnostic and therapeutic intervention in diseases and diseases and disorders which are caused by or associated with amyloid or amyloid-like proteins including amyloidosis, a group of diseases and disorders associated with amyloid or amyloid-like protein such as the Aβ protein involved in Alzheimer's Disease Antibodies are administered to individuals to passively immunize them against a variety of diseases or disorders, including but not limited to, diseases associated with amyloid protein such as Alzheimer's disease.

The antibodies provided herein are monoclonal or polyclonal antibodies having binding specificity for antigenic peptides representative of various disorders which are associated with amyloid protein such as, for example, Alzheimer's disease.

The antibodies according to the invention are prepared by immunizing an animal, such as a mouse, rat, rabbit or any other animal species which can produce native or human antibodies, with a supramolecular antigenic construct composition.

The supramolecular antigenic constructs as disclosed herein generally comprise peptides modified to enhance antigenic effect wherein such peptides are modified via pegylation (using polyethylene glycol or modified polyethylene glycol), or modified via other methods such as by palmitic acid, poly-amino acids (eg poly-glycine, poly-histidine), poly-saccharides (eg polygalacturonic acid, polylactic acid, polyglycolide, chitin, chitosan), synthetic polymers (polyamides, polyurethanes, polyesters) or co-polymers (eg. poly(methacrylic acid) and N-(2-hydroxy) propyl methacrylamide) and the like.

Modification by palmitic acid (palmitoylation), while providing an anchor for the peptide in the liposome bilayer, due to the relative reduced length of the $C_{16:0}$ fatty acid moiety leads to the peptide practically laying on the liposome surface. Therefore, the cells processing the antigen will have to take up the entire liposome with the peptide, which, in the majority of cases, results in a slower immune response in relative terms.

In one embodiment of the invention, a modified amyloid 1-15 peptide is used in the preparation of an antibody, particularly a monoclonal antibody according to the invention. The modified amyloid 1-15 peptide may be synthesized following the method reported in Nicolau et. al. 2002. The approach reported in Nicolau et al involves modifying the antigenic peptide by an on-resin grafting of a lipophilic or hydrophobic moiety, to the terminal amino acid residues of a pre-formed peptide resulting in a product of considerably high purity. In particular, a protected amino acid, particularly a Fmoc-protected amino acid, is attached to a resin using known coupling chemistry. The protecting group is removed and a second protected amino acid residue coupled. Standard automated peptide synthesis using known protection chemistry, particularly Fmoc/tBu chemistry, and standard side-chain protecting groups are then used to synthesis the $A\beta_{1-15}$ antigenic peptide by coupling on amino acids 1 to 15 of amyloid protein A $\beta_{1-42}$ to produce the peptide fragment with a sequence given in SEQ ID NO: 1. In a final step two further protected amino acids are coupled to the growing peptide fragment. The Mtt groups can then be selectively cleaved and coupled to palmitic acid. After washing of the resin, the protecting group is removed and the resin simultaneously cleaved, followed by side-chain deprotections using standard methodology. The final product can then be obtained in high purity and its identity confirmed by methods known in the art such as, for example, electrospray mass spectrometry.

The lipophilic or hydrophobic moiety according to the present invention may be a fatty acid, a triglyceride or a phospholipid wherein the fatty acid carbon back bone has at least 10 carbon atoms. Particularly, the lipophilic or hydrophobic moiety is a fatty acids with a carbon backbone of at least approximately 14 carbon atoms and up to approximately 24 carbon atoms, with each individual number of carbon atom falling within this range also being part of the present invention. More particularly, the lipophilic or hydrophobic moiety has a carbon backbone of at least 14 carbon atoms. Examples of hydrophobic moieties include, but are not limited to, palmitic acid, stearic acid, myristic acid, lauric acid, oleic acid, linoleic acid, linolenic acid and cholesterol or DSPE. In a specific embodiment of the present invention the lipophilic or hydrophobic moiety is palmitic acid.

To enhance the immune response, another anchor/spacer can suitably be applied to reconstitute the peptide in the liposome, e.g. polyethylene glycol (PEG).

PEG is covalently attached to an amino acid residue bound at both termini of the peptide, in particular Glu, Cys or Lys amino acid residue or any other amino acid residue that can be suitably used to covalently bind PEG to the peptide. At the other end of the chain a hydrophobic moiety may be covalently bound to function as the anchoring element in the liposome bilayer such as, for example, phosphatidyl ethanol amine (PEA). Thus, the liposome still functions as an adjuvant and the peptide being sufficiently far away from the bilayer can be processed alone and thus increases its immunogenicity as compared to the palmitoylated antigen.

In certain embodiments, the supramolecular antigenic constructs used within the scope of the present invention comprise a peptide sequence, covalently attached to pegylated lysine—one at each terminus. The length of the PEG (polyethyleneglycol) chain may vary from n=8 to n=150.000 or more, particularly from n=10 to n=80.000, more particularly from n=20 to n=10.000. In a specific embodiment of the invention the length of the PEG chain is not more than n=45, particularly between n=5 and n=40, more particularly between n=10 and n=30, and even more particularly n=10.

The supramolecular constructs described herein can be synthesized using automated peptide synthesis and known protection chemistry, particularly Fmoc/tBu chemistry and standard side-chain protecting groups. Typically, pegylation of peptides results in mixtures of regioisomers.

To achieve a site-specific attachment of a PEG-lipid conjugate to both the C- and N-terminus of Aβ partially protected peptides may be used. For those peptide sequences containing internal Lys or His residues an orthogonally protected Lys (ivDde) is added to each terminus. An additional Gly may be added to the C-terminal end to facilitate synthesis. The protecting group is removed and N-acetylated using acetic anhydride followed by selective cleavage of the ivDde groups.

A resin, particularly a 2-chlorotrityl resin, is to be favored which is acid sensitive and thus enables the isolation of protected peptides.

In a specific embodiment of the invention, the coupling reaction is performed in the solution phase. Selective cleavage from the resin under mild conditions then release the internally protected peptides.

Solution-phase couplings were achieved successfully with the peptides derived from a β-amyloid protein sequence such as, for example, a $A\beta_{1-16}$ (SEQ ID NO: 2) to a PEG molecule modified by a fatty acid—phosphatidylcholine such as, for example, DSPE. Separation of the mono- and di-coupled products before final side-chain deprotections can be achieved by using cation-exchange chromatography. Subsequent peptide side-chain deprotections leads to the isolation of the desired conjugates with an acceptable purity. Purification can be achieved by methods well known in the art such as, for example, HPLC. etc.

This approach to the synthesis of N- and C-terminal lipid-PEG β-amyloid antigens using protected peptides is applicable to a wide variety of peptide sequences.

Liposomal antigens according to the invention may then be prepared as described in Nicolau et al., 2002. The modified amyloid Aβ antigenic peptide, particularly the modified PEG- and palmitoylated $A\beta_{1-15}$, $A\beta_{1-16}$, $A\beta_{1-16(\Delta 14)}$, $A\beta_{22-35}$ and $A\beta_{29-40}$ antigenic peptide may be reconstituted in a construct consisting of liposomes, particularly liposomes made of dimyristoyl phosphatidyl choline (DMPC), dimyristoyl phosphatidyl ethanolamine (DMPEA), dimyristoyl phosphatidyl glycerol (DMPG) and cholesterol, optionally containing monophosphoryl lipid A.

In a specific embodiment of the invention liposomes with lipid A are used as adjuvant to prepare the anti-amyloid vaccine. Dimyristoylphosphatidyl-choline, -glycerol and cholesterol are mixed, particularly in a molar ratio of 0.9:1.0:0.7. A strong immunomodulator such as, for example, monophosphoryl lipid A is then added at a suitable concentration, particularly at a concentration of between 30 and 50 mg per mmol, more particularly at 40 mg per mmol of phospholipids. The modified antigenic Aβ peptide is then added at a molar ratio peptide to phospholipids of between 1:30 and 1:200, particularly at a molar ratio of between 1:50 and 1:120, more particularly of 1:100. Solvents are removed, for example through evaporation, and the resulting film hydrated with sterile buffer solution such as, for example PBS.

Liposomes may also be prepared by the crossflow injection technique as described, for example, in Wagner et al (2002) Journal of Liposome Research Vol 12(3), pp 259-270. During the injection of lipid solutions into an aqueous buffer system, lipids tend to form "precipitates", followed by self arrangement in vesicles. The obtained vesicle size depends on factors such as lipid concentration, stirring rate, injection rate, and the choice of lipids. The preparation system may consist of a crossflow injection module, vessels for the polar phase (e.g. a PBS buffer solution), an ethanol/lipid solution vessel and a pressure device, but particularly a nitrogen pressure device. While the aqueous or polar solution is pumped through the crossflow injection module the ethanol/lipid solution is injected into the polar phase with varying pressures applied.

The liposome still functions as an adjuvant and the peptide being sufficiently far away from the bilayer can be processed alone and thus increases its immunogenicity as compared to the palmitoylated antigen.

The free PEG terminus is covalently attached to a molecule of phosphatidyl-ethanolamine (where the fatty acid can be: myristic, palmitic, stearic, oleic etc. or a combination thereof) to function as the anchoring element. This supramolecular structure may be anchored by reconstitution in liposomes consisting of phospholipids and cholesterol (phosphatidylethanol amine, phosphatidyl glycerol, cholesterol in varied molar ratios. Other phospholipids can be used. Lipid A is used at a concentration of approximately 40 □g/pmole of phospholipids.

In certain embodiments, the palmitoylated or pegylated supramolecular antigenic constructs comprise a peptide having the amino acid sequence of β-amyloid. The peptides may also comprise or correspond to whole amyloid beta peptide and active fragments thereof. Additionally, peptides useful for the present invention further comprise $A\beta_{1-16}$ (SEQ ID NO: 2); $A\beta_{1-16(\Delta 14)}$; (SEQ ID NO: 3); $A\beta_{1-15}$ (SEQ ID NO: 1); and active fragments thereof.

For eliciting and preparing antibodies and for determining immunogenicity of the modified Aβ antigenic construct a suitable animal selected from the group consisting of mice, rats, rabbits, pigs, birds, etc, but particularly mice, especially C57BL/6 mice are immunized with the antigenic peptide. Immunogenicity of the antigenic construct is determined by probing Sera samples in suitable time intervals after immunization using a immunoassay such as, for example, an ELISA assay.

The monoclonal antibodies of the present invention can be prepared using classical cloning and cell fusion techniques well known in the art. The immunogen (antigen) of interest, is typically administered (e.g. intraperitoneal injection) to wild type or inbred mice (e.g. BALB/c or especially C57BL/6 mice), rats, rabbits or other animal species or transgenic mice which can produce native or human antibodies. The immunogen can be administered alone, or mixed with adjuvant, or expressed from a vector (VEE replicon vector, vaccinia), or as DNA, or as a fusion protein to induce an immune response. Fusion proteins comprise the peptide against which an immune response is desired coupled to carrier proteins, such as, for example, beta.-galactosidase, glutathione S-transferase, keyhole limpet hemocyanin (KLH), and bovine serum albumin. In these cases, the peptides serve as haptens with the carrier proteins. After the animal is boosted, for example, two or more times, spleen cells are harvested from the immunized animals and hybridomas generated by fusing sensitized spleen cells with a myeloma cell line, such as murine SP2/O myeloma cells (ATCC, Manassas, Va.) using the well-known processes of Kohler and Milstein (Nature 256: 495-497 (1975)) and Harlow and Lane (Antibodies: A Laboratory Manual (Cold Spring Harbor Laboratory, New York 1988)).

In a specific embodiment of the invention the antigenic construct according to the invention, particularly a vaccine composition comprising said antigenic construct in a pharmaceutically acceptable form, is administered in repeated doses, in particular in 1 to 15 doses, more particularly in 2 to 10 doses, even more particularly in 3 to 7 doses but especially in 4 to 6 doses, in time intervals of between 1 and 10 weeks, particularly in time intervals of between 1 and 6 weeks, more particularly in time intervals of between 1 and 4 weeks, and even more particularly in time intervals of between 2 and 3 weeks. The immune response is monitored by taking Sera samples at a suitable time after boosting, particularly 3 to 10 days after boosting, more particularly 4 to 8 days after boosting and more particularly 5 to 6 days after boosting and determining the immunogenicity of the antigenic construct using known methodology, particularly one of the commonly used immunoassays such as, for example, an ELISA assay Immunization with the antigenic construct according to the invention, but particularly with a vaccine composition comprising the antigenic construct according to the invention in a pharmaceutically acceptable form leads to a significant immune response in the treated animal. Animals, but especially mice with therapeutic titers are selected for a fusion of antibody producing cells, particularly B-lymphocytes with a continuously growing or immortal cell line, such as a myeloma cell line. The cells are induced to fuse by the addition of polyethylene glycol. Therapeutic titers are those which give a positive result in an ELISA assay in a dilution of between 1:4000 and 1:6000, particularly of between 1:4500 and 1:5500, more particularly of 1:5000.

The resulting hybrid cells are then cloned in the conventional manner, e.g. using limiting dilution, and the resulting clones, which produce the desired monoclonal antibodies, cultured.

The so obtained hybridomas are chemically selected by plating the cells in a selection medium containing hypoxanthine, aminopterin and thymidine (HAT).

Hybridomas are subsequently screened for the ability to produce monoclonal antibodies against specific amyloid-associated diseases or disorders. Hybridomas producing antibodies of interest are cloned, expanded and stored frozen for future production. The preferred hybridoma produces a monoclonal antibody having the IgG isotype, more preferably the IgG2 isotype.

The polyclonal antibody is prepared by immunizing animals, such as mice or rabbits, or any other suitable animal with supramolecular antigenic construct compositions of the present invention described above. Blood sera is subsequently collected from the animals, and antibodies in the sera screened for binding reactivity against the amyloid antigen.

The antibodies according to the invention can be prepared in a physiologically acceptable formulation and may comprise a pharmaceutically acceptable carrier, diluent and/or excipient using known techniques. For example, the antibody according to the invention and as described herein before including any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc.

Formulation of the pharmaceutical composition according to the invention can be accomplished according to standard methodology know to those skilled in the art.

The compositions of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It is well known to those skilled in the pertinent art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The composition may be administered in combination with other compositions comprising an biologically active substance or compound, particularly at least one compound selected from the group consisting of compounds against oxidative stress, anti-apoptotic compounds, metal chelators, inhibitors of DNA repair such as pirenzepine and metabolites, 3-amino-1-propanesulfonic acid (3APS), 1,3-propanedisulfonate (1,3PDS), secretase activators, β- and γ-secretase inhibitors, tau proteins, neurotransmitter, β-sheet breakers, anti-inflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B12, cystein, a precursor of acetylcholine, lecithin, cholin, *Ginkgo biloba*, acetyl-L-carnitine, idebenone, propentofylline, or a xanthine derivative, together with an antibody according to the present invention and, optionally, a pharmaceutically acceptable carrier and/or a diluent and/or an excipient and procedures for the treatment of diseases.

Proteinaceous pharmaceutically active matter may be present in amounts between 1 ng and 10 mg per dose. Generally, the regime of administration should be in the range of between 0.1 μg and 10 mg of the antibody according to the invention, particularly in a range 1.0 μg to 1.0 mg, and more particularly in a range of between 1.0 μg and 100 μg, with all individual numbers falling within these ranges also being part of the invention. If the administration occurs through continuous infusion a more proper dosage may be in the range of between 0.01 μg and 10 mg units per kilogram of body weight per hour with all individual numbers falling within these ranges also being part of the invention.

Administration will generally be parenterally, eg intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The pharmaceutical composition may further comprise proteinaceous carriers such as, for example, serum albumine or immunoglobuline, particularly of human origin. Further biologically active agents may be present in the pharmaceutical composition of the invention dependent on its the intended use.

In a further embodiment the present invention provides methods and kits for the detection and diagnosis of amyloid-associated diseases or conditions, for diagnosing a predisposition to an amyloid-associated disease or condition or for monitoring minimal residual disease in a patient or for predicting responsiveness of a patient to a treatment with an antibody or a vaccine composition according to the invention and as described herein before. These methods include known immunological methods commonly used for detecting or quantifying substances in biological samples or in an in situ condition.

Diagnosis of an amyloid-associated disease or condition or of a predisposition to an amyloid-associated disease or condition in a patient may be achieved by detecting the immunospecific binding of a monoclonal antibody or an active fragment thereof to an epitope of the amyloid protein in a sample or in situ, which includes bringing the sample or a specific body part or body area suspected to contain the amyloid antigen into contact with an antibody which binds an epitope of the amyloid protein, allowing the antibody to bind to the amyloid antigen to form an immunological complex, detecting the formation of the immunological complex and correlating the presence or absence of the immunological complex with the presence or absence of amyloid antigen in the sample or specific body part or area, optionally comparing the amount of said immunological complex to a normal control value, wherein an increase in the amount of said aggregate compared to a normal control value indicates that said patient is suffering from or is at risk of developing an amyloid-associated disease or condition.

Monitoring minimal residual disease in a patient following treatment with an antibody or a vaccine composition according to the invention may be achieved by detecting the immunospecific binding of a monoclonal antibody or an active fragment thereof to an epitope of the amyloid protein in a sample or in situ, which includes bringing the sample or a specific body part or body area suspected to contain the amyloid antigen into contact with an antibody which binds an epitope of the amyloid protein, allowing the antibody to bind to the amyloid antigen to form an immunological complex, detecting the formation of the immunological complex and correlating the presence or absence of the immunological complex with the presence or absence of amyloid antigen in the sample or specific body part or area, optionally comparing the amount of said immunological complex to a normal control value, wherein an increase in the amount of said aggregate compared to a normal control value indicates that said patient may still suffer from a minimal residual disease.

Predicting responsiveness of a patient to a treatment with a vaccine composition according to the invention may be achieved by detecting the immunospecific binding of a monoclonal antibody or an active fragment thereof to an epitope of the amyloid protein in a sample or in situ, which includes bringing the sample or a specific body part or body area suspected to contain the amyloid antigen into contact with an antibody which binds an epitope of the amyloid protein, allowing the antibody to bind to the amyloid antigen to form an immunological complex, detecting the formation of the immunological complex and correlating the presence or absence of the immunological complex with the presence or absence of amyloid antigen in the sample or specific body part or area, optionally comparing the amount of said immunological complex before and after onset of the treatment, wherein an decrease in the amount of said aggregate indicates that said patient has a high potential of being responsive to the treatment.

Biological samples that may be used in the diagnosis of an amyloid-associated disease or condition, for diagnosing a predisposition to an amyloid-associated disease or condition or for monitoring minimal residual disease in a patient or for predicting responsiveness of a patient to a treatment with an antibody or a vaccine composition according to the invention and as described herein before are, for example, fluids such as serum, plasma, saliva, gastric secretions, mucus, cerebrospinal fluid, lymphatic fluid and the like or tissue or cell samples obtained from an organism such as neural, brain, cardiac or vascular tissue. For determining the presence or absence of the amyloid antigen in a sample any immunoassay known to those of ordinary skill in the art. (See Harlow and Lane, Antibodies: A Laboratory Manual (Cold Spring Harbor Laboratory, New York 1988 555-612) may be used such as, for example, assays which utilize indirect detection methods using secondary reagents for detection, ELISA's and immunoprecipitation and agglutination assays. A detailed description of these assays is, for example, given in WO96/13590 to Maertens and Stuyver, Zrein et al. (1998) and WO96/29605.

For in situ diagnosis, the antibody or any active and functional part thereof may be administered to the organism to be diagnosed by methods known in the art such as, for example, intravenous, intranasal, intraperitoneal, intracerebral, intraarterial injection such that a specific binding between the antibody according to the invention with an epitopic region on the amyloid antigen may occur. The antibody/antigen complex may be detected through a label attached to the antibody or a functional fragment thereof.

The immunoassays used in diagnostic applications or in applications for diagnosing a predisposition to an amyloid-associated disease or condition or for monitoring minimal residual disease in a patient or for predicting responsiveness of a patient to a treatment with an antibody or a vaccine composition according to the invention and as described herein before. typically rely on labelled antigens, antibodies, or secondary reagents for detection. These proteins or reagents can be labelled with compounds generally known to those skilled in the art including enzymes, radioisotopes, and fluorescent, luminescent and chromogenic substances including colored particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Antibodies useful in these assays include monoclonal antibodies, polyclonal antibodies, and affinity purified polyclonal antibodies.

Alternatively, the antibody may be labelled indirectly by reaction with labelled substances that have an affinity for immunoglobulin, such as protein A or G or second antibodies. The antibody may be conjugated with a second substance and detected with a labelled third substance having an affinity for the second substance conjugated to the antibody. For example, the antibody may be conjugated to biotin and the antibody-biotin conjugate detected using labelled avidin or streptavidin. Similarly, the antibody may be conjugated to a hapten and the antibody-hapten conjugate detected using labelled anti-hapten antibody.

Those of ordinary skill in the art will know of these and other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 81:1-40). Coupling techniques mentioned in the latter are the glutaraldehyde method, the periodate method, the dimaleimide method, and others, all of which are incorporated by reference herein.

Current immunoassays utilize a double antibody method for detecting the presence of an analyte, wherein. the antibody is labeled indirectly by reactivity with a second antibody that has been labeled with a detectable label. The second antibody is preferably one that binds to antibodies of the animal from which the monoclonal antibody is derived. In other words, if the monoclonal antibody is a mouse antibody, then the labeled, second antibody is an anti-mouse antibody. For the monoclonal antibody to be used in the assay described below, this label is preferably an antibody-coated bead, particularly a magnetic bead. For the polyclonal antibody to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antibody and the analyte. According to one embodiment of the present invention, the presence of the amyloid antigen is determined using a pair of antibodies, each specific for amyloid antigen. One of said pairs of antibodies is referred to herein as a "detector antibody" and the other of said pair of antibodies is referred to herein as a "capture antibody". The monoclonal antibody of the present invention can be used as either a capture antibody or a detector antibody. The monoclonal antibody of the present invention can also be used as both capture and detector antibody, together in a single assay. One embodiment of the present invention thus uses the double antibody sandwich method for detecting amyloid antigen in a sample of biological fluid. In this method, the analyte (amyloid antigen) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antibodies to solid phases are also well known to those skilled in the art. More recently, a number of porous material such as nylon, nitrocellulose, cellulose acetate, glass fibers and other porous polymers have been employed as solid supports.

The present invention also relates to a diagnostic kit for detecting amyloid antigen in a biological sample comprising a composition as defined above. Moreover, the present invention relates to the latter diagnostic kit which, in addition to a composition as defined above, also comprises a detection reagent as defined above. The term "diagnostic kit" refers in general to any diagnostic kit known in the art. More specifically, the latter term refers to a diagnostic kit as described in Zrein et al. (1998).

It is still another object of the present invention to provide novel immunoprobes and test kits for detection and diagnosis of amyloid-associated diseases and conditions comprising antibodies according to the present invention. For immunoprobes, the antibodies are directly or indirectly attached to a suitable reporter molecule, e.g., an enzyme or a radionuclide. The test kit includes a container holding one or more antibodies according to the present invention and instructions for using the antibodies for the purpose of binding to amyloid antigen to form an immunological complex and detecting the formation of the immunological complex such that presence or absence of the immunological complex correlates with presence or absence of amyloid antigen.

EXAMPLES

Antigens Used to Raise Mouse Monoclonal Antibodies

TABLE 1

Antibodies and antigenic constructs used for raising said antibodies

| Mouse mAb | Antigen/Sequence | Linker | Anchor | Adjuvant |
|---|---|---|---|---|
| mACI-01-Ab7 | $A\beta_{1-16}$ | PEG | DSPE | Lipid A |
| mACI-02-Ab6 | $A\beta_{1-16(\Delta 14)}$ | PEG | DSPE | Lipid A |
| mACI-11-Ab9 | $A\beta_{22-35}$ | PEG | DSPE | Lipid A |
| mACI-12-Ab11 | $A\beta_{29-40}$ | PEG | DSPE | Lipid A |
| mACI-24-Ab4 | $A\beta_{1-15}$ | — | Palm | Lipid A |

Example 1

Methods for Making Palmitoylated $A\beta_{1-15}$ Supramolecular Antigenic Constructs Synthesis of Tetra(Palmitoyl Lysine)-Aβ1-15 Peptide Antigen:

The palmitoylated amyloid 1-15 peptide was synthesized following an improved previously reported method (Nicolau et. al. 2002). This new approach involved on-resin grafting of palmitic acid to the terminal Lys residues of the pre-formed peptide rather than stepwise solid-phase synthesis incorporating the modified amino acid 9-fluorenylmethoxycarbonyl (Fmoc)-Lys(Pal)-OH. This new approach improves coupling efficiency and gives a product of considerably higher purity. Thus, the orthogonally protected amino acid Fmoc-Lys(Mtt)-OH was attached to a Wang resin using [2-(1H-benzotriazol-1-yl)-1,1,3,3-tetramethyluronium hexafluorophosphate] (HBTU) coupling chemistry. The Fmoc group was removed using 20% piperidine in DMF and a second residue of Fmoc-Lys(Mtt)-OH was coupled. Standard automated peptide synthesis using Fmoc/tBu chemistry and standard side-chain protecting groups was then used to couple on the next 15 amino acids to yield a peptide sequence as given in SEQ ID NOS: 1. Finally, the last two amino acids coupled were Fmoc-Lys(Mtt)-OH. The Mtt groups were then selectively cleaved using 1% trifluoroacetic acid (TFA) in dichloromethane to release a peptide fragment and then coupled to palmitic acid using HBTU. After resin wash, the Fmoc group was removed with 20% piperidine in dimethylformamide (DMF) and finally simultaneous resin cleavage and side-chain deprotections were carried out using TFA under standard conditions.

Trituration from cold diethyl ether gave the product as a white solid. Electrospray mass spectrometry confirmed the identity of the product (m/z expected: 1097.9 ([M]3+); found: 1096.8 ([M-3H]3+), with no other tri-, di- or mono-palmitoylated peptides detected.

Example 2

Methods for Making Supramolecular Antigenic Constructs

Synthesis of Pegylated β-Amyloid Peptide Antigen:

To enhance the immune response, another anchor/spacer has been applied to reconstitute the peptide in the liposome, e.g. polyethylene glycol (PEG). PEG was covalently attached to the lysine residue bound at both termini of the peptide. At the other end of the chain (PEGn=70) phosphatidyl ethanol amine (PEA) was covalently bound to function as the anchoring element in the liposome bilayer. Thus, the liposome still functions as an adjuvant and the peptide being sufficiently far away from the bilayer can be processed alone and thus increases its immunogenicity as compared to the palmitoylated antigen.

The supramolecular constructs described herein were uniquely synthesized using standard Fmoc/tBu amino acid side-chain protections. Typically, pegylation of peptides results in mixtures of regioisomers. Herein a convenient method for the site-specific attachment of a PEG-lipid conjugate to both the C- and N-terminus of Aβ is demonstrated using partially protected peptides.

For those peptide sequences containing internal Lys or His residues (1-16, 1-16Δ14, 22-35), an orthogonally protected Lys(ivDde) was added to each terminus. An additional Gly was added to the C-terminal to facilitate synthesis. The Fmoc group was removed with 20% piperidine in DMF and N-acetylated using acetic anhydride. Selective cleavage of the ivDde groups was achieved with 3% hydrazine hydrate in DMF for one hour. The 2-chlorotrityl resin was favored over the more widely used Wang resin since the former proved to be much more resistant to hydrazinolysis. Furthermore, the 2-chlorotrityl resin is extremely acid sensitive and thus, unlike the Wang resin, enables the isolation of protected peptides. Indeed, it was necessary to perform the coupling reaction in the solution phase as coupling of the resin-bound peptide to the pre-activated pegylated lipid reagent DSPE-PEG-SPA did not give rise to any coupling product. Thus selective cleavage from the resin under mild conditions (acetic acid/trifluoroethanol/dichloromethane, 1:1:8, 1 h, rt) gave the internally protected peptides.

Solution-phase couplings were achieved successfully with the peptides derived from sequence $A\beta_{1-16}$ (SEQ ID NO: 2) to DSPE-PEG-SPA in DMSO and excess base. The reactions were then quenched by the addition of excess ethanolamine for 2 h and the solution lyophilized.

For the sequence 29-40, no special protection strategy is required.

Purification by HPLC (semi-preparative reverse-phase $C_4$ column) gave between 50-70% purity of the N- and C-terminal PEG-lipid conjugates whose identities were confirmed by MALDI (matrix assisted laser desorption ionization). Each sequence showed considerable variation in the ease of the coupling reaction and conditions were adjusted accordingly (temperature, number of molar equivalents DSPE-PEG-SPA, time). For the separation of excess DSPE-PEG-SPA from the desired product HPLC purification is applied. Separation of the mono- and di-coupled products before final side-chain deprotections can be achieved by using cation-exchange chromatography. Subsequent peptide side-chain deprotections and separation of the excess quenched DSPE-PEG-SPA leads to the isolation of the desired conjugates with an acceptable purity.

This approach to the synthesis of N- and C-terminal lipid-PEG β-amyloid antigens using protected peptides is applicable to a wide variety of peptide sequences.

Example 3

Antibodies Elicited by Supramolecular Antigenic Constructs

Manufacturing of mAbs Raised Against Palmitoylated $A\beta_{1-15}$ Supramolecular Antigenic Construct:

Palmitoylated antigen (ACI-24, $A\beta_{1-15}$) was used for the immunization in C57BL/6 mice in 2 week intervals. 10-12 animals were immunized with each antigen (Injection vol: 200 µl containing 8 nmoles peptid). Last injection was performed 4 days before sacrifice of the animals. After 5 boostings mice with therapeutic titers (when a 1:5,000 dilution of the sera were positive in ELISA) were selected for a fusion. Spleen cells are harvested from the immunized animals and hybridomas generated by fusing sensitized spleen cells with a myeloma cell line. The fusion of the mice's B-lymphocytes from the spleens was conducted with cells of myeloma cell line SP2-0. (ATCC, Manassas, Va.) using the well-known processes of Kohler and Milstein (Nature 256: 495-497 (1975)) and Harlow and Lane (Antibodies: A Laboratory Manual (Cold Spring Harbor Laboratory, New York 1988)).

The cells are induced to fuse by the addition of polyethylene glycol. The resulting hybrid cells are then cultured for 10±14 day in the conventional manner to allow clonal growth. Initial clonal selection was made using limiting dilution. IgG producing hybridoma clones were selected and tested for their specific binding to the $A\beta_{1-42}$ peptide by ELISA and the resulting clones, which produce the desired monoclonal antibodies, cultured.

The so obtained hybridomas are chemically selected by plating the cells in a selection medium containing hypoxanthine, aminopterin and thymidine (HAT).

Hybridomas are subsequently screened for the ability to produce monoclonal antibodies against specific amyloid-associated diseases or disorders. Once the mother clone was identified, it was subcloned four times to assure monoclonality and allow the hybrid to stabilize.

Hybridomas producing antibodies of interest are cloned, expanded and stored frozen for future production.

The antibody was isotyped by a commercially available mouse monoclonal isotyping kit and the stable clone was adapted to serum free medium and placed in a bioreactor for antibody production.

The preferred hybridoma produces a monoclonal antibody having the IgG isotype, more preferably the IgG1 isotype.

Manufacturing of mAbs raised against Pegylated PEG-$A\beta_{1-16}$, $A\beta_{4-11}$, $A\beta_{22-35}$ and $A\beta_{29-40}$ Supramolecular Antigenic Constructs:

Liposomal antigens were prepared as described (Nicolau et al., 2002, PNAS, 99, 2332-37). The sequences PEG-$A\beta_{1-16}$, $A\beta_{4-11}$, $A\beta_{22-35}$ and $A\beta_{29-40}$ (FIG. 1) were reconstituted in a construct consisting of liposomes made of dimyristoyl phosphatidyl choline (DMPC), dimyristoyl phosphatidyl ethanolamine (DMPEA), dimyristoyl phosphatidyl glycerol (DMPG) and cholesterol (0.9:0.1:0.1:0.7 molar ratios) containing monophosphoryl lipid A (40 mg/mM phospholipids). These antigens and pegylated $A\beta_{1-16}$ were used for the immunization in C57BL/6 mice in 2 week intervals. 10-12 animals were immunized with each antigen. After 3 to 6 boostings, mice with therapeutic titers (when a 1:5,000 dilution of the sera were positive in ELISA) were selected for a fusion. Spleen cells are harvested from the immunized animals and hybridomas generated by fusing sensitized spleen cells with a myeloma cell line. The fusion of the mice's B-lymphocytes from the spleens was conducted with cells of myeloma cell line SP2-0. (ATCC, Manassas, Va.) using the well-known processes of Kohler and Milstein (Nature 256: 495-497 (1975)) and Harlow and Lane (Antibodies: A Laboratory Manual (Cold Spring Harbor Laboratory, New York 1988)).

The cells are induced to fuse by the addition of polyethylene glycol. The resulting hybrid cells are then cloned in the conventional manner, e.g. using limiting dilution. IgG producing hybridoma clones were selected and tested for their specific binding to the $A\beta_{1-42}$ peptide by ELISA and the resulting clones, which produce the desired monoclonal antibodies, cultured.

The so obtained hybridomas are chemically selected by plating the cells in a selection medium containing hypoxanthine, aminopterin and thymidine (HAT).

Hybridomas are subsequently screened for the ability to produce monoclonal antibodies against specific amyloid-associated diseases or disorders. Hybridomas producing antibodies of interest are cloned, expanded and stored frozen for future production. The preferred hybridoma produces a monoclonal antibody having the IgG isotype, more preferably the IgG1 isotype.

Example 4

Specificity Determination for Antibody mACI-24-Ab4

To analyze the specificity of the antibody mACI-24-Ab4, different concentrations of pre-formed Amyloid 1-42, 1-40 and 1-38 fibrils were blotted onto Hybond ECL Nitrocellulose Membrane (Amersham Biosciences). After blocking with 10% dry milk and 0.7% Tween 20, membranes were incubated with primary antibody at 20 µg/ml for 2 h at RT. After washing, membranes were incubated with horse radish peroxidase conjugated sheep anti-mouse IgG antibody (Amersham Biosciences) for 1 h at RT, washed and incubated with chemiluminescent solution followed by the exposure of the membrane to X-ray film.

To measure binding of the mAb mACI-24-Ab4 to amyloid β 1-42 fibers, Aβ 1-42, 1-40 and 1-38 fibers were pre-formed for seven days at 37° C. and blotted on the membrane. 20 µg/ml antibody was used to measure binding capacity and the bound antibody was detected by horse radish peroxidase conjugated sheep anti-mouse IgG antibody for 20 minutes exposition.

As it could be demonstrated by Dot Blot analysis, the antibody mACI-24-Ab4 binds to different pre-formed Aβ fibers with different sensitiveness. The antibody exhibits the highest binding sensitivity to $A\beta_{1-42}$ fibers than for $A\beta_{1-40}$ or $A\beta_{1-38}$. It is able to detect at least 0.001 µg of $A\beta_{1-42}$ fibers whereas the detection limit of the antibody for $A\beta_{1-40}$ fibers is at least 0.1 µg and for the $A\beta_{1-38}$ fibers 1 µg, meaning the sensitiveness is 100 fold to a 1000 fold less for these types of amyloid fibers. These data demonstrates that the antibody ACI-24-Ab4 is at least a 100 fold more sensitive to the amyloid form (1-42) which is known to become insoluble by change of secondary conformation and being major part of amyloid plaques in brains of AD patients.

Example 5

Binding of AC Immune's Monoclonal Antibody mACI-01-Ab7 C2 to Amyloid Species in Western Blot and Dot Blot To determine whether the binding of the mouse antibody mACI-01-Ab7 C2 is dependent on the native conformation of Aβ a comparison of the binding to linearized amyloid by Western Blot or native amyloid on Dot Blot was performed (FIGS. 2a and 2b)

Amyloid monomers were generated by dissolving Aβ1-42 peptide in HFIP and the solvent evaporated under argon. Dried peptide film was stored at −80° C. until use. For preparation of monomers, the peptide film was resuspended in DMSO to a concentration of 2.75 µg/µl and diluted in PBS to 5 µg/µl. For preparation of oligomers, dried peptide film was resuspended in DMSO to 5 mM, sonicated and PBS added to reach 400 uM amyloid followed by the addition of SDS to a final concentration of 0.2%. After 6 hour incubation at 37° C., the amyloid was diluted in water to a final concentration of 100 µM and incubated another 18 h at 37° C. The amyloid oligomers were precipitated with ice-cold 33% methanol, 4% acetic acid solution for 1 h at 4° C., spun down at 16200 g for 10 minutes and the pellet resuspended in 5 mM Na2H2PO4, 35 mM NaCl pH 7.4 to a final concentration of 1 µg/µl. For preparation of fibers, peptide film was diluted in Tris-HCl 50 mM buffer to get a concentration of 1 mg/ml of amyloid and incubated at 37° C. for 5 days. The tubes were spun at 10000 g for 5 minutes and the pellet resuspended in 0.1 M carbonate buffer pH 9.6 to reach 1 µg/µl.

1 or 5 µg of monomers, oligomers or fibers were diluted in PBS and in loading buffer and applied to a 12% SDS-PAGE and the gel transferred to nitrocellulose membranes. Alternatively, 3 or 1 µg or 100 and 10 ng of amyloid species were diluted in PBS and were dotted directly onto the nitrocellulose membrane and the membranes dried at RT for 1 hour. After blocking for 30 minutes with Casein solution (Vector), the membranes were incubated for 30 minutes with mACI-01-Ab7 C2 or 6E10 (Chemicon) antibodies diluted to 1 µg/ml in Casein solution. After 3 washes in Casein solution, the membranes were incubated at RT for 30 minutes with HRP-labeled goat anti-mouse IgG (Dako Cytomation) diluted in Casein solution, washed 3 times and developed with DAB substrate (Dako Cytomation).

The monoclonal mouse antibody mACI-01-Ab7 C2 bound specifically to monomers, oligomers and fibers in the Dot Blot assay as did the positive control antibody 6E10. In contrast, the mACI-01-Ab7C2 antibody did not detect linearized amyloid species by Western Blot in contrast to the 6E10 antibody which clearly recognized all linearized peptides. This result demonstrates that the binding of mACI-01-Ab7 C2 to amyloid is dependent on the native conformation of amyloid.

Example 6 mACI-01Ab7 C2-$A\beta_{1-42}$ Interactions

The interactions between AC immune's lead antibody mACI-01-Ab7 C2 (mC2) with amyloid peptide $A\beta_{1-42}$ was studies using surface plasmon resonance. The binding of the mouse antibody mACI-01-Ab7 C2 to either monomers or fibers of $A\beta_{1-42}$ were determined.

All SPR experiments were carried out on a Biacore X instrument (Biacore AB). Reagents for immobilization (EDC, NHS and ethanolamine), sensor chips CM5 and SA as well as running and sample buffer HBS-EP were purchased from Biacore AB. Sodium acetate (10 mM, pH 5.0) was used as coupling buffer to increase coupling yield. Fibrillar $A\beta_{1-42}$ (BAchem) was prepared by adding PBS buffer to $A\beta_{1-42}$ to a final concentration of 3 mg/ml and leaving the vials at 37° C. for 7 days. Fibrillar $A\beta_{1-42}$ was coupled to a CM5 sensor chip containing a surface-bound carboxymethyl dextran matrix. Biotinylated monomeric $A\beta_{1-42}$ (Bachem) was coupled to a Sensor chip SA consisting of carboxymethyl dextran matrix with covalently attached Streptavidin. Typically four or five concentrations of mAb were assayed by serial dilutions using running buffer. Injections were performed starting from the lowest concentration and were passed over both fc 1 and 2 at a flow rate of 30 µL/min for 3 min. Flow cell 2 was underivatized and responses were subtracted from fc 1 to correct for instrument noise and bulk refractive changes. After injection was finished, the surfaces were washed immediately with running buffer for 5 min. To remove remaining bound antibody from the $A\beta_{1-42}$ fibrils, surface regeneration was performed by injecting pulses of 10 mM NaOH. Kinetic analysis was performed using algorithms for numerical integration and global analysis using BIAevaluation 3.0. The curves obtained for injections of analyte at different concentrations were overlaid and the baselines adjusted to zero. For curve fitting, all data were fit simultaneously to a 1:1 homogeneous complex.

Binding of the mouse mACI-01-Ab7 C2 antibody to amyloid was determined to be relatively strong. As demonstrated in Table 2, the mouse antibody mACI-01-Ab7 C2 bound specifically to immobilized $A\beta_{1-42}$ fibers with an average association constant (ka) of $3.8\times10^{-4}$ M/s, a dissociation constant (kd) of $1.1\times10^{-3}$ s$^{-1}$ and therefore with the resulting average KD of $3.5\times10^{-8}$ M. Association of the mACI-01-Ab7 C2 to $A\beta$ monomers was similar or slightly faster with an average ka of $1.6\times10^{-4}$ M/s but the dissociation was more rapid giving a KD of $2.5\times10^{-7}$ M.

of 1:100. Subsequently 5 µl of sample were incubated on the fresh glow-discharged Cu grid (mesh 200) covered with parlodium/C film for 45 seconds, washed 3 times with water and 1 times with 2% fresh diluted and filtered uranyl acetate. Samples were stained in 2% uranyl acetate for 15-20 sec. Excess of stain on the grids was sucked and consequently air-dried. Three grids of each sample were prepared. The grids were analyzed in transmission electron microscopy Hitachi 7000.

The monoclonal antibody, mACI-01-Ab7 C2, binds directly to $A\beta_{1-42}$ fibers. Interestingly the antibody exhibits no symmetric binding to axis of single fibers but binds to particular and not all areas of side branches of the fiber network. It seemed to be the antibody targets specific regions within the side branches. The potential explanation is a specific secondary structure which occurs only in this specific side branches. This hypothesis is supported by NMR data demonstrating that the antibody induced transition on conformation and therefore it is likely that its binding is dependent on a conformation of the amyloid fiber comprising a β-sheet structure.

Example 8

Fractionation by Density-Gradient Ultracentrifugation

The properties of monoclonal antibodies in inhibiting $A\beta_{1-42}$ fiber polymerization and disaggregating of $A\beta_{1-42}$-fibers were studied by density-gradient ultracentrifugation (Rzepecki et al., 2004) which is based on the principle to distribute between differently sized resulting peptide fibers after incubation with and without antibodies followed by a SDS-PAGE sedimentation analysis on a preformed gradient (OptiPrep™). Simultaneous analysis of populations of preformed Aβ-fibers, disaggregation and inhibition of aggregation properties of the co-incubated antibodies, and the binding of the antibodies to the fibers are obvious advantages of these methods.

TABLE 2

|  | Monomers | | | Fibers | | |
| --- | --- | --- | --- | --- | --- | --- |
|  | $k_a$(1/Ms) | $k_d$(1/s) | KD (M) | $k_a$(1/Ms) | $k_d$(1/s) | KD (M) |
| mACI-01-Ab7 C2 exp. 1 | 1.8E+04 | 2.7E−03 | 1.5E−07 | 2.4E+04 | 9.9E−04 | 4.1E−08 |
| mACI-01-Ab7 C2 exp. 2 | 1.5E+04 | 5.3E−03 | 3.5E−07 | 5.60E+04 | 9.66E−04 | 1.73E−08 |
| mACI-01-Ab7 C2 exp. 3 |  |  |  | 3.26E+04 | 1.49E−03 | 4.58E−08 |
| average mACI-01-Ab7 C2 | 1.6E+04 ±0.21 | 4.0E−03 1.84 | 2.5E−07 1.41 | 3.8E+04 1.66 | 1.1E−03 0.3 | 3.5E−08 1.53 |

Example 7

Binding of mACI-01-Ab7 C2 Monoclonal Antibody to Amyloid Fibers

Figure 3B:
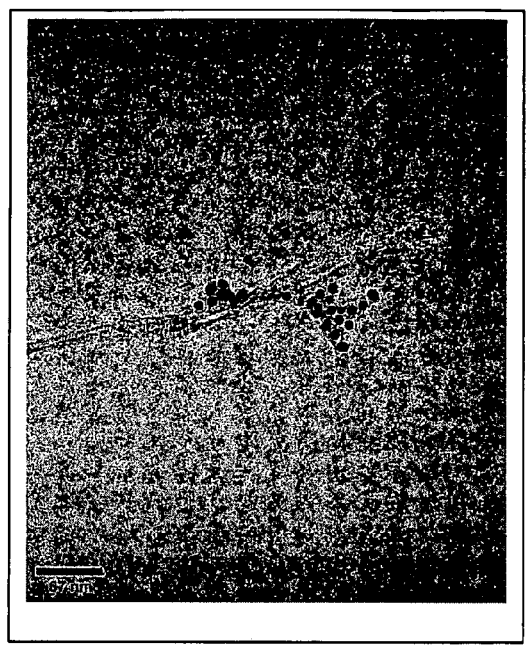

To analyze the molecular binding side of the antibody on pre-formed fibers negatively contrasted transmission electronic microscopy (TEM) was performed (FIGS. 3a and 3b).

The antibody, mACI-01-Ab7 C2, was coupled with 8 nm colloidal gold according to [4,5]. For the co-incubation of amyloid 1-42 (Aβ1-42) fibers 6.65 uM fibers were incubated for 24 h at RT with the gold-labeled antibody with the molar ratio The monoclonal antibodies raised against $A\beta_{1-16}$ (mACI-01-Ab7 C2), $A\beta_{1-16(\Delta 14)}$ (mACI-02-Ab6), $A\beta_{1-15}$ (mACI-24-Ab4), $A\beta_{22-35}$ (mACI-11-Ab9), and $A\beta_{29-40}$ (mACI-12-Ab11) were all analyzed in disaggregating assays whereas the inhibiting of aggregation properties were studied only for the monoclonal antibody mACI-02-Ab6, mACI-24-Ab4, and mACI-01-Ab7 C2.

For the inhibition of $A\beta_{1-42}$ aggregation, $A\beta_{1-42}$ monomers were incubated with mAbs at two different molar ratios (molar ratio of monomer $A\beta_{1-42}$ thirty- or hundred-fold higher than mAb) with the Aβ final concentration of 50 µM. After 24 hrs incubation at 37° C., samples were overlayed over a discontinuous gradient of Optiprep™ and tubes were spun at 259 000 g for 3 hrs at 4° C. 15 fractions were harvested (140 µL each), fraction 1 was the least dense fraction from the top of the gradient and fraction 15 is the densest fraction from the bottom of the gradient. The pellet was also taken. The collected fractions were analyzed by SDS-PAGE with silver staining. The concentration $A\beta_{1-42}$ for inhibition assays was five times less than for disaggregation assays which decrease amyloid aggregation kinetic and ensure measurement within the linear phase.

For the disaggregation of preformed $A\beta_{1-42}$ fibrils by co-incubation with mAbs (at two different molar ratios 1:30 and 1:100, mAb+Monomer $A\beta_{1-42}$ with the Aβ final concentration of 246 µM), the samples were incubated for 24 hours at 37° C. After 24 hrs samples were fractioned by ultracentrifugation and separated by SDS-PAGE as described above and before (Rzepecki et al., 2004).

Inhibition of $A\beta_{1-42}$ Aggregation Assay:

It could be demonstrated that without addition of mAb, Aβ peptide was aggregated after 24 hrs incubation time and most of the protein was found in fractions 13-15, demonstrating complete polymerization of the Aβ peptide monomers. Successful and significant inhibition of aggregation should result in smaller fibers or polymeric soluble amyloid β (Aβ) protein, which should be found in fractions with lower density (10-13). Exactly this shift in bands could be demonstrated in aggregation assay containing mACI-01-Ab7 C2, which showed a distribution of Aβ peptide over fractions 11, 12 and 13.

This was confirmed in a $2^{nd}$ experiment where mACI-01-Ab7 C2 caused again a shift in bands for the majority (strongest band) from 14 to 13 and a significant solubilization of the bands running in fraction 14 to pellet. This means, that mACI-01-Ab7 C2 exhibits a strong capacity to inhibit polymerization of Aβ peptide monomers into fibers and revealed a specific binding to the A□fibers (in fraction 13)

Similar observations were made when using antibody mACI-24-Ab4 and mACI-02-Ab6. Without addition of mAb, Aβ peptide was aggregated after 24 hrs incubation time and most of the protein was found in fractions 13 to pellet, (pellet, very little in 12), demonstrating complete polymerization of the Aβ peptide monomers. Successful and significant inhibition of aggregation should be resulted in smaller fibers or polymeric soluble amyloid β (Aβ) protein, which should be found in fractions with lower density. In the inhibition of aggregation assay, mACI-24-Ab4 caused a shift in bands for the majority (strongest band) from 13 to 11 and 12 and a significant solubilization of the bands running in fraction 13 to pellet whereas mACI-02-Ab6 caused a shift in bands from 13 to 10 but additionally a complete inhibition of larger fiber formation (fractionized in 13 to pellet). These data indicate that both mACI-24-Ab4 and mACI-02-Ab6 exhibit a strong capacity to inhibit polymerization of Aβ peptide monomers into fibers and revealed a specific binding to the A□fibers (in fraction 11 and 12).

In contrast, aggregation assay containing mACI-11-Ab9, at molar ratio 1:30, showed larger aggregates spread between fractions 12-15 and pellet. In presence of mACI-12-Ab11, at molar ratio 1:30, aggregates are found in fractions 11-15 and pellet, but with strongest signal in fractions 11 and 12. This means, that mACI-01-Ab7 C2 and mACI-24-Ab4 exhibit the strongest capacity to inhibit polymerization of Aβ peptide monomers into fibers. mACI-12-Ab11 has significant less inhibition properties than mACI-01-Ab7 C2, to obtain this weak inhibitory activity a three times higher molar ratio was needed. Still, minor inhibition can be observed when compared to mACI-11-Ab9 which was not able to inhibit Aβ peptide fiber aggregation. All mAb revealed a specific binding to the A□-fibers (for mACI-01-Ab7 C2 in fraction 11+12; for mACI-11-Ab9 in fraction 12 and weak in 13; for mACI-12-Ab11 in fraction 11 and 12).

In all of the inhibition assays, peptide was detected in the bottom fractions. The non-bounded mAb (37 kDa, 95 kDa and bigger than 120 kDa) appeared in the upper half of the gradient (fractions 3-9 and 4-8, respectively).

Disaggregation of $A\beta_{1-42}$ Fibers Assay:

Due to the incomplete fiber polymerization the distribution of $A\beta_{1-42}$ fibrils alone demonstrates a broader range of fractions (11-15). Therefore demonstration of successful and significant disaggregation properties of the antibodies when co-incubated with the pre-formed fibers is more difficult than in the aggregation analysis. Only shift in the majority of the fibers towards fractions of lower density but still within the amyloid alone fraction range would indicate disaggregation activity; for amyloid alone the major band is fraction 12. Addition of mACI-01-Ab7 C2 at molar ratio 1:100 showed no shift of amyloid fibers towards fractions of lower density (still between fractions 11-15), but with a shift of the stronger signal within the fraction range from 12 to 11, when compared to amyloid alone. Despite non-optimal circumstances of incomplete fiber formation, mACI-01-Ab7 C2 indicates low but detectable disaggregation activities.

In contrast, the co-incubation of preformed $A\beta_{1-42}$ fibrils with mACI-02-Ab6 demonstrated no shift of bands to lower density fraction when incubated with the same amyloid peptide:antibody molar ratio like mACI-01-Ab7 C2. Only when a three times higher molar ration of 1:30 was used amyloid fibers shifted from 12-15 (amyloid alone without antibody co-incubation) to fractions 11-15. Therefore it seemed that mACI-01-Ab7 C2 has slightly higher disaggregation properties than mACI-02-Ab6.

The detection of bands corresponding to mAb in the lower half of gradient fraction demonstrates binding of mACI-02-Ab6 and mACI-01-Ab7 C2 to $A\beta_{1-42}$ fibrils (fraction 11 to 15 for both mAb).

The disaggregation property of mACI-01-Ab7 C2 could be confirmed in a further experiment, where complete fiber polymerization could be demonstrated by the distribution of $A\beta_{1-42}$ fibrils in the absence of an antibody in fractions 13 to P (pellet). Here shifts of fibers towards fractions of lower density indicate disaggregation activity of the antibody, when co-incubated to pre-formed fibers. Addition of mACI-01-Ab7 C2 at molar ratio 1:100 showed a shift of the majority of amyloid fibers from 13 to 12 and additionally a shift of the band with the lowest density from 13 towards 11. Therefore mACI-01-Ab7 C2 indicates also a strong disaggregation activity.

The detection of bands corresponding to mAb in the lower half of gradient fraction demonstrates binding of mACI-01-Ab7 C2 to $A\beta_{1-42}$ fibrils (fraction 11 to P) whereas bands corresponding to mAb in fractions 4 to 7 indicating unbound antibody.

To summarize these results it could be successfully demonstrated that the monoclonal antibody mACI-01-Ab7 C2 targeting amyloid Aβ-peptide binds to pre-formed fibers and is capable to inhibit in vitro aggregation from monomeric Aβ-peptides to fibers and disaggregate pre-formed fibers.

Similar observations were made when using mACI-24-Ab4. Similar to aggregation assay, complete fiber polymerization could be demonstrated by the distribution of $A\beta_{1-42}$ fibrils alone in fractions 12 to P (pellet). Here shifts of fibers towards fractions of lower density would indicate disaggregation activity of the antibody, when co-incubated to pre-formed fibers. Addition of mACI-24-Ab4 at molar ratio 1:100 showed a shift of the majority of amyloid fibers from 12 to 11. Therefore, mACI-24-Ab4 indicates also a strong disaggregation activity.

Example 9

Fluorescent Assay to Assess Inhibition of $A\beta_{1-42}$ Filament Aggregation and Disaggregation of Pre-formed $A\beta_{1-42}$ Filaments by Co-Incubation with mAb BIS-ANS Fluorescent Assay:

To assess the inhibition properties of the mAb the BIS-ANS (LeVine, 2002) fluorescent assay was used which specifically detects the monomer or non-fibrillous population of $A\beta_{1-42}$ filaments. Before fluorescent measurement, $A\beta_{1-42}$ monomers were pre-incubated with either buffer, served as control, or mAb (molar ratio 1:100, mAb vs. $A\beta_{1-42}$ peptide) for 14 hours at 37° C. Relative fluorescence units were automatically recorded and results were expressed as changes to the control in percentage.

mACI-02-Ab6 showed a slight inhibition capability when compared to the control (125.8±28.5% vs 100±29.5%). mACI-01-Ab7 C2 seemed to have weak activity (108.0±30.0%) and no improvement compared to the control could be observed with the mAb mACI-11-Ab9 and mACI-12-Ab11 (93.5±21.9% and 73.2±47.7%). This result confirms the ultracentrifugation data, in which mACI-01-Ab7 C2 exhibits larger inhibition capacity than mACI-11-Ab9 and mACI-12-Ab11.

Example 10

Thioflavin T (Th-T) Fluorescent Assay

To measure both inhibition of aggregation as well as disaggregation properties of the mAb the Thioflavin T (Th-T) fluorescent assay was used which specifically binds to fibrillar $A\beta_{1-42}$ molecules and subsequently the fluorescent emission intensity correlates with the amount of $A\beta_{1-42}$ filaments present in the solution.

Before fluorescent measurement, $A\beta_{1-42}$ monomers were pre-incubated with either buffer (control), or mAb (molar ratio 1:100, mAb vs. $A\beta_{1-42}$ peptide) for 48 hours at 37° C. Relative fluorescent units were automatically recorded and results were expressed as changes to the control in percentage.

mACI-01-Ab7 C2 showed a significant inhibition capability when compared to the control (11.03±20.7% vs 100±40.5%). This result confirms the ultracentrifugation data, in which mACI-01-Ab7 C2 exhibits inhibition capacity.

To measure the disaggregation properties of the mAb the Thioflavin T (ThT) fluorescent assay was used which specifically binds to fibrillar $A\beta_{1-42}$ molecules and subsequently the fluorescent emission intensity correlates with the amount of $A\beta_{1-42}$ filaments present in the solution. Before measurement, $A\beta$ fiber were preformed for 7 days (at 37° C. in PBS, pH 7.1) and then subsequently co-incubated with mAb or buffer (negative control), for 24 hours at 37° C. at molar ratio of 1:100 (mAb vs. $A\beta_{1-42}$)-Relative fluorescent units were automatically recorded by an ELISA microtiter plate reader, and results were expressed as changes to the control in percentage.

In accordance with the ultracentrifugation data mACI-01-Ab7 C2 showed also in the Th-T disaggregation test in two independent experiments the best properties with 35±11% and 64.57±13.58% (vs 100.0±15.37%), respectively, disaggregation power over the control.

mACI-24-Ab4 also showed significant disaggregation properties (62.99±10.34% vs 100.0±10.03%; p<0.0001) in the Th-T assay.

mACI-11-Ab9 was somewhat less active with 28±14%, whereas ACI-02-Ab6 and ACI-12-Ab11 did not exhibit significant disaggregation properties (17±12% and 13±11% respectively).

When summarizing ultracentrifugation and fluorescent assays mACI-01-Ab7 C2, mACI-01-Ab6 and mACI-24-Ab4 showed bi-functionality capacities to inhibit fiber aggregation and to shorten pre-formed $A\beta_{1-42}$-filaments in centrifugation experiment which could be confirmed by fluorescent assay. Additionally, centrifugation experiment demonstrated specific binding of the mAb to amyloid fibers.

mACI-11-Ab9 showed significant lower inhibition capability in ultracentrifugation, when compared to mACI-01-Ab7 C2 even it was three times higher concentrated, which could be confirmed by BIS-ANS assay. For the disaggregation analysis mACI-01-Ab7 C2 demonstrated in both centrifugation analysis and ThT assay properties to shorten pre-formed $A\beta_{1-42}$ filaments. mACI-02-Ab6, three times higher concentrated in centrifugation experiment, was also positive in both assay but much stronger in centrifugation experiment.

From the above results it is evident that that mACI-01-Ab7 C2 and mACI-02-Ab6 are the only antibodies showing activity in terms of bi-functionality in interacting with $A\beta_{1-42}$ filaments, inhibition of aggregation and disaggregation of preformed fibers.

Example 11

NMR and Fluorescence Characterization of the Interaction of mACI-01-Ab7 C2

Monoclonal Antibody with $^{13}$C-labeled β-Amyloid 1-42 Peptide

To evaluate the potential mechanism by which the mAb solubilize pre-formed fibers or inhibit fiber formation, a head-to-head-experiment between Th-T fluorescent assay and solid-state NMR of U-$^{13}$C Tyr10 and Val12-labeled β-amyloid 1-42 peptide was performed (FIG. 4). Therefore the aim of this investigation was to follow the β-sheet transition by solid state NMR spectroscopy in the β-amyloid peptide and in the presence of the monoclonal antibody and to directly compare this with disaggregation capacity measured by Th-T fluorescent assay.

Solid-state NMR spectroscopy not only detects a transition in the secondary structure, but it also allows to localize the domains of the $A\beta_{1-42}$-peptide which dominate the structural transition. Solid-state NMR has proven its applicability to the problem as it has contributed to the structure determination of the $A\beta_{1-42}$-fibres (Petkova et al., 2004, Petkova et al., 2002). In particular the correlation of the $^{13}C_\alpha$ and $^{13}C_\beta$ chemical shift with the secondary structure (Cornilescu et al., 1999, Luca et al., 2001, Iwadate et al, 1999) is a valuable tool to test changes of the secondary structure within a peptide.

The synthesis of the peptide labeled including a $^{13}$C pre-labeled valine at position 12 ($^{12}$Val) and a $^{13}$C pre-labeled tyrosine at position 10 ($^{10}$Tyr) was performed by an Fmoc synthesis protocol. Identity and purity of the peptide were confirmed my MALDI mass spectroscopy. The labeled β-amyloid peptide (1-42) was used to generate fibers by incubating the peptide solution in PBS buffer for 1 week at 37° C. The major problem, the poor solubility of the amyloid β-peptide in PBS buffer, could be solved in the following manner: The pH value of the PBS buffer was temporarily increased by tiny amounts of ammonia to dissolve the amyloid β-peptide. The original pH value of the PBS buffer was reobtained by incubating the sample in the presence of a bigger PBS bath using the volatile character of ammonia.

To measure the effect of the β-sheet breaking antibodies, solution of fibers were incubated with the antibody for 24 hours at 37° C. for both NMR and Th-T assay. For real-time comparison an aliquot of the same solution was used for Th-T fluorescent assay and the remaining solution was lyophilized for the NMR measurements.

After analyzing first the disaggregation capacities of mACI-01-Ab7 C2 by co-incubation with pre-formed 13C-labeled amyloid β-fibers using Th-T fluorescent assay, it could be shown that the mAb disaggregated the fibers by 38%. Then NMR spectra analysis was performed.

To investigate the differences between PBS (control) and mAb incubation each spectrum was deconvoluted using PeakFit (http://www.systat.com/products/PeakFit). The lines were well matched by employing a mixed Lorentzian/Gaussian fitting procedure, the results of which are shown in FIG. 4. The results are summarized in Table 3 but the most obvious difference is the integral intensities of the two populations that are needed to fit the double peak around 30-33 ppm. The peak at c33 ppm corresponds to the beta sheet conformation of the fibers whilst that at 30 ppm is a result of random coil conformation. The sample incubated in PBS showed most of the label in a beta sheet conformation (81.7%) (FIG. 2 top) which is reduced when the sample is incubated with mACI-01-Ab7 C2 (53.5%) (FIG. 4 bottom). The reduction in the population of the beta sheet conformation with respect to the random coil conformation as determined by study of the Val 12 Cβ is of the order of 35% and is therefore in close agreement with that measured using fluorescence.

TABLE 3

Comparison of the fitted parameters for the two conformations of Val 12 Cβ.

| | PBS | | | mACI-01-Ab7-C2 | | |
|---|---|---|---|---|---|---|
| Resonance | δ ISO (ppm) | FWHH (Hz) | % Integral Intensity | δ ISO (ppm) | FWHH (Hz) | % Integral Intensity |
| Val Cβ - sheet | 32.60 | 479 | 81.7 | 33.09 | 366 | 53.5 |
| Val Cβ - random | 30.27 | 200 | 18.3 | 30.27 | 340 | 46.5 |

The fitted chemical shifts for the two conformations are quite similar but the integral intensities are very different, reflecting a reduction in the original beta sheet conformation by approx 35% (1-(53.5/81.7)). This is in very close agreement with the value obtained from the fluorescence measurement.

To summarize these results it could be successfully demonstrated that the monoclonal antibody mACI-01-Ab7 C2 targeting the N-terminal 1-16 region of amyloid Aβ-peptide binds to pre-formed fibers and is capable to inhibit in vitro aggregation from monomeric Aβ-peptides to fibers and disaggregate pre-formed fibers, as demonstrated by density gradient ultracentrifugation experiment as well by Th-T fluorescent assay. In addition by binding of this antibody to pre-formed fibers, a transition from beta sheet majority to random coil secondary conformation environment of Val12 could be induced. This might be the potential mechanism by which fibers could be solubilized by binding of the monoclonal mACI-01-Ab7 C2 antibody also because of the detailed analysis of Val 12 Cβ peak reveals reduction of beta sheet component by 35% which is in close agreement with fluorescence data (38%).

Example 12

Functionality of mACI-01-Ab7 C2 on Amyloid Fibers 12.1 Modification of Conformation of Aβ1-42 Fibers and Initiation of Disaggregation after Binding of the mACI-01-Ab7 C2 Antibody In order to evaluate the mechanism by which the antibody is capable to disaggregate preformed beta-amyloid ($A\beta_{1-42}$) fibers a head-to-head comparison of Thioflavin-T (Th-T) fluorescent assay was performed measuring disaggregation and solid-state Nuclear Magnetic Resonance (NMR) of U-13C Tyrosine10 and Valine12-labeled Aβ1-42 peptide analysing secondary conformation. The antibody solubilized 35.4% of the preformed Aβ1-42 fibers and simultaneously induced a shift in secondary conformation from beta sheet to random coiled. The reduction in the population of the beta sheet conformation with respect to the random coil is of the order of 35% and is therefore in close agreement with that measured using fluorescence Th-T assay. These data indicate that the binding of the antibody initiates a transition of the secondary structure which potentially causes a destabilization of the parallel intermolecular arrangement of the beta sheets affecting a break of elongated fibers into smaller fragments.

12.2 Conformation-Dependent Binding Affinity of mACI-01-Ab7 C2 Antibody:

Since it is well known in the scientific literature that a proportion of the antibody-antigen binding energy can be used to a energy-dependent modification of the conformation of an antigen 6, a comparison experiment of the binding affinity of the mACI-01-Ab7 C2 antibody to the whole $A\beta_{1-42}$ protein and to a smaller, nine amino acid long, peptide comprising the antibody's epitope was performed. For this comparison the affinities of the antibody mACI-01-Ab7 C2 were analyzed by ELISA using biotinylated peptides covering the complete amino-acid sequence of the mACI-01-Ab7 C2's epitope (aminoacids 13-21 of the $A\beta_{1-42}$ sequence, produced by Mimotopes and purchased from ANAWA Trading SA) and a biotinylated complete Aβ1-42 peptide (Bachem). The analysis was done according to the manufacturer's (Mimotopes) instructions. The antibody binds with a 38.40% higher affinity to the peptide comprising its specific epitope (aminoacids 13-21 of the $A\beta_{1-42}$ sequence) than to the whole Aβ1-42 protein. It is therefore suggested that the difference in binding affinity energy was used for the energy-consuming transition of the secondary conformation of the amyloid protein to present the antigen in a more acceptable position for the antibody interaction. This may explain why the affinity of the antibody is lower for the native (the whole amyloid protein) than for the isolated subunit.

Example 13

Conformation-Specific Binding of mACI-01-Ab7 C2 to Different Classes of Amyloid Protein In order to evaluate the specificity of mACI-01-Ab7 C2 to different stages of polymerized amyloid protein, monomeric and polymeric soluble amyloid, particularly, amyloid β (Aβ) protein, and fibrillic amyloid, an ELISA coated with these different stages of polymeric beta-amyloid was performed. Monomers were prepared according to a modified method published by [7], polymeric soluble amyloid, particularly, amyloid β (Aβ) according to [8], whereas fibers were performed by incubation of amyloid (Bachem, Switzerland) with a final concentration of 1 μg/μl in Tris/HCl pH 7.4 at 37° C. for 5 days followed by a centrifugation step (10,000 rpm for 5 minutes). Then amyloid polymers were coated on an ELISA plates with a final concentration of 55 μg/ml and binding affinity ELISA by using an anti-mouse IgG monoclonal antibody (Jackson ImmunoResearch Laboratories, Inc.) labelled with alkaline phosphate was performed. The antibody binds with higher affinity to polymeric soluble amyloid B (AB) protein (IC50=2.53 nM) than to fibers (IC50=5.27 nM) and with the lowest to monomers (IC50=8.3 nM). These data indicate that the antibody's binding is influenced beside its epitope by the conformation of the different amyloid aggregates.

Example 14

Epitope Mapping of Monoclonal Antibody mACI-01-Ab7 C2

Epitope mapping of the monoclonal antibody mACI-01-Ab7 C2 was performed by ELISA using three different peptide libraries. One library comprises a total of 33 biotinylated peptides covering the complete amino acid (aa) sequence of Aβ1-42 (produced by Mimotopes and purchased from ANAWA Trading SA), the second library contains biotinylated peptides using peptide 12 (aa12-20 of Aβ) from the first peptide library and substituting each amino acid in the sequence by an alanine (see table 41 below), and the third library contains biotinylated peptides 13, 14, or 15 (aa 13-21, 14-22 or 15-23 of Aβ) and substituting in each case the last amino acids to an alanine or to a glycine for aa 21 which is already an alanine (see table 5 below). A biotinylated complete Aβ1-42 peptide was used as positive control (Bachem). Epitope mapping was done according to the manufacturer's (Mimotopes) instructions. Briefly, Streptavidin coated plates (NUNC) were blocked with 0.1% BSA in PBS overnight at 4° C. After washing with PBS-0.05% Tween 20, plates were coated for 1 hour at RT with the different peptides from the library, diluted in 0.1% BSA, 0.1% Sodium Azide in PBS to a final concentration of 10 μM. After washing, plates were incubated for 1 hour at RT with the mACI-01-Ab7 C2 antibody or an isotype control mouse IgG2b antibody, diluted to 10 μg/ml in 2% BSA, 0.1% Sodium Azide in PBS. Plates were washed again and incubated with alkaline phosphatase conjugated goat anti mouse IgG for 1 h at RT. After final washing, plates were incubated with phosphatase substrate (pNPP) and read at 405 nm using an ELISA plate reader.

It was shown that the monoclonal antibody mACI-01-Ab7 C2 bound specifically to peptides 12, 13, 14 and 15 of the first peptide library. These 4 peptides comprise an 12-20 (VHHQKLVFF) (SEQ ID NO: 29), 13-21 (HHQKLVFFA) (SEQ ID NO: 39), 14-22 (HQKLVFFAE) (SEQ ID NO: 41) and 15-23 (QKLVFFAED) (SEQ ID NO: 43) of Aβ1-42 suggesting that the epitope lies in region 12-23 of Aβ. A second library with alanine substitutions was used to determine the critical an for binding to peptide 12-20 (VHHQKLVFF) (SEQ ID NO: 29). The binding of the mACI-01-Ab7 C2 antibody is lost completely when aa 16, 17, 19 or 20 are substituted by an alanine, indicating that these an are absolutely critical for binding of the antibody to Aβ. The binding of the mACI-01-Ab7 C2 antibody is partially lost when aa 15 and 18 are substituted.

The binding was also almost completely lost when aa 14 was substituted for an alanine, indicating that aa 14 is also very important for binding.

Finally, a third library was used to determine whether aa 21, 22 or 23 are critical for binding to the epitope. The binding of the antibody to aa 15-23 was reduced when aa 23 was substituted for an alanine, indicating that aa 23 is also important for binding. The binding was partially lost when aa 21 was substituted for a glycine and slightly lost when aa 22 was substituted for an alanine.

Table 4. Summary of Peptides Used in the Second Library.

aa that are important for binding are marked in italics and underscored and aa absolutely critical for binding are marked in italics and bold and underscored:

TABLE 4

Summary of peptides used in the second library.
aa that are important for binding are marked in italics and underscored
and aa absolutely critical for binding are marked in italics and bold
and underscored

| | | | | | | | | |
|---|---|---|---|---|---|---|---|---|
| p12–20 SEQ ID NO: 29 | V | H | H | Q | K | L | V | F | F |
| A12 SEQ ID NO: 30 | A | H | H | Q | K | L | V | F | F |
| A13 SEQ ID NO: 31 | V | A | H | Q | K | L | V | F | F |
| A14 SEQ ID NO: 32 | V | H | A | Q | K | L | V | F | F |
| A15 SEQ ID NO: 33 | V | H | H | A | K | L | V | F | F |
| A16 SEQ ID NO: 34 | V | H | H | Q | A | L | V | F | F |
| A17 SEQ ID NO: 35 | V | H | H | Q | K | A | V | F | F |
| A18 SEQ ID NO: 36 | V | H | H | Q | K | L | A | F | F |
| A19 SEQ ID NO: 37 | V | H | H | Q | K | L | V | A | F |
| A20 SEQ ID NO: 38 | V | H | H | Q | K | L | V | F | A |
| aa no. | 12 | 13 | *14* | *15* | 16 | 17 | *18* | 19 | 20 |

Table 5. Summary of Peptides Used in the Third Library.

aa that are important for binding are marked in italics and underscored and aa absolutely critical for binding are marked in italics and bold and underscored

TABLE 5

Summary of peptides used in the third library.
aa that are important for binding are marked in italics and underscored
and aa absolutely critical for binding are marked in italics and bold and
underscored

| | | 13 | 14 | 15 | 16 | 17 | 18 | 19 | 20 | 21 | 22 | 23 |
|---|---|---|---|---|---|---|---|---|---|---|---|---|
| p13–21 SEQ ID NO: 39 | | H | H | Q | K | L | V | F | F | A | | |
| p13–21 SEQ ID NO: 40 | G21 | H | H | Q | K | L | V | F | F | G | | |
| p14–22 SEQ ID NO: 41 | | | H | Q | K | L | V | F | F | A | E | |
| p14–22 SEQ ID NO: 42 | A22 | | H | Q | K | L | V | F | F | A | A | |
| p15–23 SEQ ID NO: 43 | | | | Q | K | L | V | F | F | A | E | D |
| p15–23 SEQ ID NO: 44 | A23 | | | Q | K | L | V | F | F | A | E | A |
| aa no. | | 13 | *14* | *15* | 16 | 17 | *18* | 19 | 20 | 21 | 22 | *23* |

Example 15

Influence of Passive Vaccination with mACI-01-Ab7 C2 on Brain Amyloid Load in Single Transgenic hAPP Mice To assess the in vivo capacity of the mACI-01-Ab7 C2 monoclonal antibody to bind and clear soluble amyloid out of the brain, 6 month old single hAPP mice 9, gender and age matched, were used for a passive immunization study with different dose. Soluble Amyloid load was analyzed at the end of the study by harvesting the brain of the animals and by performing an Aβ 1-40 and Aβ 1-42 specific ELISA (TGC, Germany).

8-13 animals per group received two injections at an interval of one week of 100, 300 and 1000 μg monoclonal antibody in 200 μl PBS whereas injection of PBS alone served as control. One day after the second injection animals were sacrificed for biochemical analysis of soluble amyloid fraction. To quantify the amount of human Aβ 1-40 and human Aβ 1-42 in the soluble fraction of the brain homogenates and/or in cerebrospinal fluid (CSF), commercially available Enzyme-Linked-Immunosorbent-Assay (ELISA) kits were used (h Amyloid β 40 or β 42 ELISA high sensitive, TGC, Switzerland). The ELISA was performed according to the manufacturer's protocol. Briefly, standards (a dilution of synthetic Aβ 1-40 or Aβ 1-42) and samples were prepared in a 96-well polypropylene plate without protein binding capacity (Greiner, Germany). The standard dilutions with final concentrations of 1000, 500, 250, 125, 62.5, 31.3 and 15.6 pg/ml and the samples were prepared in the sample diluent, furnished with the ELISA kit, to a final volume of 60 μl. Since amyloid levels increase with the age of the mouse and since the actual evaluation requires that the readings of the samples are within the linear part of the standard curve, the samples for Aβ 40 analysis were diluted 2:3, the samples for Aβ 42 analysis were not diluted.

Samples, standards and blanks (50 μl) were added to the anti-Aβ-coated polystyrol plate (capture antibody selectively recognizes the C-terminal end of the antigen) in addition with a selective anti-Aβ-antibody conjugate (biotinylated detection antibody) and incubated overnight at 4° C. in order to allow formation of the antibody-Amyloid-antibody-complex. The following day, a Streptavidine-Peroxidase-Conjugate was added, followed 30 minutes later by the addition of a TMB/peroxide mixture, resulting in the conversion of the substrate into a colored product and the color intensity was measured by means of photometry with an ELISA-reader with a 450 nm filter. Quantification of the Aβ content of the samples was obtained by comparing absorbance to the standard curve made with synthetic Aβ 1-40 or Aβ 1-42. Data were expressed as individual changes to mean control value (in percent to control).

The total amount of Aβ 40 in brain homogenates could be significantly reduced and roughly non-significantly for Aβ 42 when single hAPP mice were passively immunized by two i.p. injections of monoclonal antibody ACI-01-Ab7 C2 at a dose of 300 μg (Aβ 40: −27.3±13.9% with p<0.05; Aβ 42: −8.6±22.4 with p=0.56; unpaired Student's T test), whereas 100 and 1,000 μg didn't reach significance. Immunization with 100 μg lead to an increase for Aβ 40 and Aβ 42 in brain homogenates (Aβ 40: 32.3±36.8%; A☐42: 38.3±51.4%) whereas treatment with 1,000 μg elicited the right tendency of amyloid burden lowering and could be potentially effective with an increased number of animals per group (AD 40: −2.2±26.0%; Aβ 42: −9.3±15.9%). These data demonstrate that in an acute immunization protocol the antibody mACI-01-Ab7 C2 is capable to decrease the total amount of soluble Aβ in the brain of this murine AD model. Interestingly, it seems to be that the dose-relationship is transient but more studies with larger groups must be performed in order to gain significant data.

Example 16

Influence of Chronic Passive Administration of mACI-01-Ab7 C2 on Plaque Load in Double Transgenic hAPPxPS1 Mice To assess the in vivo capacity of the mACI-01-Ab7 C2 monoclonal antibody to bind and reduce amyloid plaques in the brain, 3.5 month old double transgenic hAPPxPS1 mice [10], gender and age matched, were used for a 4 month long chronic passive immunization study. Amyloid plaques were analyzed at the end of the study by histochemistry of the brain of the animals by binding of Thioflavin S.

15 transgenic animals received 16 weekly injections of 500 μg monoclonal antibody in PBS. 15 animals were injected with PBS alone, serving as controls. All injections were given intra-peritoneally. At sacrifice, mice were anaesthetized and flushed trans-cardially with physiological serum at 4° C. to remove blood from the brain vessels. Subsequently, the brain was removed from the cranium and hindbrain and forebrain were separated with a cut in the coronal/frontal plane. The forebrain was divided evenly into left and right hemisphere by using a midline sagittal cut. One hemisphere was post-fixed overnight in 4% paraformaldehyde for histology. Sagittal vibratome sections (40 μm) were cut for free floating incubations and stored at 4° C. until staining in PBS with 0.1% sodium azide. Five sections at different levels were stained for dense plaques with Thioflavin S. Sections of all animals used were randomized for staining and blind quantification. Images were acquired with a Leica DMR microscope equipped with a Sony DXC-9100P camera and analyzed with a computer using Leica Q-Win software. Light intensity and condenser settings for the microscope were kept constant throughout the image acquisition process. All acquired images were subjected to the same computer subroutines to minimize investigator bias. Density slice thresholding was applied uniformly throughout analysis. The area of the subiculum was selected for automatic quantification of the amyloid load in the Thioflavin S staining.

The total plaque load and the number of plaques in the area of subiculum could be significantly reduced when double hAPP/PS1 mice were passively immunized for 4 months as described above. In plaque load a significant decrease of 31% (mACI-01-Ab7 C2: 1.11±0.21% and control: 1.61±0.35%; p=0.003, Mann-Whitney U-Test) could be achieved whereas the chronic passive immunization significantly reduced the amount of plaques by 19% (mACI-01-Ab7 C2: 8.73±1.36 and control: 10.78±1.36; p=0.006, Mann-Whitney U-Test), indicating that plaque solubilization occurred to a slightly lesser degree than plaque disruption.

Example 17

Influence of Passive Vaccination with mACI-01-Ab7 C2 on Memory Capacity in Single Transgenic hAPP Mice To analyze the in vivo capacity of the mACI-01-Ab7 C2 antibody to modify or increase cognitive functionality, 9 month old single hAPP mice, gender and age matched, were used for passive immunization study. Non-spatial cognition was measured at the end of the immunization period assessed by new Object Recognition Task (ORT).

12 animals per group received two intra peritoneal injections of 400 µg monoclonal antibody in 200 µl PBS whereas injection of PBS alone served as control. One day after the second injection cognitive capability were studied in a new Object Recognition Task (ORT)[12,13]. For ORT enrollment mice were placed for 10 minutes into a behavioral arena and faced to a new unknown object. Exploration time was recorded. Three hours later the same animals were re-placed into the same arena for a $2^{nd}$ session but faced with the old, previously explored, and additionally with a new object. Again, exploration times for both objects were recorded and resulting cognition index was calculated as the ratio of exploration time for the new object related to total exploration time and expressed as proportional changes to the control.

Passive vaccination with mACI-01-Ab7 C2 leads to a significant increase of cognitive memory capacities in single transgenic AD mice (mACI-01-Ab7 C2: 131.6±9.1% and control: 100.0±9.2% with p<0.05; unpaired Student's T test and n=12 per each group).

Deposits:

The following hybridoma cell lines were deposited with the "Deutsche Sammlung von Mikroorganismen und Zellkulturen GmbH (DSMZ) in Braunschweig, Mascheroder Weg 1 B, 38124 Branuschweig, under the provisions of the Budapest Treaty:

| Hybridoma line designation | Antibody designation | Deposition date | Accession No |
|---|---|---|---|
| FP 12H3 | mACI-01-Ab7 | 01 Dec. 2005; | DSM ACC2752 |
| FP 12H3-C2 | mACI-01-Ab7C2 | 01 Dec. 2005 | DSM ACC2750 |
| FP 12H3-G2 | mACI-01-Ab7G2 | 01 Dec. 2005 | DSM ACC2751 |

-continued

| Hybridoma line designation | Antibody designation | Deposition date | Accession No |
|---|---|---|---|
| ET 7E3 | mACI-02-Ab6 | 08. Dec. 2005 | DSM ACC2755 |
| EJ 7H3 | mACI-24-Ab4 | 08. Dec. 2005 | DSM ACC2756 |

REFERENCES

Bard F, Cannon C, Barbour R, Burke R L, Games D, Grajeda H, Guido T, Hu K, Huang J, Johnson-Wood K, Khan K, Kholodenko D, Lee M, Lieberburg I, Motter R, Nguyen M, Soriano F, Vasquez N, Weiss K, Welch B, Seubert P, Schenk D, Yednock T. (2000). Nature Med. 6, 916-919.

Barghorn S, Nimmrich V, Striebinger A, Krantz C, Keller P, Janson B, Bahr M, Schmidt M, Bitner R S, Harlan J, Barlow E, Ebert U, Hillen H (2005) Globular amyloid beta-peptide oligomer—a homogenous and stable neuropathological protein in Alzheimer's disease. J Neurochem 95:834-847.

Baschong W, Wrigley N G (1990) Small colloidal gold conjugated to Fab fragments or to immunoglobulin G as high-resolution labels for electron microscopy: a technical overview. J Electron Microsc Tech 14:313-323.

Blond and Goldberg, 1987, PNAS Mar. 1, 1987 Vol. 84 |no. 5| 1147-1151

Cornilescu G, Delaglio F, Bax A. (1999) J. Biomol. NMR; 13: 289-302.

Burdick, D. et al. Assembly and aggregation properties of synthetic Alzheimer's A4/beta amyloid peptide analogs. *J. Biol. Chem.* 267, 546-554 (1992).

DeMattos, Bales, K R, Cummins, D J, Dodart, J C, Paul, S M, Holtzmann, D. M (2001). Proc Natl Acad Sci USA 98, 8850-8855.

Dewachter I, Van D J, Smeijers L, Gilis M, Kuiperi C, Laenen I, Caluwaerts N, Moechars D, Checler F, Vanderstichele H, Van L F (2000) Aging increased amyloid peptide and caused amyloid plaques in brain of old APP/V717I transgenic mice by a different mechanism than mutant presenilin1. J Neurosci 20:6452-6458.

Dewachter I, Reverse D, Caluwaerts N, Ris L, Kuiperi C, Van den H C, Spittaels K, Umans L, Serneels L, Thiry E, Moechars D, Mercken M, Godaux E, Van Leuven F (2002) Neuronal deficiency of presenilin 1 inhibits amyloid plaque formation and corrects hippocampal long-term potentiation but not a cognitive defect of amyloid precursor protein [V717I] transgenic mice. J Neurosci 22:3445-3453.

Glenner and Wong, Biochem Biophys Res Comm 129, 885-890 (1984)

Harlow and Lane (Antibodies: A Laboratory Manual (Cold Spring Harbor Laboratory, New York 1988))

Heneka M T, Sastre M, Dumitrescu-Ozimek L, Dewachter I, Walter J, Klockgether T, Van L F (2005) Focal glial activation coincides with increased BACE1 activation and precedes amyloid plaque deposition in APP[V717I] transgenic mice. J Neuroinflammation 2:22.

Hodgson et al., Bio/Technology, 9:421 (1991)

Iwadate M, Asakura T, Williamson M P. (1999) J. Biomol. NMR; 13: 199-211.

Kirschner, D. A., Abraham, C., & Selkoe, D. J. X-ray diffraction from intraneuronal paired helical filaments and extraneuronal amyloid fibers in Alzheimer disease indicates cross-beta conformation. *Proc. Natl. Acad.* Sci. U.S.A 83, 503-507 (1986).

Khaw, B. A. et al. J. Nucl. Med. 23:1011-1019 (1982)
Kennedy, J. H., et al., 1976 (Clin. Chim. Acta 70:1-31)
Klein W L (2002) Abeta toxicity in Alzheimer's disease: globular oligomers (ADDLs) as new vaccine and drug targets. Neurochem Int 41(5):345-352.
Kohler and Milstein (Nature 256: 495-497 (1975))
LeVine, H. III, (2002). Arch Biochem Biophys 404, 106-115.
Luca et al., 2001
McGeer et al., 1994
Moechars D, Dewachter I, Lorent K, Reverse D, Baekelandt V, Naidu A, Tesseur I, Spittaels K, Haute C V, Checler F, Godaux E, Cordell B, Van L F (1999) Early phenotypic changes in transgenic mice that overexpress different mutants of amyloid precursor protein in brain. J Biol Chem 274:6483-6492.
Nelson, R. & Eisenberg, D. Recent atomic models of amyloid fibril structure. *Curr. Opin. Struct. Biol.* (2006).
Nicolau, C., Greferath, R., Balaban, T. S., Lazarte, J. E., and Hopkins, R. J. (2002). Proc Natl Acad Sci USA 99, 2332-2337.
Queen et al., Proc. Natl. Acad Sci USA, 86:10029-10032 (1989)
Pearson W. R. (1990), Methods in Enzymology 183, 63-98
Petkova A T, Buntkowsky G, Dyda F, Leapman R D, Yau W M, Tycko R. J. Mol. Biol. 2004; 335: 247-260.
Petkova A T, Ishii Y, Balbach J J, Antzutkin O N, Leapman R D, Delaglio F, Tycko R. (2002) Proc. Nat. Acad. Sci. U.S.A.; 99: 16742-16747.
Rousseaux et al. Methods Enzymology, 121:663-69, Academic Press, 1986
Rzepecki, P., Nagel-Steger, L., Feuerstein, S., Linne, U., Molt, O., Zadmard, R., Aschermann, K., Wehner, M., Schrader, T. and Riesner, D. (2004). J Biol Chem 279, 47497-47505.
Sambrook et al. loc. cit.
Schenk D, Barbour R, Dunn W, Gordon G, Grajeda H, Guido T, Hu K, Huang J, Smith, S. O., and Bormann, B. J. (1995). Proc Natl Acad Sci USA 92, 488-491.
Schenk et al., 1999
Schurs, A. H. W. M., et al. 1977 (Clin. Chim Acta 81:1-40
Slot J W, Geuze H J (1985) A new method of preparing gold probes for multiple-labeling cytochemistry. Eur J Cell Biol 38:87-93.
Smith and Waterman, Advances in Applied Mathematics 2 (1981), 482-489
Van dA, I, Wera S, Van L F, Henderson S T (2005) A ketogenic diet reduces amyloid beta 40 and 42 in a mouse model of Alzheimer's disease. Nutr Metab (Lond) 2:28.
Wagner et al (2002) Journal of Liposome Research Vol 12(3), pp 259-270
Ye, J., Dave, U. P., Grishin, N. V., Goldstein, J. L., and Brown, M. S. (2000). Proc Natl Acad Sci USA 97, 5123-5128.
Zrein et al. (1998), Clinical and Diagnostic Laboratory Immunology, 5(1): 45-49.
Experimental Eye Research 78 (2004) 243-256
WO 2004/058258
WO96/1359
WO96/29605

The invention claimed is:

1. A monoclonal antibody which specifically binds to monomeric, oligomeric or polymeric forms of amyloid-β, wherein:
   (i) the CDR 1 of the light chain variable region of the monoclonal antibody has the amino acid sequence of SEQ ID NO: 23;
   (ii) the CDR2 of the light chain variable region of the monoclonal antibody has the amino acid sequence of SEQ ID NO: 24:
   (iii) the CDR3 of the light chain variable region of the monoclonal antibody has the amino acid sequence of SEQ ID NO: 25:
   (iv) the CDR1 of the heavy chain variable region of the monoclonal antibody has the amino acid sequence of SEQ ID NO: 26:

(v) the CDR2 of the heavy chain variable region of the monoclonal antibody has the amino acid sequence of SEQ ID NO: 27; and (vi) the CDR3 of the heavy chain variable region of the monoclonal antibody has the amino acid sequence of SEQ ID NO: 28.

2. A pharmaceutical composition comprising a therapeutically effective amount of the monoclonal antibody according to claim 1 and a pharmaceutically acceptable carrier.

3. The pharmaceutical composition of claim 2 further comprising a biologically active agent for the treatment of diseases and disorders which are caused by or are associated with the aggregation of β-amyloid proteins, amyloid β fibers, amyloid β monomers or amyloid β oligomers.

4. The pharmaceutical composition of claim 3, wherein the biologically active agent is selected from the group consisting of compounds against oxidative stress, anti-apoptotic compounds, metal chelators, inhibitors of DNA repair, 3-amino-1-propanesulfonic acid (3APS), 1,3-propanedisulfonate (1,3PDS), secretase activators, β- and γ-secretase inhibitors, tau proteins, neurotransmitter, β-sheet breakers, anti-inflammatory molecules, and cholinesterase inhibitors (ChEIs).

5. The pharmaceutical composition of claim 3, wherein the biologically active agent is selected from the group consisting of tacrine, rivastigmine, donepezil, galantamine, niacin and memantine.

6. The pharmaceutical composition of claim 4, wherein the inhibitor of DNA repair is pirenzepine or a metabolite thereof.

7. A method for the preparation of the pharmaceutical composition of claim 2, comprising formulating a therapeutically effective amount of the monoclonal antibody of claim 1 in a pharmaceutically acceptable form.

8. A hybridoma cell line producing the monoclonal antibody of claim 1.

9. A test kit for the detection and diagnosis of amyloid-associated diseases and conditions comprising a container holding the monoclonal antibody of claim 1 and instructions for using the test kit.

10. A monoclonal antibody produced by the hybridoma cell line FP 12H3-C2, deposited as DSM ACC2750.

11. The hybridoma cell line FP 12H3-C2, deposited as DSM ACC2750.

12. A monoclonal antibody which specifically binds to monomeric, oligomeric or polymeric forms of amyloid-β, wherein the CDR1 of the light chain has the amino acid sequence of SEQ ID NO:23; the CDR2 of the light chain has the amino acid sequence of SEQ ID NO:24; and the CDR3 of the light chain has the amino acid sequence of SEQ ID NO:25.

13. A monoclonal antibody which specifically binds to monomeric, oligomeric or polymeric forms of amyloid-β, wherein the CDR1 of the heavy chain has the amino acid sequence of SEQ ID NO:26; the CDR2 of the heavy chain has the amino acid sequence of SEQ ID NO:27; and the CDR3 of the heavy chain has the amino acid sequence of SEQ ID NO:28.

14. A monoclonal antibody which specifically binds to monomeric, oligomeric or polymeric forms of amyloid-β, wherein the light chain variable region has the amino acid sequence of SEQ ID NO:7.

15. A monoclonal antibody which specifically binds to monomeric, oligomeric or polymeric forms of amyloid-β, wherein the heavy chain variable region has the amino acid sequence of SEQ ID NO:8.

* * * * *

UNITED STATES PATENT AND TRADEMARK OFFICE
Certificate

Patent No. 7,772,375 B2                                               Patented: August 10, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Ruth Greferath, Kehl (DE); Andreas Muhs, Pully (CH); Andrea Pfeifer, St. Légier (CH); and Claude Nicolau, Newton, MA (US).

Signed and Sealed this Ninth Day of April 2013.

<div align="right">

JEFFREY STUCKER
*Supervisory Patent Examiner*
Art Unit 1649
Technology Center 1600

</div>

```
                        SEQUENCE LISTING

<160> NUMBER OF SEQ ID NOS: 45

<210> SEQ ID NO 1
<211> LENGTH: 15
<212> TYPE: PRT
<213> ORGANISM: Homo sapiens

<400> SEQUENCE: 1

Asp Ala Glu Phe Arg His Asp Ser Gly Tyr Glu Val His His Gln
1               5                   10                  15

<210> SEQ ID NO 2
<211> LENGTH: 16
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

<210> SEQ ID NO 3
<211> LENGTH: 15
<212> TYPE: PRT
<213> ORGANISM: Homo sapiens

<400> SEQUENCE: 3

Asp Ala Glu Phe Arg His Asp Ser Gly Tyr Glu Val His Gln Lys
1               5                   10                  15

<210> SEQ ID NO 4
<211> LENGTH: 14
```

```
<212> TYPE: PRT
<213> ORGANISM: Homo sapiens

<400> SEQUENCE: 4

Glu Asp Val Gly Ser Asn Lys Gly Ala Ile Ile Gly Leu Met
1               5                   10

<210> SEQ ID NO 5
<211> LENGTH: 12
<212> TYPE: PRT
<213> ORGANISM: Homo sapiens

<400> SEQUENCE: 5

Gly Ala Ile Ile Gly Leu Met Val Gly Gly Val Val
1               5                   10

<210> SEQ ID NO 6
<211> LENGTH: 17
<212> TYPE: PRT
<213> ORGANISM: Homo sapiens

<400> SEQUENCE: 6

Asp Ala Glu Phe Arg His Asp Ser Gly Tyr Glu Val His His Gln Lys
1               5                   10                  15

Leu

<210> SEQ ID NO 7
<211> LENGTH: 112
<212> TYPE: PRT
<213> ORGANISM: Homo sapiens

<400> SEQUENCE: 7

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 8
<211> LENGTH: 112
<212> TYPE: PRT
<213> ORGANISM: Mus musculus

<400> SEQUENCE: 8

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45

Ala Ser Ile Asn Ser Asn Gly Gly Ser Thr Tyr Tyr Pro Asp Ser Val
```

|  | 50 | | | 55 | | | 60 | | | |
|---|---|---|---|---|---|---|---|---|---|---|

Lys Gly Arg Phe Thr Ile Ser Arg Asp Asn Ala Lys Asn Thr Leu Tyr
65                 70               75                 80

Leu Gln Met Ser Ser Leu Lys Ser Glu Asp Thr Ala Met Tyr Tyr Cys
                85                   90                   95

Ala Ser Gly Asp Tyr Trp Gly Gln Gly Ser Thr Leu Thr Val Ser Ser
            100               105              110

<210> SEQ ID NO 9
<211> LENGTH: 336
<212> TYPE: DNA
<213> ORGANISM: Mus musculus

<400> SEQUENCE: 9

```
gatgttgtga tgacccaaac tccactctcc ctgcctgtca gtcttggaga tcaagcctcc    60
atctcttgca gatctagtca gagccttgta tatagtaatg gagacaccta tttacattgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctggagttt atttctgctc tcaaagtaca catgttcct   300
tggacgttcg gtggaggcac caagctagaa atcaaa                             336
```

<210> SEQ ID NO 10
<211> LENGTH: 417
<212> TYPE: DNA
<213> ORGANISM: Mus musculus

<400> SEQUENCE: 10

```
atgaagttgc ctgttaggct gttggtgctg atgttctgga ttcctgcttc cagcagtgat    60
gttgtgatga cccaaactcc actctccctg cctgtcagtc ttggagatca agcctccatc   120
tcttgcagat ctagtcagag ccttgtatat agtaatggag acaccatttt acattggtac   180
ctgcagaagc caggccagtc tccaaagctc ctgatctaca agtttccaa ccgattttct    240
ggggtcccag acaggttcag tggcagtgga tcagggacag atttcacact caagatcagc   300
agagtggagg ctgaggatct ggagttttat ttctgctctc aaagtacaca tgttccttgg   360
acgttcggtg aggcaccaa gctagaaatc aaacgggctg atgctgcacc aactgta      417
```

<210> SEQ ID NO 11
<211> LENGTH: 336
<212> TYPE: DNA
<213> ORGANISM: Mus musculus

<400> SEQUENCE: 11

```
gaggtgcagc tggtggagtc tgggggaggc ttagtgcagc ctggagggtc cctgaaactc    60
tcctgtgcag cctctggatt cactttcagt agctatggca tgtcttgggt tcgccagact   120
ccagacaaga ggctggaatt ggtcgcaagc atcaatagta atggtggtag cacctattat   180
ccagacagtg tgaagggccg attcaccatc tccagagaca tgccaagaa cacctgtac    240
ctgcaaatga gcagtctgaa gtctgaggac acagccatgt attactgtgc aagtggtgac   300
tactggggcc aaggctccac tctcacagtc tcctca                             336
```

<210> SEQ ID NO 12
<211> LENGTH: 408
<212> TYPE: DNA
<213> ORGANISM: Mus musculus

<400> SEQUENCE: 12

```
atgrasttsg ggytcagmtt grttttcctt gcccttattt taaaaggtgt ccaatgtgag    60
gtgcagctgg tggagtctgg gggaggctta gtgcagcctg gagggtccct gaaactctcc   120
tgtgcagcct ctggattcac tttcagtagc tatggcatgt cttgggttcg ccagactcca   180
gacaagaggc tggaattggt cgcaagcatc aatagtaatg gtggtagcac ctattatcca   240
gacagtgtga agggccgatt caccatctcc agagacaatg ccaagaacac cctgtacctg   300
caaatgagca gtctgaagtc tgaggacaca gccatgtatt actgtgcaag tggtgactac   360
tggggccaag gctccactct cacagtctcc tcagccaaaa caacaccc                408
```

<210> SEQ ID NO 13
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Asn or Gln
<220> FEATURE:
<221> NAME/KEY: MOD_RES
<222> LOCATION: (5)..(5)
<223> OTHER INFORMATION: Ala, Val, Leu, norleucine, Met, Phe or Ile
<220> FEATURE:
<221> NAME/KEY: MOD_RES
<222> LOCATION: (6)..(6)
<223> OTHER INFORMATION: Ala, Val, Leu, norleucine, Met, Phe or Ile
<220> FEATURE:
<221> NAME/KEY: MOD_RES
<222> LOCATION: (7)..(7)
<223> OTHER INFORMATION: Ala, Val, Leu, norleucine, Met, Phe or Ile
<220> FEATURE:
<221> NAME/KEY: MOD_RES
<222> LOCATION: (8)..(8)
<223> OTHER INFORMATION: Ala, Val, Leu, Ser or Ile
<220> FEATURE:
<221> NAME/KEY: MOD_RES
<222> LOCATION: (9)..(9)
<223> OTHER INFORMATION: Glu or Asp
<220> FEATURE:
<221> NAME/KEY: MOD_RES
<222> LOCATION: (10)..(10)
<223> OTHER INFORMATION: Glu or Asp

<400> SEQUENCE: 13

```
His Xaa Lys Leu Xaa Xaa Xaa Xaa Xaa Xaa
1               5                   10
```

<210> SEQ ID NO 14
<211> LENGTH: 11
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: His, Asn, Gln, Lys or Arg
<220> FEATURE:
<221> NAME/KEY: MOD_RES
<222> LOCATION: (3)..(3)
<223> OTHER INFORMATION: Asn or Gln
<220> FEATURE:
<221> NAME/KEY: MOD_RES
<222> LOCATION: (4)..(4)
<223> OTHER INFORMATION: His, Asn, Gln, Lys or Arg
<220> FEATURE:
<221> NAME/KEY: MOD_RES
<222> LOCATION: (5)..(5)
<223> OTHER INFORMATION: Ala, Val, Leu, Ser or Ile
<220> FEATURE:
<221> NAME/KEY: MOD_RES
<222> LOCATION: (6)..(6)

```
<223> OTHER INFORMATION: Ala, Val, Leu, Ser or Ile
<220> FEATURE:
<221> NAME/KEY: MOD_RES
<222> LOCATION: (9)..(9)
<223> OTHER INFORMATION: Ala, Val, Leu, Ser or Ile
<220> FEATURE:
<221> NAME/KEY: MOD_RES
<222> LOCATION: (10)..(10)
<223> OTHER INFORMATION: Glu or Asp
<220> FEATURE:
<221> NAME/KEY: MOD_RES
<222> LOCATION: (11)..(11)
<223> OTHER INFORMATION: Glu or Asp

<400> SEQUENCE: 14

Xaa His Xaa Xaa Xaa Xaa Phe Phe Xaa Xaa Xaa
1               5                   10

<210> SEQ ID NO 15
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: His, Asn, Gln, Lys or Arg
<220> FEATURE:
<221> NAME/KEY: MOD_RES
<222> LOCATION: (2)..(2)
<223> OTHER INFORMATION: Asn or Gln
<220> FEATURE:
<221> NAME/KEY: MOD_RES
<222> LOCATION: (5)..(5)
<223> OTHER INFORMATION: Ala, Val, Leu, norleucine, Met, Phe or Ile
<220> FEATURE:
<221> NAME/KEY: MOD_RES
<222> LOCATION: (8)..(8)
<223> OTHER INFORMATION: Ala, Val, Leu, Ser or Ile
<220> FEATURE:
<221> NAME/KEY: MOD_RES
<222> LOCATION: (9)..(9)
<223> OTHER INFORMATION: Glu or Asp
<220> FEATURE:
<221> NAME/KEY: MOD_RES
<222> LOCATION: (10)..(10)
<223> OTHER INFORMATION: Glu or Asp

<400> SEQUENCE: 15

Xaa Xaa Lys Leu Xaa Phe Phe Xaa Xaa Xaa
1               5                   10

<210> SEQ ID NO 16
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Asn or Gln
<220> FEATURE:
<221> NAME/KEY: MOD_RES
<222> LOCATION: (5)..(5)
<223> OTHER INFORMATION: Ala, Val, Leu, norleucine, Met, Phe or Ile
<220> FEATURE:
<221> NAME/KEY: MOD_RES
<222> LOCATION: (8)..(8)
<223> OTHER INFORMATION: Ala, Val, Leu, Ser or Ile
<220> FEATURE:
<221> NAME/KEY: MOD_RES
<222> LOCATION: (9)..(9)
<223> OTHER INFORMATION: Glu or Asp
<220> FEATURE:
<221> NAME/KEY: MOD_RES
<222> LOCATION: (10)..(10)
<223> OTHER INFORMATION: Glu or Asp
```

<400> SEQUENCE: 16

His Xaa Lys Leu Xaa Phe Phe Xaa Xaa Xaa
1               5                   10

<210> SEQ ID NO 17
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: His, Asn, Gln, Lys or Arg
<220> FEATURE:
<221> NAME/KEY: MOD_RES
<222> LOCATION: (2)..(2)
<223> OTHER INFORMATION: Asn or Gln
<220> FEATURE:
<221> NAME/KEY: MOD_RES
<222> LOCATION: (5)..(5)
<223> OTHER INFORMATION: Ala, Val, Leu, norleucine, Met, Phe or Ile
<220> FEATURE:
<221> NAME/KEY: MOD_RES
<222> LOCATION: (8)..(8)
<223> OTHER INFORMATION: Ala, Val, Leu, Ser or Ile
<220> FEATURE:
<221> NAME/KEY: MOD_RES
<222> LOCATION: (9)..(9)
<223> OTHER INFORMATION: Glu or Asp

<400> SEQUENCE: 17

Xaa Xaa Lys Leu Xaa Phe Phe Xaa Xaa Asp
1               5                   10

<210> SEQ ID NO 18
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Asn or Gln
<220> FEATURE:
<221> NAME/KEY: MOD_RES
<222> LOCATION: (5)..(5)
<223> OTHER INFORMATION: Ala, Val, Leu, norleucine, Met, Phe or Ile
<220> FEATURE:
<221> NAME/KEY: MOD_RES
<222> LOCATION: (8)..(8)
<223> OTHER INFORMATION: Ala, Val, Leu, Ser or Ile
<220> FEATURE:
<221> NAME/KEY: MOD_RES
<222> LOCATION: (9)..(9)
<223> OTHER INFORMATION: Glu or Asp

<400> SEQUENCE: 18

His Xaa Lys Leu Xaa Phe Phe Xaa Xaa Asp
1               5                   10

<210> SEQ ID NO 19
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: His, Asn, Gln, Lys or Arg
<220> FEATURE:
<221> NAME/KEY: MOD_RES
<222> LOCATION: (2)..(2)
<223> OTHER INFORMATION: Asn or Gln
<220> FEATURE:
<221> NAME/KEY: MOD_RES

```
<222> LOCATION: (3)..(3)
<223> OTHER INFORMATION: Lys, His, Asn, Gln or Arg
<220> FEATURE:
<221> NAME/KEY: MOD_RES
<222> LOCATION: (5)..(5)
<223> OTHER INFORMATION: Ala, Val, Leu, norleucine, Met, Phe or Ile
<220> FEATURE:
<221> NAME/KEY: MOD_RES
<222> LOCATION: (8)..(8)
<223> OTHER INFORMATION: Ala, Val, Leu, Ser or Ile
<220> FEATURE:
<221> NAME/KEY: MOD_RES
<222> LOCATION: (9)..(9)
<223> OTHER INFORMATION: Glu or Asp
<220> FEATURE:
<221> NAME/KEY: MOD_RES
<222> LOCATION: (10)..(10)
<223> OTHER INFORMATION: Glu or Asp

<400> SEQUENCE: 19

Xaa Xaa Xaa Leu Xaa Phe Phe Xaa Xaa Xaa
1               5                   10

<210> SEQ ID NO 20
<211> LENGTH: 11
<212> TYPE: PRT
<213> ORGANISM: Homo sapiens

<400> SEQUENCE: 20

Val His His Lys Leu Val Phe Phe Ala Glu Asp
1               5                   10

<210> SEQ ID NO 21
<211> LENGTH: 219
<212> TYPE: PRT
<213> ORGANISM: Mus musculus

<400> SEQUENCE: 21

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190
```

```
Arg His Asn Ser Tyr Thr Cys Glu Ala Thr His Lys Thr Ser Thr Ser
        195                 200                 205

Pro Ile Val Lys Ser Phe Asn Arg Asn Glu Cys
        210                 215

<210> SEQ ID NO 22
<211> LENGTH: 448
<212> TYPE: PRT
<213> ORGANISM: Mus musculus

<400> SEQUENCE: 22

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Ser Gly Asp Tyr Trp Gly Gln Gly Ser Thr Leu Thr Val Ser Ser
            100                 105                 110

Ala Lys Thr Thr Pro Pro Ser Val Tyr Pro Leu Ala Pro Gly Cys Gly
        115                 120                 125

Asp Thr Thr Gly Ser Ser Val Thr Leu Gly Cys Leu Val Lys Gly Tyr
    130                 135                 140

Phe Pro Glu Ser Val Thr Val Thr Trp Asn Ser Gly Ser Leu Ser Ser
145                 150                 155                 160

Ser Val His Thr Phe Pro Ala Leu Leu Gln Ser Gly Leu Tyr Thr Met
                165                 170                 175

Ser Ser Ser Val Thr Val Pro Ser Ser Thr Trp Pro Ser Gln Thr Val
            180                 185                 190

Thr Cys Ser Val Ala His Pro Ala Ser Ser Thr Thr Val Asp Lys Lys
        195                 200                 205

Leu Glu Pro Ser Gly Pro Ile Ser Thr Ile Asn Pro Cys Pro Pro Cys
    210                 215                 220

Lys Glu Cys His Lys Cys Pro Ala Pro Asn Leu Glu Gly Gly Pro Ser
225                 230                 235                 240

Val Phe Ile Phe Pro Pro Asn Ile Lys Asp Val Leu Met Ile Ser Leu
                245                 250                 255

Thr Pro Lys Val Thr Cys Val Val Asp Val Ser Glu Asp Asp Pro
            260                 265                 270

Asp Val Gln Ile Ser Trp Phe Val Asn Asn Val Glu Val His Thr Ala
    275                 280                 285

Gln Thr Gln Thr His Arg Glu Asp Tyr Asn Ser Thr Ile Arg Val Val
    290                 295                 300

Ser Thr Leu Pro Ile Gln His Gln Asp Trp Met Ser Gly Lys Glu Phe
305                 310                 315                 320

Lys Cys Lys Val Asn Asn Lys Asp Leu Pro Ser Pro Ile Glu Arg Thr
                325                 330                 335

Ile Ser Lys Ile Lys Gly Leu Val Arg Ala Pro Gln Val Tyr Ile Leu
            340                 345                 350
```

```
Pro Pro Pro Ala Glu Gln Leu Ser Arg Lys Asp Val Ser Leu Thr Cys
        355                 360                 365

Leu Val Val Gly Phe Asn Pro Gly Asp Ile Ser Val Glu Trp Thr Ser
        370                 375                 380

Asn Gly His Thr Glu Glu Asn Tyr Lys Asp Thr Ala Pro Val Leu Asp
385                 390                 395                 400

Ser Asp Gly Ser Tyr Phe Ile Tyr Ser Lys Leu Asn Met Lys Thr Ser
                405                 410                 415

Lys Trp Glu Lys Thr Asp Ser Phe Ser Cys Asn Val Arg His Glu Gly
                420                 425                 430

Leu Lys Asn Tyr Tyr Leu Lys Lys Thr Ile Ser Arg Ser Pro Gly Lys
        435                 440                 445

<210> SEQ ID NO 23
<211> LENGTH: 16
<212> TYPE: PRT
<213> ORGANISM: Mus musculus

<400> SEQUENCE: 23

Arg Ser Ser Gln Ser Leu Val Tyr Ser Asn Gly Asp Thr Tyr Leu His
1               5                   10                  15

<210> SEQ ID NO 24
<211> LENGTH: 7
<212> TYPE: PRT
<213> ORGANISM: Mus musculus

<400> SEQUENCE: 24

Lys Val Ser Asn Arg Phe Ser
1               5

<210> SEQ ID NO 25
<211> LENGTH: 9
<212> TYPE: PRT
<213> ORGANISM: Mus musculus

<400> SEQUENCE: 25

Ser Gln Ser Thr His Val Pro Trp Thr
1               5

<210> SEQ ID NO 26
<211> LENGTH: 10
<212> TYPE: PRT
<213> ORGANISM: Mus musculus

<400> SEQUENCE: 26

Gly Phe Thr Phe Ser Ser Tyr Gly Met Ser
1               5                   10

<210> SEQ ID NO 27
<211> LENGTH: 17
<212> TYPE: PRT
<213> ORGANISM: Mus musculus

<400> SEQUENCE: 27

Ser Ile Asn Ser Asn Gly Gly Ser Thr Tyr Tyr Pro Asp Ser Val Lys Gly
1               5                   10                  15

<210> SEQ ID NO 28
<211> LENGTH: 3
<212> TYPE: PRT
<213> ORGANISM: Mus musculus
```

```
<400> SEQUENCE: 28

Gly Asp Tyr
1

<210> SEQ ID NO 29
<211> LENGTH: 9
<212> TYPE: PRT
<213> ORGANISM: Artificial Sequence
<220> FEATURE:
<223> OTHER INFORMATION: peptide used in second library

<400> SEQUENCE: 29

Val His His Gln Lys Leu Val Phe Phe
1               5

<210> SEQ ID NO 30
<211> LENGTH: 9
<212> TYPE: PRT
<213> ORGANISM: Artificial Sequence
<220> FEATURE:
<223> OTHER INFORMATION: peptide used in second library

<400> SEQUENCE: 30

Ala His His Gln Lys Leu Val Phe Phe
1               5

<210> SEQ ID NO 31
<211> LENGTH: 9
<212> TYPE: PRT
<213> ORGANISM: Artificial Sequence
<220> FEATURE:
<223> OTHER INFORMATION: peptide used in second library

<400> SEQUENCE: 31

Val Ala His Gln Lys Leu Val Phe Phe
1               5

<210> SEQ ID NO 32
<211> LENGTH: 9
<212> TYPE: PRT
<213> ORGANISM: Artificial Sequence
<220> FEATURE:
<223> OTHER INFORMATION: peptide used in second library

<400> SEQUENCE: 32

Val His Ala Gln Lys Leu Val Phe Phe
1               5

<210> SEQ ID NO 33
<211> LENGTH: 9
<212> TYPE: PRT
<213> ORGANISM: Artificial Sequence
<220> FEATURE:
<223> OTHER INFORMATION: peptide used in second library

<400> SEQUENCE: 33

Val His His Ala Lys Leu Val Phe Phe
1               5

<210> SEQ ID NO 34
<211> LENGTH: 9
<212> TYPE: PRT
<213> ORGANISM: Artificial Sequence
<220> FEATURE:
<223> OTHER INFORMATION: peptide used in second library
```

```
<400> SEQUENCE: 34

Val His His Gln Ala Leu Val Phe Phe
1               5

<210> SEQ ID NO 35
<211> LENGTH: 9
<212> TYPE: PRT
<213> ORGANISM: Artificial Sequence
<220> FEATURE:
<223> OTHER INFORMATION: peptide used in second library

<400> SEQUENCE: 35

Val His His Gln Lys Ala Val Phe Phe
1               5

<210> SEQ ID NO 36
<211> LENGTH: 9
<212> TYPE: PRT
<213> ORGANISM: Artificial Sequence
<220> FEATURE:
<223> OTHER INFORMATION: peptide used in second library

<400> SEQUENCE: 36

Val His His Gln Lys Leu Ala Phe Phe
1               5

<210> SEQ ID NO 37
<211> LENGTH: 9
<212> TYPE: PRT
<213> ORGANISM: Artificial Sequence
<220> FEATURE:
<223> OTHER INFORMATION: peptide used in second library

<400> SEQUENCE: 37

Val His His Gln Lys Leu Val Ala Phe
1               5

<210> SEQ ID NO 38
<211> LENGTH: 9
<212> TYPE: PRT
<213> ORGANISM: Artificial Sequence
<220> FEATURE:
<223> OTHER INFORMATION: peptide used in second library

<400> SEQUENCE: 38

Val His His Gln Lys Leu Val Phe Ala
1               5

<210> SEQ ID NO 39
<211> LENGTH: 9
<212> TYPE: PRT
<213> ORGANISM: Artificial Sequence
<220> FEATURE:
<223> OTHER INFORMATION: peptide used in third library

<400> SEQUENCE: 39

His His Gln Lys Leu Val Phe Phe Ala
1               5

<210> SEQ ID NO 40
<211> LENGTH: 9
<212> TYPE: PRT
<213> ORGANISM: Artificial Sequence
<220> FEATURE:
<223> OTHER INFORMATION: peptide used in third library

<400> SEQUENCE: 40
```

```
<210> SEQ ID NO 41
<211> LENGTH: 9
<212> TYPE: PRT
<213> ORGANISM: Artificial Sequence
<220> FEATURE:
<223> OTHER INFORMATION: peptide used in third library

<400> SEQUENCE: 41

His Gln Lys Leu Val Phe Phe Ala Glu
1               5

<210> SEQ ID NO 42
<211> LENGTH: 9
<212> TYPE: PRT
<213> ORGANISM: Artificial Sequence
<220> FEATURE:
<223> OTHER INFORMATION: peptide used in third library

<400> SEQUENCE: 42

His Gln Lys Leu Val Phe Phe Ala Ala
1               5

<210> SEQ ID NO 43
<211> LENGTH: 9
<212> TYPE: PRT
<213> ORGANISM: Artificial Sequence
<220> FEATURE:
<223> OTHER INFORMATION: peptide used in third library

<400> SEQUENCE: 43

Gln Lys Leu Val Phe Phe Ala Glu Asp
1               5

<210> SEQ ID NO 44
<211> LENGTH: 9
<212> TYPE: PRT
<213> ORGANISM: Artificial Sequence
<220> FEATURE:
<223> OTHER INFORMATION: peptide used in third library

<400> SEQUENCE: 44

Gln Lys Leu Val Phe Phe Ala Glu Ala
1               5

<210> SEQ ID NO 45
<211> LENGTH: 12
<212> TYPE: PRT
<213> ORGANISM: Homo sapiens

<400> SEQUENCE: 45

Val His His Gln Lys Leu Val Phe Phe Ala Glu Asp
1               5                   10
```

His His Gln Lys Leu Val Phe Phe Gly
1               5